US009603952B2

(12) United States Patent
O'Neill et al.

(10) Patent No.: US 9,603,952 B2
(45) Date of Patent: *Mar. 28, 2017

(54) TREATMENT OF METASTATIC TUMORS

(71) Applicant: MORPHOTEK, INC., Exton, PA (US)

(72) Inventors: Alison O'Neill, Cambridge, MA (US); Douglas B. Jacoby, Wellesley, MA (US); Abdellah Sentissi, Dover, MA (US); Kamala Kesavan, West Roxbury, MA (US); E. Michael Egan, Brookline, MA (US)

(73) Assignee: MORPHOTEK, INC., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/702,934

(22) Filed: May 4, 2015

(65) Prior Publication Data

US 2015/0374860 A1    Dec. 31, 2015

Related U.S. Application Data

(60) Continuation of application No. 13/479,203, filed on May 23, 2012, now Pat. No. 9,023,595, which is a division of application No. 12/466,599, filed on May 15, 2009, now Pat. No. 8,227,439.

(60) Provisional application No. 61/173,121, filed on Apr. 27, 2009, provisional application No. 61/153,273, filed on Feb. 17, 2009, provisional application No. 61/053,651, filed on May 15, 2008.

(51) Int. Cl.

| | |
|---|---|
| C07H 21/02 | (2006.01) |
| C07H 21/04 | (2006.01) |
| A61K 51/08 | (2006.01) |
| A61K 45/06 | (2006.01) |
| A61K 47/48 | (2006.01) |
| A61K 38/16 | (2006.01) |
| C12N 15/11 | (2006.01) |
| A61K 38/17 | (2006.01) |
| C12N 15/113 | (2010.01) |

(52) U.S. Cl.
CPC ............ *A61K 51/08* (2013.01); *A61K 38/164* (2013.01); *A61K 38/1767* (2013.01); *A61K 45/06* (2013.01); *A61K 47/48215* (2013.01); *A61K 47/48261* (2013.01); *C12N 15/111* (2013.01); *C12N 15/113* (2013.01); *C07K 2319/33* (2013.01); *C07K 2319/55* (2013.01); *C12N 2310/11* (2013.01); *C12N 2310/14* (2013.01); *C12N 2310/351* (2013.01); *C12N 2310/3513* (2013.01); *C12N 2320/31* (2013.01); *C12N 2320/32* (2013.01)

(58) Field of Classification Search
CPC ............................ A61K 48/00; C12N 2310/11
See application file for complete search history.

(56) References Cited

U.S. PATENT DOCUMENTS

| | | |
|---|---|---|
| 4,444,744 A | 4/1984 | Goldenberg |
| 5,051,364 A | 9/1991 | Isacke et al. |
| 5,212,290 A | 5/1993 | Vogelstein et al. |
| 5,223,253 A | 6/1993 | Hall et al. |
| 5,236,844 A | 8/1993 | Basset et al. |
| 5,314,992 A | 5/1994 | Guyre et al. |
| 5,591,829 A | 1/1997 | Matsushita |
| 5,626,862 A | 5/1997 | Brem et al. |
| 5,688,773 A | 11/1997 | Chiocca et al. |
| 5,750,376 A | 5/1998 | Weiss et al. |
| 5,756,340 A | 5/1998 | Hammock et al. |
| 5,866,570 A | 2/1999 | Liang et al. |
| 5,905,027 A | 5/1999 | Ullrich et al. |
| 5,935,795 A | 8/1999 | Lin et al. |
| 5,985,822 A | 11/1999 | Edelman et al. |
| 6,028,174 A | 2/2000 | Ullrich et al. |
| 6,130,101 A | 10/2000 | Mao et al. |
| 6,319,891 B1 | 11/2001 | Sontheimer et al. |
| 6,429,187 B1 | 8/2002 | Sontheimer et al. |
| 6,514,481 B1 | 2/2003 | Prasad et al. |
| 6,555,652 B1 | 4/2003 | Itoh et al. |
| 6,667,156 B2 | 12/2003 | Lyons et al. |
| 6,767,635 B1 | 7/2004 | Bahr et al. |
| 6,849,714 B1 | 2/2005 | Bridon et al. |
| 6,870,029 B2 | 3/2005 | Sontheimer et al. |
| 6,926,896 B2 | 8/2005 | Bosslet et al. |
| 6,972,326 B2 | 12/2005 | Haugland et al. |
| 7,094,868 B2 | 8/2006 | Samoylova et al. |

(Continued)

FOREIGN PATENT DOCUMENTS

| | | |
|---|---|---|
| CN | 1924006 A | 3/2007 |
| CN | 101003788 A | 7/2007 |

(Continued)

OTHER PUBLICATIONS

Te Velde, E.A. et al., The use of fluorescent dyes and probes in surgical oncology, Eur. J. Surg. Oncol., 36(1):6-15 (2010).

Adelstein, S.J. et al., Radiotoxicity of iodine-125 and other auger-electron-emitting radionuclides: background to therapy, Cancer Biotherapy and Radiopharmaceuticals, 18(3):301-16 (2003).

Akabani et al., Dosimetry and Radiographic Analysis of 131 I-Labeled Anti—Tenascin 81C6 Murine Monoclonal Antibody in Newly Diagnosed Patients with Malignant Gliomas: A Phase II Study, Journal of Nuclear Medicine, 46(6):1042-1051 (2005).

(Continued)

*Primary Examiner* — Amy Bowman
(74) *Attorney, Agent, or Firm* — Choate, Hall & Stewart LLP; Brenda Herschbach Jarrell

(57) ABSTRACT

The present invention is directed to methods and methods for the treatment, inhibition and/or reduction, and detection of metastatic tumors. In some embodiments, the inventive methods include systemic (e.g., intravenous) administration of a chlorotoxin agent that may or may not be labeled. In some embodiments, the inventive methods allow treatment, inhibition and/or reduction, and detection of metastases in the brain. In some embodiments, neovascularization is inhibited and/or newly formed vessels are caused to regress.

33 Claims, 27 Drawing Sheets

(56) References Cited

U.S. PATENT DOCUMENTS

| | | |
|---|---|---|
| 7,252,998 B2 | 8/2007 | Skerra et al. |
| 7,462,446 B2 | 12/2008 | Zhang et al. |
| 7,678,759 B2 | 3/2010 | Sontheimer et al. |
| 8,227,439 B2 | 7/2012 | O'Neill et al. |
| 8,470,607 B2 | 6/2013 | Jacoby et al. |
| 8,778,310 B2 | 7/2014 | Zhang et al. |
| 9,023,595 B2 | 5/2015 | O'Neill et al. |
| 9,234,015 B2 | 1/2016 | Sentissi et al. |
| 2001/0007025 A1 | 7/2001 | Bennett et al. |
| 2001/0055751 A1 | 12/2001 | Reiter et al. |
| 2002/0065216 A1 | 5/2002 | Sontheimer et al. |
| 2002/0146749 A1 | 10/2002 | Lyons et al. |
| 2003/0021810 A1 | 1/2003 | Sontheimer et al. |
| 2003/0201208 A1 | 10/2003 | Koch et al. |
| 2003/0216322 A1 | 11/2003 | Samoylova et al. |
| 2003/0232013 A1 | 12/2003 | Sieckman et al. |
| 2004/0101822 A1 | 5/2004 | Wiesner et al. |
| 2004/0102381 A1 | 5/2004 | Ekwuribe et al. |
| 2004/0105980 A1 | 6/2004 | Sudarshan et al. |
| 2004/0141981 A1 | 7/2004 | Sontheimer et al. |
| 2004/0180846 A1 | 9/2004 | Huang et al. |
| 2005/0142062 A1 | 6/2005 | Sontheimer et al. |
| 2005/0261191 A1 | 11/2005 | Barasch et al. |
| 2006/0019256 A1 | 1/2006 | Clarke et al. |
| 2006/0019347 A1 | 1/2006 | Cho et al. |
| 2006/0088899 A1 | 4/2006 | Alvarez et al. |
| 2006/0166892 A1 | 7/2006 | Alvarez et al. |
| 2007/0071764 A1 | 3/2007 | Sullivan et al. |
| 2007/0154965 A1 | 7/2007 | Zhang et al. |
| 2007/0237714 A1 | 10/2007 | Alvarez |
| 2007/0275902 A1 | 11/2007 | Gonda et al. |
| 2008/0153745 A1 | 6/2008 | Tian |
| 2008/0153746 A1 | 6/2008 | Alvarez et al. |
| 2008/0279780 A1 | 11/2008 | Zhang et al. |
| 2009/0004105 A1 | 1/2009 | Cheng et al. |
| 2009/0123946 A1 | 5/2009 | Birkenmeyer et al. |
| 2009/0123970 A1 | 5/2009 | Tu et al. |
| 2009/0124022 A1 | 5/2009 | Birkenmeyer et al. |
| 2009/0176274 A1 | 7/2009 | Tu et al. |
| 2009/0203598 A1 | 8/2009 | McCarty et al. |
| 2009/0263894 A1 | 10/2009 | Birkenmeyer et al. |
| 2009/0269777 A1 | 10/2009 | Birkenmeyer et al. |
| 2009/0304592 A1 | 12/2009 | O'Neill et al. |
| 2009/0311224 A1 | 12/2009 | Lee et al. |
| 2010/0098637 A1 | 4/2010 | Orringer et al. |
| 2010/0105150 A1 | 4/2010 | Adamczyk et al. |
| 2010/0210546 A1 | 8/2010 | Alvarez et al. |
| 2010/0215575 A1 | 8/2010 | O'Neill et al. |
| 2010/0215576 A1 | 8/2010 | Sontheimer et al. |
| 2011/0027177 A1 | 2/2011 | Jacoby et al. |
| 2011/0091380 A1 | 4/2011 | Jacoby et al. |
| 2011/0311445 A1 | 12/2011 | Alvarez et al. |
| 2012/0156131 A1 | 6/2012 | Alvarez |
| 2012/0183544 A1 | 7/2012 | Sontheimer et al. |
| 2013/0028836 A1 | 1/2013 | Sentissi et al. |
| 2013/0045163 A1 | 2/2013 | O'Neill et al. |
| 2013/0195760 A1 | 8/2013 | Olson |
| 2014/0241993 A1 | 8/2014 | Zhang et al. |
| 2015/0010473 A1 | 1/2015 | Alvarez |

FOREIGN PATENT DOCUMENTS

| | | |
|---|---|---|
| CN | 101270158 A | 9/2008 |
| CN | 101381405 A | 3/2009 |
| CN | 101824084 A | 9/2010 |
| CN | 101921769 A | 12/2010 |
| CN | 102844044 A | 12/2012 |
| EP | 0155396 A2 | 9/1985 |
| EP | 1430131 A2 | 6/2004 |
| EP | 2182004 A1 | 5/2010 |
| JP | H08-505615 A | 6/1996 |
| JP | 96325291 | 12/1996 |
| JP | H08-325291 A | 12/1996 |
| JP | H09-071599 A2 | 3/1997 |
| JP | 2002542206 A | 12/2002 |
| JP | 2005537234 A | 12/2005 |
| JP | 2008-538506 A | 10/2008 |
| WO | WO-8802117 A1 | 3/1988 |
| WO | WO-9311222 A1 | 6/1993 |
| WO | WO-94/15615 A1 | 7/1994 |
| WO | WO-9724619 A1 | 7/1997 |
| WO | WO-99/29715 A1 | 6/1999 |
| WO | WO-00/62807 A1 | 10/2000 |
| WO | WO-00/62810 A1 | 10/2000 |
| WO | WO-03/000203 A2 | 1/2003 |
| WO | WO-03/008583 A2 | 1/2003 |
| WO | WO-03/101474 A1 | 12/2003 |
| WO | WO-03/101475 A1 | 12/2003 |
| WO | WO-2005002604 A1 | 1/2005 |
| WO | WO-2005107793 A2 | 11/2005 |
| WO | WO-2005099774 A2 | 3/2006 |
| WO | WO-2006040574 A2 | 4/2006 |
| WO | WO-2005053611 A2 | 5/2006 |
| WO | WO-2006095164 A1 | 9/2006 |
| WO | WO-2006/110581 A2 | 10/2006 |
| WO | WO-2006/110582 A1 | 10/2006 |
| WO | WO-2006/116156 A2 | 11/2006 |
| WO | WO-2006/115633 A2 | 12/2006 |
| WO | WO-2007044994 A2 | 4/2007 |
| WO | WO-2007047458 A2 | 4/2007 |
| WO | WO-2007117467 A2 | 10/2007 |
| WO | WO-2007137163 A2 | 11/2007 |
| WO | WO-2008/088422 A2 | 7/2008 |
| WO | WO-2008155134 A1 | 12/2008 |
| WO | WO-2009021136 A1 | 2/2009 |
| WO | WO-2009/049184 A2 | 4/2009 |
| WO | WO-2009052390 A1 | 4/2009 |
| WO | WO-2009052392 A1 | 4/2009 |
| WO | WO-2009052400 A1 | 4/2009 |
| WO | WO-2009062520 A1 | 5/2009 |
| WO | WO-2009/140599 | 6/2009 |
| WO | WO-2009108762 A2 | 9/2009 |
| WO | WO-2009117018 A1 | 9/2009 |
| WO | WO-2009156456 A1 | 12/2009 |
| WO | WO-2011057295 A2 | 5/2011 |
| WO | WO-2011/097533 A1 | 8/2011 |
| WO | WO-2011094671 A2 | 8/2011 |
| WO | WO-2011/142858 A2 | 11/2011 |
| WO | WO-2012/022742 A1 | 2/2012 |

OTHER PUBLICATIONS

Akabani et al., Dosimetry of 131 I-Labeled 81C6 Monoclonal Antibody Administered into Sugically Created Resection Cavities in Patients with Malignant Brain Tumors, J of Nucl. Med., 40:631-638 (1999).

Akcan, M. et al., Chemical Re-engineering of Chlorotoxin Improves Bioconjugation Properties for Tumor Imaging and Targeted Therapy, J. of Medicinal Chem., 54(3):782-7 (2011).

Amersham Biosciences Publication, Labelling of Proteins with CyOye N-hydroxysuccinimide Esters for Fluorescent Applications on the LEAOSeeker Homogeneous Imaging System, Leadseeker L8:1-4, (2001).

AnaSpec Database, Chlorotoxin (Cltx), A 36-amino acid Cl- channel blocker from Leiurus quinquestriatus scorpion venom, Catalog #AS-60770, 1 page, retrieved from the internet: http://www.anaspec.com/products/product.asp?id=30976 (last accessed Oct. 8, 2014).

Applebaum et al., Treatment of Malignant Lymphoma in 100 Patients With Chemotherapy, Total Body Irradiation, and Marrow Transplantation, J. Clin. Oncol., 5:1340-1341 (1987).

Author Not Known, CyDye™ mono-reactive NHS-Esters, Amersham Biosciences, pp. 1-20 (2002).

Baker, Effects of an epithelial Cl channel blocker on whole cell voltage clamp and patch clamp recordings from a human astrocytoma in culture, J. Physiol. 438:128-129 (1991).

Banks, W.A. et al., Delta sleep-inducing peptide crosses the blood-brain-barrier in dogs: some correlations with protein binding, Pharmacol. Biochem. Behav., 17(5):1009-14 (1982).

Berendsen, Herman JC, A Glimpse of the Holy Grail?, Science, 282:642-643 (1998).

(56) References Cited

OTHER PUBLICATIONS

Berlier, J. E. et al., Quantitative comparison of long-wavelength Alexa Fluor dyes to Cy dyes: fluorescence of the dyes and their bioconjugates, J Histochem Cytochem, 51(12):1699-712 (2003).
Bertolini et al., Inhibition of angiogenesis and induction of endothelial and tumor cell apoptosis by green tea in animal models of human high-grade non-Hodgkin's lymphoma, Leukemia, 14:1477-1482 (2000).
Binger et al., Journal of Clinical Oncology, 16(6): 2202-2212 (1998).
Bodey et al., Failure of Cancer Vaccines: The Significant Limitations of this Approach to Immunotherapy, Anticancer Res., 20: 2665-2667 (2000).
Bowie et al., Deciphering the Message in Protein Sequences: Tolerance to Amino Acid Substitutions, Science, 257:1306-1310 (1990).
Bradley and Barrick, Limits of Cooperativity in a Structurally Modular Protein: Response of the Notch Ankyrin Domain to Analogous Alanine Substitutions in Each Repeat, J. Mol. Biol. 324:373-386 (2002).
Brem et al., Placebo-controlled trial of safety and efficacy of intraoperative controlled delivery by biodegradable polymers of chemotherapy for recurrent gliomas, The Lancet, 345:1008-1012 (1995).
Brismar, T. and Collins, V., Inward rectifying potassium channels in human malignant glioma cells, Brain Res. 480:249-258 (1989).
Brismar, T. and Collins, V., Potassium and sodium channels in human malignant glioma cells, Brain Res. 480:259-267 (1989).
Britton et al, Prostate cancer: the contribution of nuclear medicine, BJU Int'l 86(1):135-142 (2000).
Burger et al., Topographic anatomy and CT correlations in the untreated glioblastoma multiforme, J. Neurosurg, 68:698-704 (1988).
Burgess et al., Possible Dissociation of the Heparin-binding and Mitogenic Activities of Herparin-binding (Acidic Fibroblast) Growth Factor-1 from Its Receptor-binding Activities by Site-directed Mutagenesis of a Single Lysine Residue, J Cell Biol, 111:2129-2138 (1990).
Buskens et al., Adenocarcinomas of the Gastro-Esophageal Junction: A Comparative Study of the Gastric Cardia and the Esophagus with Respect to Cyclooxygenase-2 Expression, Digestive Disease Week Abstracts and Itinerary Planner (2003) Abstract 850.
Butterworth, M. D. et al., Preparation of Ultrafine Silica-and PEG-Coated Megnetite Particles, Colloids and Surfaces A: Physiochemical and Engineering Aspects 179:93-102 (2001).
Castro, M.G. et al., Gene therapy for Parkinson's disease: recent achievements and remaining challenges, Histl. Histopathol. 16(4):1225-1238 (2001).
Chien et al., The two-hybrid system: A method to identify and clone genes for proteins that interact with a protein of interest, Proc. Natl. Acad. Sci. USA, 88:9578-9582 (1991).
Chiu, S. and Wilson G., The role of potassium channels in Schwann cell proliferation in Wallerian degeneration of explant rabbit sciatic nerves, J. Physiol. 408:199-222 (1989).
Chuthapisith et al. Annexins in human breast cancer: possible predictors of pathological response to neoadjuvant chemotherapy, European J of Cancer, 45:1274-81 (2009).
Citrin, D. et al., In vivo tumor imaging in mice with near-infrared labeled endostatin, Mol Cancer Ther, 3(4):481-8 (2004).
Communication pursuant to Article 94(3) EPC for European Application 09 150 772.3, 15 pages (Feb. 14, 2012).
Daly et al, Pumiliotoxin alkaloids: a new class of sodium channel agents, Biochem Pharmacol., 40(2):315-326 (1990).
Database Genesq of WO 2008/088422 A2, Alpha-scorpion toxin family member CTX toxin peptide analog, SEQ:473 (2008).
Davis, C. G., The many faces of epidermal growth factor repeats, The New Biologist, 2(5):410-419 (1990).
De Muralt, B. et al., Reactivity of antiglioma monoclonal antibodies for a large panel of cultured gliomas and other neuroectoderm derived tumors, Anticancer Res. 3:1-6 (1983).

Deane, K. and Mannie, M., An alternative pathway of B cell activation: stilbene disulfonates interact with a Cl binding motif on AEn-related proteins to stimulate motogenesis, Eur. J. Immunol. 22:1165-1171 (1992).
Debin, J. et al., Purification and characterization of chlorotoxin, a chloride channel ligand from the venom of the scorpion, Am. J. Physiol. 264:C361-369 (1993).
Debin, J.A. and Strichartz, G.R., Chloride channel inhibition by the venom of the scorpion Leiurus quinquestriatus, Toxicon. 29:1403-1408 (1991).
Definition of 'same' retrieved from http://dictionary.reference.com/browse/same on Jun. 20, 2012 4 pages.
Dermer, G.B., Another Anniversary for the War on Cancer, Bio/Technology, 12:320 (1994).
Deshane et al., Chlorotoxin inhibits glioma cell invasion via matrix metalloproteinase-2, Journal of Biological Chemistry 278(6):4135-4144 (2002).
Drexler, Recent Results on the Biology of Hodgkin and Reed-Sternberg cells, Leukemia and Lymphoma, 9:1-25 (1993).
Eck, S. and Wilson, J., Goodman & Gilman's The Pharmacological Basis of Therapeutics, McGraw-Hill, New York, p. 77-101 (1996).
Egleton, R.D. and Davis T.P., Development of neuropeptide drugs that cross the blood-brain barrier, NeuroRx, 2(1):44-53 (2005).
Entrez Gene entry for ANXA2 annexin A2, updated Aug. 26, 2010, downloaded from http://ncbi.nlm.nih.gov/gene/302.
Epstein et al., Morphological and Virological Investigations on Cultured Burkitt Tumor Lymphoblasts (Strain Raji), J. Natl. Cancer Inst., 37:547-559 (1966).
European Partial Search Report for EP10178613.5, 9 pages (Feb. 15, 2012).
European Search Report for EP09150772.3, 15 pages (Feb. 14, 2012).
Evans et al., Design of Nonpeptidal Ligands for a Peptide Receptor: Cholecystokinin Antagonists, J. Med. Chem., 30:1229-1239 (1987).
Examination Report for AU2008310664, 3 pages (Feb. 11, 2013).
Examination Report for EP08837002.8, 7 pages (Feb. 11, 2013).
Examination Report for European Application 09 747 680.8, 6 pages (May 22, 2014).
Extended European Search Report for 08873442.1, 9 pages (May 20, 2015).
Extended European Search Report for EP 11740464.0, 10 pages (Jul. 2, 2013).
Extended European Search Report for EP08837002.8, 9 pages (Nov. 23, 2010).
Extended European Search Report for EP09150772.3, 18 pages (Jul. 30, 2010).
Extended European Search Report for EP10178613, 26 pages (Jun. 4, 2012).
Extended European Search Report for European Application 09 176 234.4, 9 pages (Apr. 6, 2010).
Extended European Search Report for European Application 11 780 950.9 (Oct. 15, 2013).
Fauchere, Elements for the rational design of peptide drugs, Adv. Drug Res., 15:29-69 (1986).
Field and Song, A novel genetic system to detect protein-protein interactions, Nature, 340:245-246 (1989).
Fiveash et al, Tumor Specific Targeting of Intravenous <131>I-chlorotoxin (TM-601) in Patients With Recurrent Glioma, Int'l J of Radiation: Oncol. Biol. Physics 69(3):S257-S258 (2007).
Fiveash et al., Safety and Tolerance of Multiple Weekly of Intracavitary Injections of 131I-chlorotoxin (TM-601): Preliminary result of a prospective clinical trial in patients with recurrent gliobastoma multiforme, J. Clin. Oncol., ASCO Annual Meeting Proceedings Part I, 24(18S): Abstract 1555 (2006).
Free Dictionary citing American Heritage Medical Dictionary, 1 page (2007).
Freshney, Culture of Animal Cells, A Manual of Basic Technique, Alan R. Liss, Inc., 4 (1983).
Friedman, H. et al., Temozolomide and Treatment of Malignant Glioma1, Clinical Cancer Res., 6:2585-2597 (2000).
Goldstein, G. and Betz, A., The Blood Brain Barrier, Sci. Am. 255:74-83 (1986).

(56) References Cited

OTHER PUBLICATIONS

Gorecki, D.C., Prospects and problems of gene therapy: an update, Expert Opin. Emerging Drugs 6(2):187-198 (2001).
Gorman et al., The Hype and the Hope, Time, 151(19):40-44 *1998).
Gray, P.T.A. and Ritchie, J.M., A voltage-gated chloride conductance in rat cultured astrocytes, Proc. R. Soc. Land. 228:267-288 (1986).
Grimes et al., TM-601 targets human cancer cells via a phosphatidylinositol phosphate in lamellipodia, J. Clin. Oncol., ASCO Annual Meeting Proceedings Part I, Abstract 9556 (2005).
Grissmer, S. et al., Calcium-activated potassium channels in resting and activated human T lymphocytes, J. Gen. Phys. 102(4):601-630 (1993).
Grossman and Batara, Current management of glioblastoma multiforme, Semin. Oncol., 31:635-644 (2004).
Gunn, J. et al., Smart Superparamagnetic Imaging Probes for Brain Tumor Research, in D.B. Baer and C.T. Campbell (eds.) Joint Institute for Nanoscience Annual Report, 2004, Nov. 2005, pp. 3.65-3.66.
Gura, T., Systems for Identifying New Drugs are Often Faulty, Sci., 278:1041-1042 (1997).
Hajjar, K.A. and Krishnan, S., "Annexin II: A Mediator of the Plasmin/Plasminogen Activator System," Trends in Cardiovascular Medicine 9(5):128-138 (1999).
Hamman, J.H. et al., Oral delivery of peptide drugs: barriers and developments, Biodrugs 19(3):165-177 (2005).
Hartwell et al., Integrating Genetic Approaches into the Discovery of Anticancer Drugs, Science, 278:1064-1068 (1997).
Hockaday, D. et al., Imaging Glioma Extent with 131 1-TM-601, J. Nucl. Med. 46(4):580-586 (2005).
Holmes, K. and Lantz, L., Protein Labeling with Fluorescent Probes, Methods in Cell Biology 63:185-204 (2001).
Hosli, E and Hosli, L., Evidence for GABA-B receptors on cultured astrocytes of rat CNS: autoradiographic binding studies, Exp. Brain. Res. 80:621-625 (1990).
Huang, Y. and Rane S., Potassium channel induction by the Ras/Raf signal transduction cascade, J. Biol. Chem. 269(49):31183-31189 (1994).
Huys, I. et al., Structure-function study of a chlorotoxin-chimer and its activity on Kv1.3 channels, J Chromatogr B Analyt Technol Biomed Life Sci, 803(1):67-73 (2004).
International Preliminary Report on Patentability for PCT/US04/39325, 4 pages (May 29, 2006).
International Preliminary Report on Patentability for PCT/US05/011523, 7 pages (Oct. 11, 2006).
International Preliminary Report on Patentability for PCT/US2007/008309, 9 pages (Sep. 30, 2008).
International Preliminary Report on Patentability for PCT/US2008/076740, 7 pages (Sep. 30, 2010).
International Preliminary Report on Patentability for PCT/US2008/079547, 4 pages (Apr. 13, 2010).
International Preliminary Report on Patentability for PCT/US2009/044149, 5 pages (Nov. 25, 2010).
International Preliminary Report on Patentability for PCT/US2011/023797, 6 pages (Nov. 13, 2012).
International Preliminary Report on Patentability for PCT/US2011/023823, 8 pages (Aug. 16, 2012).
International Search Report for PCT/US00/10453, Jun. 30, 2000.
International Search Report for PCT/US03/17410, 4 pages (Nov. 13, 2003).
International Search Report for PCT/US04/39325, 2 pages (Mar. 27, 2006).
International Search Report for PCT/US05/11523, 3 pages (Feb. 9, 2006).
International Search Report for PCT/US2006/010170, 5 pages (Oct. 6, 2006).
International Search Report for PCT/US2007/008309, 4 pages (Nov. 20, 2007).
International Search Report for PCT/US2008/076740, 3 pages (Jan. 1, 2009).
International Search Report for PCT/US2009/044149, 4 pages (Oct. 19, 2009).
International Search Report for PCT/US2011/023797, 6 pages (Nov. 18, 2011).
International Search Report for PCT/US2011/023823, 3 pages (Apr. 25, 2011).
International Search Report for PCT/US2013/074215 (Apr. 8, 2014).
International Search Report for PCT/US2013/074218 (Apr. 22, 2014).
International Search Report for PCT/US96/20403, Jul. 7, 1997.
Jacoby, D. et al., Potent Pleiotropic Anti-Angiogenic Effects of TM601, a Synthetic Chlorotoxin Peptide, Anticancer Res. 30:39-46 (2010).
Jalonen, T., Single-channel characteristics of the large-conductance anion channel in rat cortical astrocytes in primary culture, Glia 9:227-237 (1993).
Jiang, T. et al., Tumor imaging by means of proteolytic activation of cell-penetrating peptides, Proc Natl Acad Sci, USA, 101(51):17867-72 (2004).
Jianping, Z., Chinese and Foreign Sciences Yearbook, The Second Military Medical Uniersity (SMMU) Press, p. 426 (2004).
Kaiser, First Pass at Cancer Genome Reveals Complex Landscape, Science, 313:1370 (2006).
Kastin, A.J. and Akerstrom V., Orexin A but not orexin B rapidly enters brain from blood by simple diffusion, J. Pharmacol. Exp. Ther., 289(1):219-23 (1999).
Kaye, F.J. et al., A single amino acid substitution results in a retinoblastoma protein defective in phosphorylation and oncoprotein binding, Proc. Natl. Acad. Sci. USA 87(17):6922-6926 (1990).
Kesavan, K. et al., "Annexin A2 is a Molecular Target for TM601, a Peptide with Tumor-Targeting and Anti-angiogenic Effects," Journal of Biological Chemistry 285(7):4366-4374 (2010).
Kessler, R. et al., "Identification of the Putative Brain Tumor Antigen BF7/GE2 as the (De)Toxifying Enzyme Microsomal Epoxide Hydrolase." Published by the American Association for Cancer Research, Philadelphia. PA, Cancer Research 60:1403-1409 (2000).
Kimura, R. et al., A Dual-Labeled Knottin Peptide for PET and Near-Infrared Fluorescence Imaging of Integrin Expression in Living Subjects, Bioconjugage Chem. 21(3):436-444 (2010).
Kirkin et al., Melanoma-associated antigens recognized by cytotoxic T lymphocytes, APMIS, 106: 665-679 (1998).
Klein et al., Surface lgm-Kappa Specificity on a Burkitt Lymphoma Cell In Vivo and in Derived Culture Lines, Cancer Res., 28:1300-1310 (1968).
Kohler, N. A bifunctional poly(ethylene glycol) silane immobilized on metallic oxide-based nanoparticles for conjugation with cell targeting agents, J Am Chem Soc, 126(23):7206-11 (2004).
Kuan et al., EGFRvIII as a promising target for antibody-based brain tumor therapy, Brain Tumor Pathol., 17:71-78 (2000).
Kunwar, S. et al., Cytotoxicity and antitumor effects of growth factor-toxin fusion proteins on human glioblastoma multiforme cells, J. Neurosurg. 79(4):569-576 (1993).
Laumonnier et al., Identification of the annexin A2 heterotetramer as a receptor for the plasmin-induced signaling in human peripheral monocytes, Blood, 107:3342-3349 (2006).
Lazar et al., Transforming Growth Factor ?: Mutation of Aspartic Acid 47 and Leucine 48 Results in Different Biological Activities, Mol Cell Biol, 8:1247-1252 (1998).
Lee et al., Increased Vaccine-Specific T Cell Frequiency After Peptide-Based Vaccination Correlates with Increased Susceptibility to In Vitro Stimulation But Does Not Lead to Tumor Regression ,J. Immunol, 163: 6292-6300 (1999).
Lee, M.J. et al., Rapid pharmacokinetic and biodistribution studies using cholorotoxin-conjugated iron oxide nanoparticles: a novel non-radioactive method, PLoS One, 5(3):e9536 (2010).
Levin, V.A., The place of hydroxyurea in the treatment of primary brain tumors, Database accession No. NLM1641655 (abstract), Seminars in Oncology, 19(3):34-39 (1992).

(56) References Cited

OTHER PUBLICATIONS

Lippens et al., NMR Sequencial Assignments and Solution Structure of Chlorotoxin, a Small scorpion Toxin that Blocks Chloride Channels, Biochemistry 34(1):13-21 (1995).
Lokman et al., The role of annexin A2 in tumorigenesis and cancer progression, Cancer Microenvironment, published online Mar. 5, 2001, DOI 10.1007/s12307-011-0064-9 (2011).
Lynch, Chemoprevention with Special reference to inherited colorectal cancer, Familial Cancer, 7:59-64 (2008).
Lyons, S. et al., Chlorotoxin, a Scorpion-Derived Peptide, Spcifically Binds to Gliomas and Tumors of Neuroectodermal Origin, GLIA 39:162-173 (2002).
Malinowska, D.H. et al., Recombinant chlorotoxin: An inhibitor of gastric Cl-channels, Biophysical Journal, 66(2):A100 (1994).
Mamelak et al, PhaseI/II Trial of Intracavitary 131I-TM-601 in Adult Patients with Recurrent High-Grade Glioma, Neuro-Oncology online, 5:340 (2003).
Mamelak, A. and Jacoby, D., Targeted Delivery of Antitumoral Therapy to Glioma and Other Malignancies with Synthetic Chlorotoxin (TM-601 ), Expert Opin. Drug Delivery 4(2):175-186 (2007).
Mamelak, A. et al., Phase I Single-Dose Study of Intracavitary-Administered Iodine-131-TM-601 in Adults With Recurrent High-Grade Glioma, J. Clinic. Oncology 24(22)3644-3650 (2006).
McFerrin and Sontheimer, A role for ion channels in glioma cell invasion, Neuron. Glia Biology, 2:39-49 (2005).
McKie, R., Cancer Research Set Back a Decade, The Observer, 1-4 (2001).
McMichael, Leukocyte Typing III, Oxford University Press, 302-363 and 432-469 (1987).
Mellman, Where Next for Cancer Immunotherapy?, The Scientist, 20(1): 47-56 (2006).
Merck, Chemotherapy: Prevention and Treatment of Cancer: Merck Manual Home Edition, online manual, entry 'methotrexate', http://www.merck.com/mmhe/print/sec15/ch182/ch182f.html, 4 pages, (accessed 2007).
Milross et al., Relationship of Mitotic Arrest and Apoptosis to Antitumor Effect of Paclitaxel, J. Nat'l Cancer Inst., 88:1308-1314 (1996).
Minowada et al., Rosette-Forming Human Lymphoid Cell Lines. I. Establishment and Evidence for Origin of Thymus-Derived Lymphocytes, J. Natl. Cancer Inst., 49:891-895 (1972).
Moiety, Definition of, from http://dictionary.reference.com/browse/moiety, pp. 1-3 (last accessed Aug. 26, 2010).
Mousa, S. et al., Potent anti-angiogenesis efficacy of chlorotoxin and its synergistic interactions with Anti-VEGF targets, American Association for Cancer Research Annual Meeting Proceedings, Abstract #268 (2008).
Muro et al., Convection-Enhanced and Local Delivery of Targeted Cytotoxins in the Treatment of Malignant Gliomas, Technology in Cancer Research and Treatment, 5(3):201-213, ISSN 1533-0346 (2006).
NCI Dictionary of Cancer Terms for Non-Hodgkin Lymphoma (Apr. 30, 2012).
Newlands et al., Temozolomide: A Review of Its Discovery, Chemical Properties, Pre-clinical Development and Clinical Trials, Cancer Treatment Reviews 23(1):35-61 (1997).
Ngo et al., Computational Complexity, Protein Structure Prediction, and The Levinthal Paradox, the Protein Folding Problem and Terriary Structure Prediction, 491-494 (1994).
Nilius, B. and Wohlrab, W., Potassium channels and regulation of proliferation of human melanoma cells, J. Physiol. 445:537-548 (1992).
O'Neill et al. "Treatment of Metastatic Tumors." U.S. Appl. No. 61/053,651, filed May 15, 2008. (Not published.).
Office Action for CA2487425, 5 pages (Oct. 24, 2012).
Office Action for Chinese Application 200980123047.4, 15 pages (Jun. 12, 2014).
Office Action for Chinese Application 200980123047.4, 18 pages (Apr. 8, 2013).
Office Action for CN 201180012427.8, 7 pages (Aug. 11, 2014).
Office Action for CN 201180012427.8, 8 pages (Sep. 30, 2013).
Office Action for JP 2011-500759, 3 pages (Jun. 3, 2014).
Office Action for JP2011-052039 dated Feb. 18, 2014.
Office Action for U.S. Appl. No. 11/897,721, 13 pages (Sep. 15, 2009).
Office Action for U.S. Appl. No. 11/897,721, 7 pages (Mar. 24, 2010).
Pappas, C. et al., Reduction of glial proliferation by K+ channel blockers is mediated by changes in pH;, NeuroReport 6:193-196 (1994).
Pappone, P. and Ortiz-Miranda, S., Blockers of voltage-gated K channels inhibit proliferation of cultured brown fat cells, Am. J. Physiol. 264(4 Pt 1):C1014-1019 (1993).
Partial European Search Report for EP09150772.3, 8 pages (Apr. 8, 2010).
Partial European Search Report for European Application 10 178 613.5, 9 pages (Feb. 15, 2012).
Phillips, P. et al., Transforming growth factor-alpha-pseudomonas exotoxin fusion protein (TGF-alpha-PE38) treatment of subcutaneous and intracranial human glioma and medulloblastoma xenografts in athymic mice, Cancer Research 54(4):1008-1015 (1994).
PTO892, 1 page (Nov. 6, 2012).
Puro, D. et al., Retinal glial cell proliferation and ion channels: A possible link, Invest. Ophthalmol. Vis. Sci. 30(3):521-529 (1989).
Ramakrishnan et al., Targeting Tumor Vasculature Using VEGF-Toxin Conjugates, Methods in Molecular Biology 166:219-234 (2001).
Ravic, M., Intracavitary treatment of malignant gliomas: radioimmunotherapy targeting fibronectin, Acta Neurochir, Suppl 88:77-82 (2003).
Rawstron et al., Quantitation of minimal disease levels in chronic lymphocytic leukemia using a sensitive flow cytometric assay improves the prediction of outcome and can be used to optimize therapy, Blood, 98:29-35 (2001).
Reardon et al., A pilot study: 131I-antitenascin monoclonal antibody 81c6 to deliver a 44-Gy resection cavity boost, Neuro-Oncology, 10(2):182-189 (2008).
Reardon et al., Phase II Trial of Murine 131 I-Labeled Antitenascin Monoclonal Antibody 81C6 Administered Into Surgically Created Resection Cavities of Patients With Newly Diagnosed Malignant Gliomas, J of Clin. Oncol., 20(5):389-1397 (2002).
Rescher, U. and Gerke, V., "Annexins-unique membrane binding proteins with diverse functions," Journal of Cell Science, 117:2631-2639 (2004).
Ricotti et al., c-kit is expressed in soft tissue sarcoma of neuroectodermic origin and its ligand prevents apoptosis of neoplastic cells, Blood, 91:2397-2405 (1998).
Rousselle, C. et al., New advances in the transport of doxorubicin through the blood-brain barrier by a peptide vector-mediated strategy, Mol. Pharmacol., 57(4):679-86 (2000).
Rudinger, Peptide Hormones, J.A. Parsons, Ed., pp. 1-7 (1976).
Sakamoto, H. et al., Identification of a new outwardly rectifying Cl-channel that belongs to a subfamily of the CIC Cl-channels, J. Biol. Chem. 271(17):10210-10216 (1996).
Sgouros, Bone Marrow Dosimetry for Radioimmunotherapy: Theoretical Considerations, J. Nucl. Med., 34:689-694 (1993).
Sharma and Sharma, The Role of Annexin II in Angiogenesis and Tumor Progression: A Potential Therapeutic Target, Current Pharmaceutical Design, 13:3568-3575 (2007).
Shen et al., Patient-Specific Dosimetry of Pretargeted Radioimmunotherapy Using CC49 Fusion Protein in Patients with Gastrointestinal Malignancies, J. Nucl. Med., 46:642-651 (2005).
Shen et al., Practical determination of patient-specific marrow dose using radioactivity concentration in blood and body, J. Nucl. Med., 40:2102-2106 (1999).
Shen et al., Radiation dosimetry of 131I-chlorotoxin for targeted radiotherapy in glioma-bearing mice, J. Neuro-Oncol., 71:113-119 (2005).
Shen, S. et al., Dosimetry of Phase I/II Study of Intracavitary Administered I-131-TM-601 Peptide in Patients with Recurrent High-Grade Glioma, Proceedings of the 46th Annual ASTRO Meeting, S259:1 (2004).

(56) References Cited

OTHER PUBLICATIONS

Shiue, L. Identification of candidate genes for drug discovery by differential display, Drug Development Research, New York, 41:142-159 (1997).
Sigma, Custom Peptide Synthesis, Sigma Genosys (2004).
Silva et al., Agents that bind annexin A2 suppress ocular neovascularization, J Cell. Physiol., 225:855 (2010).
Skolnick, J. and Fetrow, J.S., From genes to protein structure and function: novel applications of computational approaches in the genomic era, Trends in Biotech 18(1):34-39 (2000).
Smith et al., Molecular Markers in Head and Neck Squamous Cell Carcinoma: Their Biological Function and Prognostic Significance, Annals Otology, Rhinology, and Laryngology, 110(3): 221-228 (2001).
Somogyi. P. et al., Subcellular localization of benzodiazepine/GABAA receptors in the cerebellum of rat, cat and monkey using monoclonal antibodies, J. Neurosci. 9(6):2197-2209 (1989).
Sontheimer, H., Voltage-dependent ion channels in glial cells, Glia 11:156-172 (1994).
Soroceanu, L. et al., Modulation of glioma cell migration and invasion using Cl(−) and K(+) ion channel blockers, J. Neuroscience 19(14):5942-5954 (1999).
Soroceanu, L. et al., Use of chlorotoxin for targeting of primary brain tumors, Cancer Research 58(21):4871-4879 (1998).
Stabin, Mirdose: Personal computer. software for internal dose assessment in nuclear. medicine, J. Nucl. Med., 37:538-546 (1996).
Steinmeyer, K. et al., Cloning and functional expression of rat CLC-5, a chloride channel related to kidney disease, J. Biol. Chem. 270(52):31172-31177 (1995).
Stewart, Chemotherapy in adult high-grade glioma: a systematic review and meta-analysis of individual patient data from 12 randomised trials, Lancet, 359:1011-1018 (2002).
Stupp et al., Current and future developments in the use of temozolomide for the treatment of brain tumors, The Lancet, 2:552-560 (2001).
Sun et al., In Vivo MRI Detection of Gliomas by Chlorotoxin-Conjugated Superparamagnetic Nanoprobes Small, 4(3):372-379 (2008).
Sun, C. et al., Tumor-targeted drug delivery and MRI contrast enhancement by chlorotoxinconjugated iron oxide nanoparticles, NIH Public Access Author manuscript Nanomedicine, p. 1-16 (2008).
Sun, S. and Zeng, H. Size-controlled synthesis of magnetite nanoparticles, J Am Chem Soc, 124(28):8204-5 (2002).
Supplementary European Search Report for EP05763889.2, 4 pages (Sep. 24, 2007).
Supplementary Partial European Search Report for EP 00 92 6105, Mar. 11, 2003.
Supplementary Partial European Search Report for European Application 03 73 1504, 8 pages (Aug. 28, 2007).
Supplementary Partial European Search Report for European Application 08 87 3442, 4 pages (Jan. 23, 2015).
Syed et al., Angiostatin receptor annexin II in vascular tumors including angiosarcoma, Human Pathol., 38(3):508-13 (2007) Abstract.
Taber's Cyclopedic Medical Dictionary, F.A. Davis Company, Philadelphia, 274 (1985).
Tan, P. et al., Deduction of Functional Peptide Motifs in Scorpion Toxins, J. Peptide Science 12:420-427 (2006).
Tanaka et al., Redox regulation of annexin 2 and its implications for oxidative stress-induced renal carcinogenesis and metastasis, Oncogene, 23:3980-3989 (2004).
Tatenhorst, L. et al., Knockdown of annexin 2 decreases migration of human glioma cells in vitro, Neuropathology and Applied Neurobiology, 32(3):271-7 (2006).
Tatikolov, A.S. and Costa, S.M., Complexation of polymethine dyes with human serum albumin: a spectroscopic study, Biophys Chem, 107(1):33-49 (2004).
TMI 601 and TM801 Sequences (1 page).
Torchilin, V.P. and Lukyanov, A.N., Peptide and protein drug delivery to and into tumors: challenges and solutions, DDT 8(6):259-266 (2003).
Transmolecular, A Phase I Imaging and Safety Study of Intravenous 131-I-TM-601 Labeled Chlorotoxin in Patients With Recurrent or Refractory Somatic and/or Cerebral Metastatic Solid Tumors, Clinical Trials NCT00379132, 3pages (Aug. 2006).
Tytgat et al., Purification and partial characterization of a "short"insectotoxin-like peptide from the venom of the scorpion Parabuthus schlechteri, FEBS, 441:387-391 (1998).
Uchida, S. et al., Localization and functional characterization of rat kidney-specific chloride channel CIC-K1, J. Clin. Invest. 95(1):104-113 (1995).
Ullrich and Sontheimer, Cell cycle-dependent expression of a glioma-specific chloride current: proposed link to cytoskeletal changes, Am. J. Physiol., 273:C1290-1297 (1997).
Ullrich, N. and Sontheimer, H., Biophysical and Pharmacological Characterization of Chloride Currents in Human Astrocytoma Cells, Am. J. Physiology 270:C1511-C1521 (1996).
Ullrich, N. et al., Expression of Voltage-Activated Chloride Currents in Acute Slices of Human Gliomas, Neuroscience 83(4):1161-1173 (1998).
Ullrich, N. et al., Human astrocytoma cells express a unique chloride current, NeuroReport 7(5):1020-1024 (1996).
UniProt Database, Accession No. P45639 (accessed 2007).
Veber and Freidinger, The design of metabolically-stable peptide analogs, Trends Neurosci., 8:392-396 (1985).
Veiseh et al., Optical and MRI Multifunctional Nanoprobe for Targeting Gliomas, Nano Letters, 5(6):1003-1008 (2005).
Veiseh, M. et al., Tumor Paint: A Chlorotoxin: Cy5.5 Bioconjugate for Intraoperative Visualization of Cancer Foci, Caner Res. 67:6882-6888 (2007).
Veiseh, O. et al., A ligand-mediated nanovector for targeted gene delivery and transfection in cancer cells, Biomaterials, 30(4):649-657 (2009).
Veiseh, O. et al., Specific targeting of brain tumors with an optical/magnetic resonance imaging nanoprobe across the blood-brain barrier, Cancer Res, 69(15):6200-7 (2009).
Voet and Voet, Biochemistry, John Wiley & Sons, Inc., 235-241 (1995).
Weissleder, R. and Ntziachristos, V., Shedding light onto live molecular targets, Nat Med, 9(1):123-8 (2003).
Wen et al., PTEN controls tumor-induced angiogenesis, Proc Natl Acad Sci USA, 98:4622-4627 (2001).
Wilson, G. and Chiu, S., Mitogenic factors regulate ion channels in Schwann cells cultured from newborn rat sciatic nerve, J. Physiol. 470:501-520 (1993).
Wishart, D.S. et al., 1H, 13C and 15N chemical shift referencing in biomolecular Nmr, J Biomol NMR, 6(2):135-40 (1995).
Woodfork, K. et al., Inhibition of ATP-sensitive potassium channels causes reversible cellcycle arrest of human breast cancer cells in tissue culture, J. Cell. Physiol. 162:163-171 (1995).
Written Opinion for PCT/US04/39325, 3 pages (Mar. 27, 2006).
Written Opinion for PCT/US05/11523, 6 pages (Feb. 9, 2006).
Written Opinion for PCT/US2006/010170, 8 pages (Oct. 22, 2007).
Written Opinion for PCT/US2007/008309, 8 pages (Nov. 20, 2007).
Written Opinion for PCT/US2008/076740, 5 pages (Jan. 9, 2009).
Written Opinion for PCT/US2009/044149, 8 pages (Oct. 19, 2009).
Written Opinion for PCT/US2011/023797, 5 pages (Nov. 18, 2011).
Written Opinion for PCT/US2011/023823, 6 pages (Apr. 25, 2011).
Written Opinion for PCT/US2013/074215 (Apr. 8, 2014).
Written Opinion for PCT/US2013/074218 (Apr. 22, 2014).
Yasuda et al., Annexin A2 autoantibodies detected in serum of cancer patients, Anticancer Res., 30(7):2631-9 (2010).
Ye, Y. and Chen, X., Integrin Targeting for Tumor Optical Imaging, Theranostics 1:102-126 (2011).
Zellner et al., Disparity in expression of protein kinase C alpha in human glioma versus glioma-derived primary cell lines: therapeutic implications, Clin. Can. Res., 4:1797-1802 (1998).
Zhang, Y. et al., Surface modification of superparamagnetic magnetite nanoparticles and their intracellular uptake, Biomaterials, 23(7):1553-61 (2002).
Zips et al., New Anticancer Agents: In Vitro and In Vivo Evaluation, In Vivo, 19:1-8 (2005).

Melanoma to Brain

TM-601　　　　Control　　　　H&E stain

| | | |
|---|---|---|
| 8 | Glioma | 7 |
| 8 | Metastatic Melanoma | 7 |
| 8 | Colorectal | 6 |
| 5 | NSCL | 3 |
| 2 | Prostate | 2 |
| 3 | Pancreas | 2 |
| 4 | Breast | 1 |
| 1 | Transitional Cell Carcinoma | 1 |
| 1 | Metastatic Paraganglioma | 1 |
| 1 | Pleomorphic Xanthoastrcytoma | 1 |
| 2 | SCLC | 0 |
| 1 | CNS Lymphoma | 0 |
| 1 | Medullary Thyroid | 0 |
| 2 | Ovarian | 0 |
| 1 | Uterine | 0 |
| 48 | TOTALS | 31 |

Pretreatment MRI   3 weeks following 30 mCi dose

Inhibition of Choroidal Neovascularization

Regression of Pre-Existing New Vessels

TREATMENT OF METASTATIC TUMORS

RELATED APPLICATION INFORMATION

The present application is a Continuation of U.S. application Ser. No. 13/479,203, filed May 23, 2012, which is a Divisional of U.S. application Ser. No. 12/466,599, filed May 15, 2009, and issued on Jul. 24, 2012 as U.S. Pat. No. 8,227,439, which claims priority to and benefit of U.S. provisional application Nos. 61/053,651 (filed May 15, 2008), 61/153,273 (filed Feb. 17, 2009), and 61/173,121 (filed Apr. 27, 2009) the contents of each of which is herein incorporated by reference in their entirety.

In accordance with 37 CFR 1.52(e)(5), a Sequence Listing in the form of a text file (entitled "2012-10-26 Sequence", created on Aug. 12, 2015, and having a size of 40,117 bytes) is incorporated herein by reference in its entirety.

BACKGROUND

The ability of cancer cells to spread, or metastasize, is regarded as the most deadly aspect of cancer. Cancer cells may break away from a primary tumor and travel to other parts of the body via the bloodstream and/or lymphatic system, forming distant metastases. Treatment and diagnosis of such metastatic tumors presents a challenge, due in part to the number of metastases that can form and the distance from the site of primary tumor that metastases can travel. The most common sites of metastases include the lungs, bone, liver, and brain. Metastases that localize in the brain pose different challenges from those that form in other organs of the body due to the neuroprotective nature of the blood/brain barrier that hinders the delivery of many potentially effective diagnostics and therapeutics to the vasculature and neural tissue.

Chlorotoxin is a peptide found in venom from the Giant Yellow Israeli scorpion *Leiurus Quinqestriatus* that has been explored pre-clinically as a candidate for targeting gliomas with 131-iodine (J. A. DeBin et al., Am. J. Physiol. (Cell Physiol.), 1993, 264, 33: C361-C369; L. Soroceanu et al., Cancer Res., 1998, 58: 4871-4879; S. Shen et al., Neuro-Oncol., 2005, 71: 113-119). Compositions (see U.S. Pat. Nos. 5,905,027 and 6,429,187, the contents of each of which are hereby incorporated by reference in their entirety) and methods (see U.S. Pat. Nos. 6,028,174 and 6,319,891, the contents of each of which are hereby incorporated by reference in their entirety) for diagnosing and treating neuroectodermal tumors (e.g., gliomas and meningiomas) have been developed based on the ability of chlorotoxin to bind to tumor cells of neuroectodermal origin (Soroceanu et al., Cancer Res., 1998, 58: 4871-4879; Ullrich et al., Neuroreport, 1996, 7: 1020-1024; Ullrich et al., Am. J. Physiol., 1996, 270: C1511-C1521).

SUMMARY

The present invention encompasses the finding that chlorotoxin can target distant metastases including those found in the brain. The present invention also encompasses the finding that chlorotoxin can inhibit neovascularization and/or cause regression of existing newly formed blood vessels. Without wishing to be bound by any particular theory, the inventors propose that the usefulness of chlorotoxin in treating metastatic cancers may be due at least in part to its ability to inhibit the formation of new blood vessels, and/or to cause regression of newly formed blood vessels, on which metastases are thought to depend.

In one aspect, the invention provides methods for treatment of metastatic cancers comprising administering to an individual having or susceptible to at least one metastasis, wherein the metastasis arose from at least one primary tumor, an effective dose of a chlorotoxin agent such that the chlorotoxin agent binds to the at least one metastasis. In some embodiments, the chlorotoxin agent is delivered systemically; in some embodiments, the chlorotoxin agent is delivered intravenously. In some embodiments, the primary tumor is melanoma, such as cutaneous and/or intraocular melanoma. In some embodiments, the primary tumor is glioma.

In another aspect, the invention provides methods of detecting the presence of one or more metastases in an individual who has or has had at least one primary tumor, comprising administering to the individual an effective amount of a labeled chlorotoxin agent and measuring binding of the labeled chlorotoxin agent in the individual's body. In such aspects, elevated levels of binding relative to normal (non tumor) tissue in one or more areas of the body other than the site(s) of primary tumor(s) is indicative of the presence of one or more metastases. In some embodiments, administering a second effective amount of a labeled chlorotoxin agent at a second time period and measuring binding of the labeled chlorotoxin agent in the individual's body allows assessment of any change in binding (e.g., in extent and/or location of binding), which may be indicative of progression, stability, or regression of one or more metastases.

In some embodiments of the methods of treating and/or detecting metastases, the chlorotoxin agent is delivered systemically. Systemic administration may comprise intravenous administration. In some embodiments, the chlorotoxin agent binds to at least one tumor metastasis in the brain. In some embodiments, neovascularization is inhibited and/or newly formed blood vessels (which may feed metastases) are caused to regress.

BRIEF DESCRIPTION OF THE DRAWINGS

FIG. 5 is a table summarizing the tumor-specific uptake of $^{131}$I-TM-601 following intravenous administration in patients with different types of solid tumors.

FIG. 8 is comprised of parts (A) and (B). Part (A) of FIG. 8 shows a pre-treatment MRI showing a left frontal lesion of a patient with metastatic melanoma (left), and a SPECT image recorded following intravenous injection of $^{131}$I-TM-601 (30 mCi/0.2 mg) to the patient (right). Part (B) of FIG. 8 shows a pre-treatment Magnetic Resonance Image (MRI) showing the right occipital lesion of a patient with metastatic melanoma (left), and a SPECT image recorded following intravenous injection of $^{131}$I-TM-601 (30 mCi/0.2 mg) to the patient (right).

Coregistration of the three stains is shown on the bottom row (G, H). TUNEL-positive cells within the CNV lesions (E) were found in eyes that had intraocular injections of TM-601 (A, C, E, and G). No TUNEL-positive cells were observed in eyes that received injections of vehicle (B, D, F, and H). Arrows show the CNV area.

Figure 23:
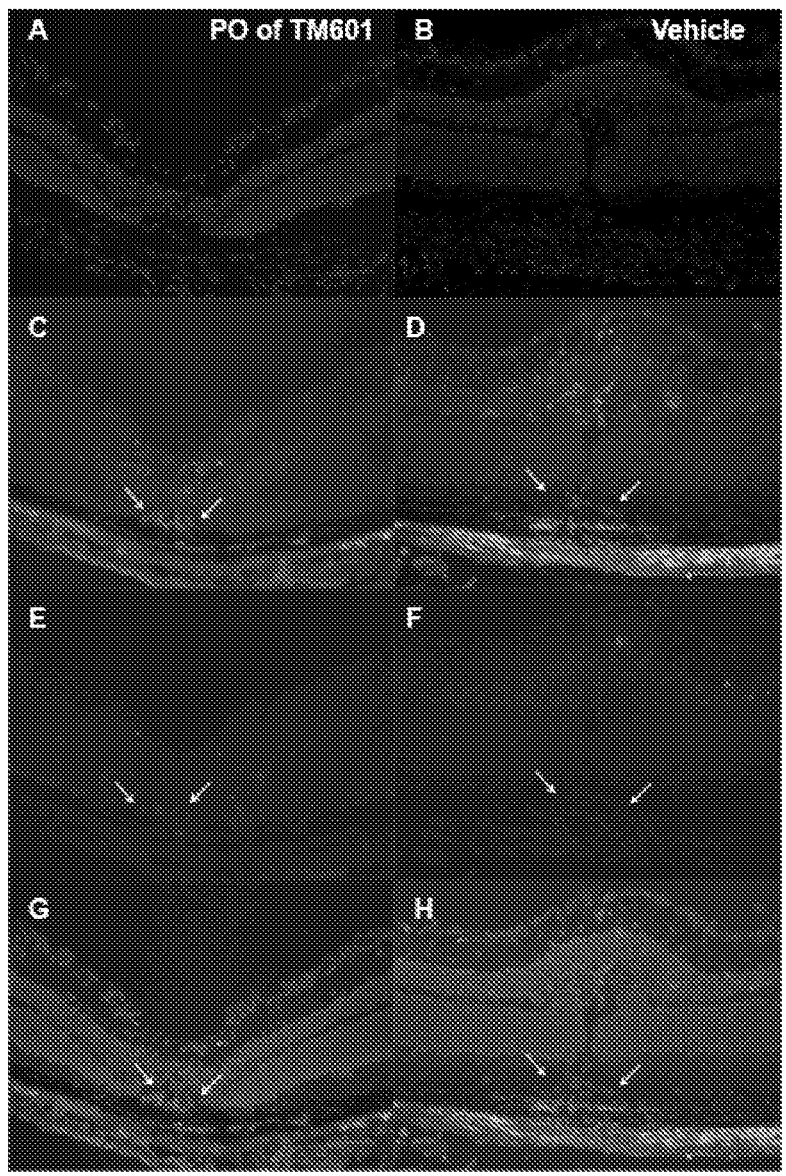

FIG. 23 depicts microscope images of frozen sections showing the effect of TM-601 on apoptosis within CNV lesions by periocular injection. TM-601 was injected and mice were euthanized as described for FIG. 16. (See also Materials and Methods in Example 6). Sections were stained with nuclear stain (A, B), GSA (C, D), and TUNEL (E, F). Coregistration of the three stains is shown on the bottom row (G, H). TUNEL-positive cells within the CNV lesions (E) were found in eyes that had periocular injections of TM-601 (A, C, E, and G). No TUNEL-positive cells were observed in eyes that received injections of vehicle (B, D, F, and H). Arrows show the CNV area.

Figure 24:
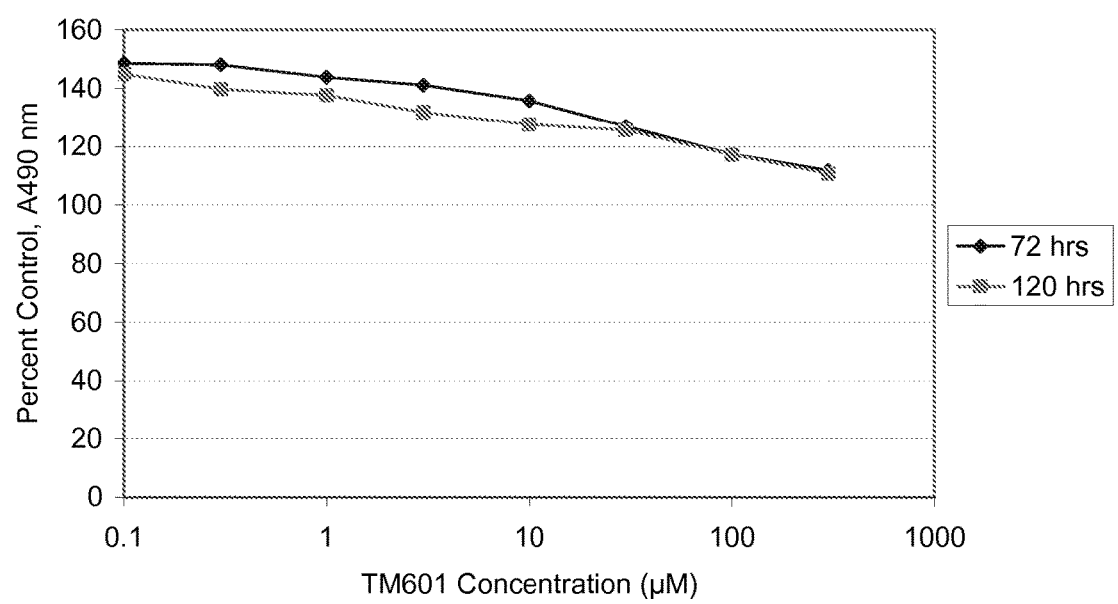

FIG. 24 depicts results from experiments measuring HUVEC cell proliferation in the presence of a range of TM-601 concentrations for either 72 or 120 hrs. Although cell proliferation at higher TM-601 concentrations was less than at lower concentration of TM-601, the proliferation rate was not less than that of untreated control cells.

Figure 25:
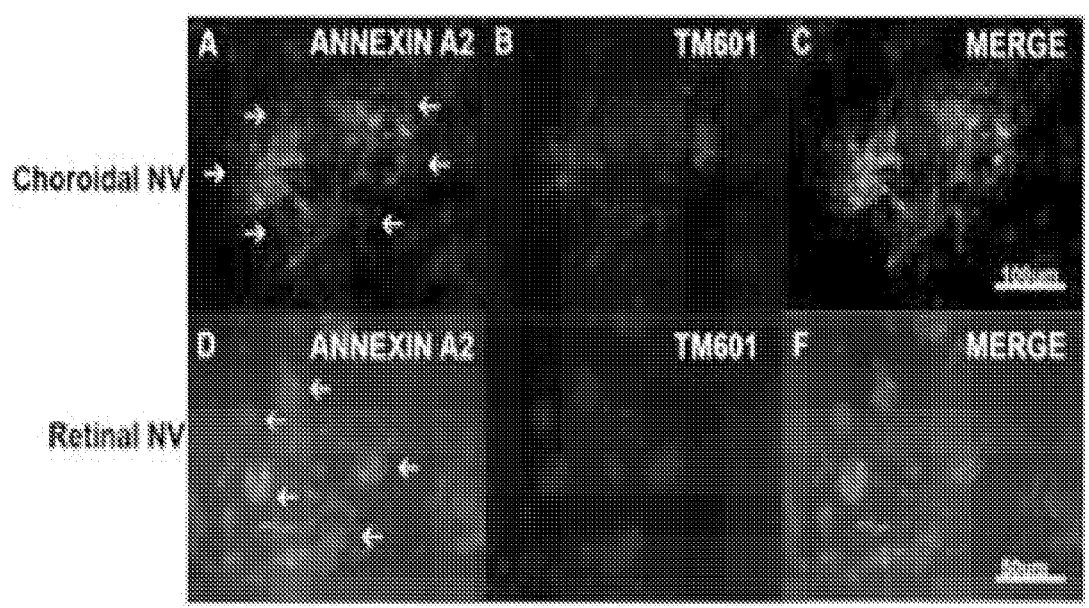

FIG. 25 depicts results from experiments showing co-localization of TM-601 and Annexin A2 in neovasculature in choroid (induced by laser rupture of Bruch's membrane) and in neovasculature in retina (induced by oxygen-induced ischemia). The top row (Panels A, B, and C) depicts results from experiments in which choroidal neovascularization (Choroidal NV) was induced by laser disruption of Bruch's membrane. The bottom row (Panels D, F, and a middle panel) depicts results from experiments in which retinopathic neovascularization (Retinal NV) was induced by oxygen-induced ischemia. TM-601 was injected intraocularly and immunohistochemistry was subsequently performed on tissue sections using anti-TM-601 antibody (Panel B and the middle panel of the bottom row) and anti-Annexin A2 antibody (Panels A and D). Merged results are depicted for Choroidal NV and Retinal NV in Panels C and F, respectively.

Figure 26:
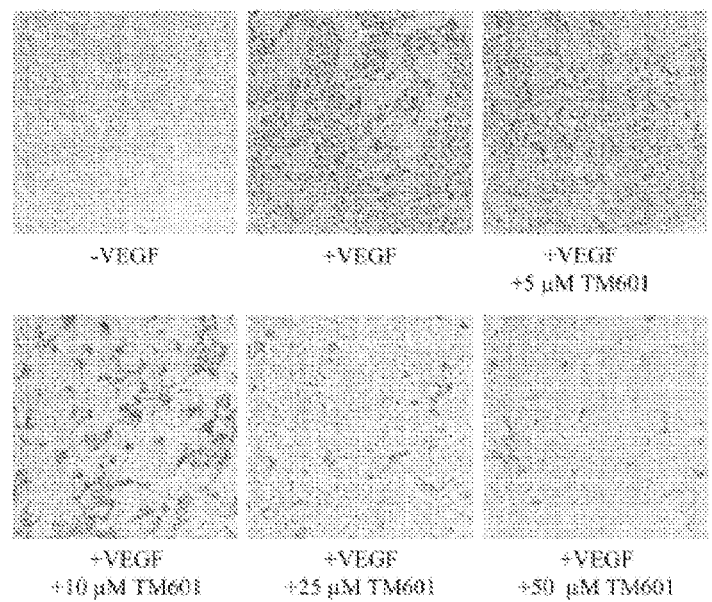
Figure 26:
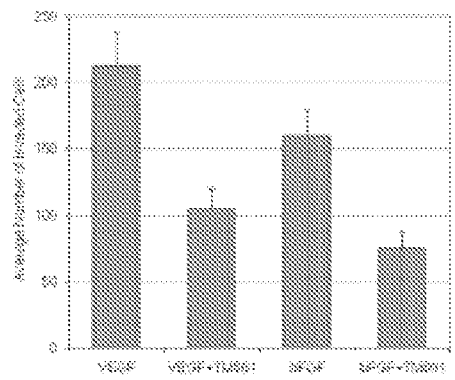
Figure 26:
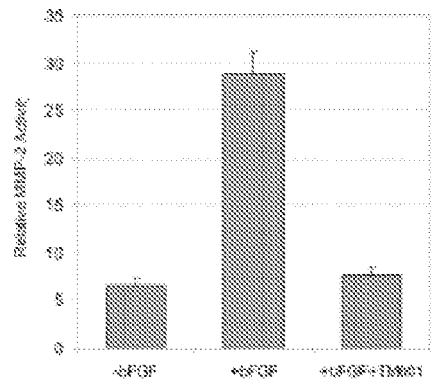

FIG. 26 depicts experimental results showing that TM-601 inhibits migration of HUVEC cells and decreases MMP-2 activity. (A) HUVEC cell migration was stimulated by 50 ng/ml VEGF. Addition of TM-601 inhibited migration (as assessed by invasion in a Transwell assay) in a dose-dependent manner. Invading cells were visualized on the lower surface of the Transwell using Giemsa stain. (B) Cell migration stimulated by either VEGF or bFGF (50 ng/ml) was calculated by visual cell count and TM-601 at 10 µM was shown to inhibit HUVEC invasion through the Transwell by approximately 50%. (C) MMP-2 activity in media taken from cultured HUVEC cells without treatment, treatment with bFGF, or treatment with bFGF together with 10 µM TM-601. Error bars indicate the standard error.

Figure 27:
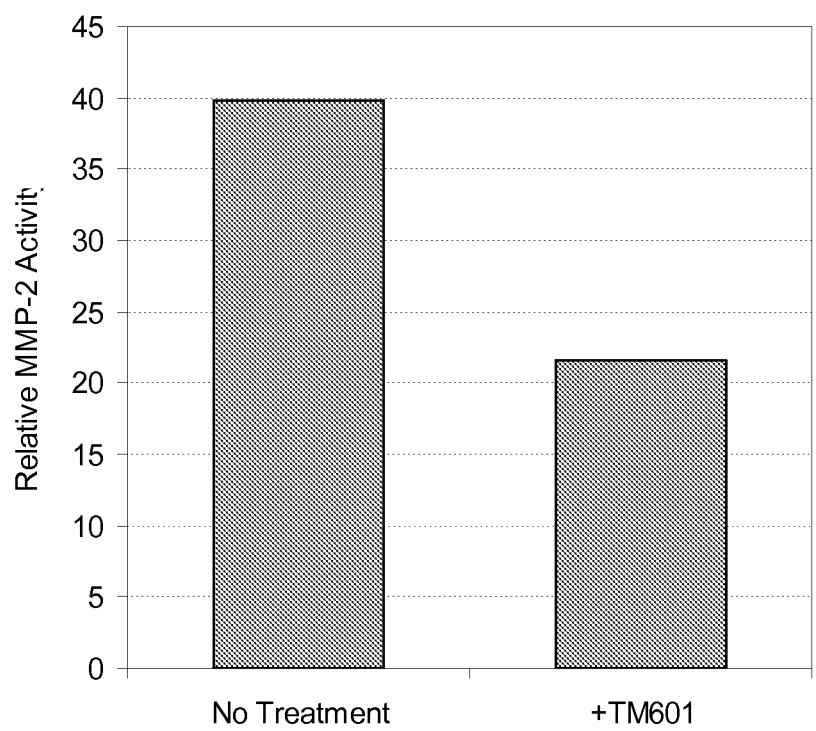

FIG. 27 depicts experimental results showing that TM-601 decreases MMP-2 activity secreted from U87 human glioma cells. MMP-2 activity was measured in media taken from cultured U87 cells without treatment, or with addition of 10 µM TM-601.

Figure 28:
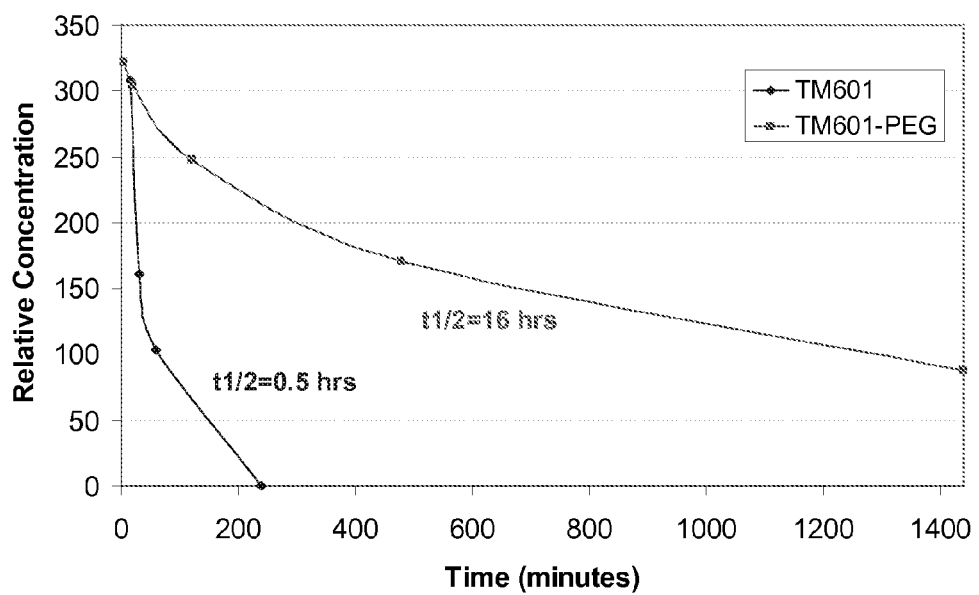

FIG. 28 shows the half-lives of PEGylated chlorotoxin (TM-601-PEG) as compared to unmodified TM-601 in intravenously injected non-cancerous mice. PEGylation increased the half-life of TM601 by approximately 32-fold.

Figure 29:
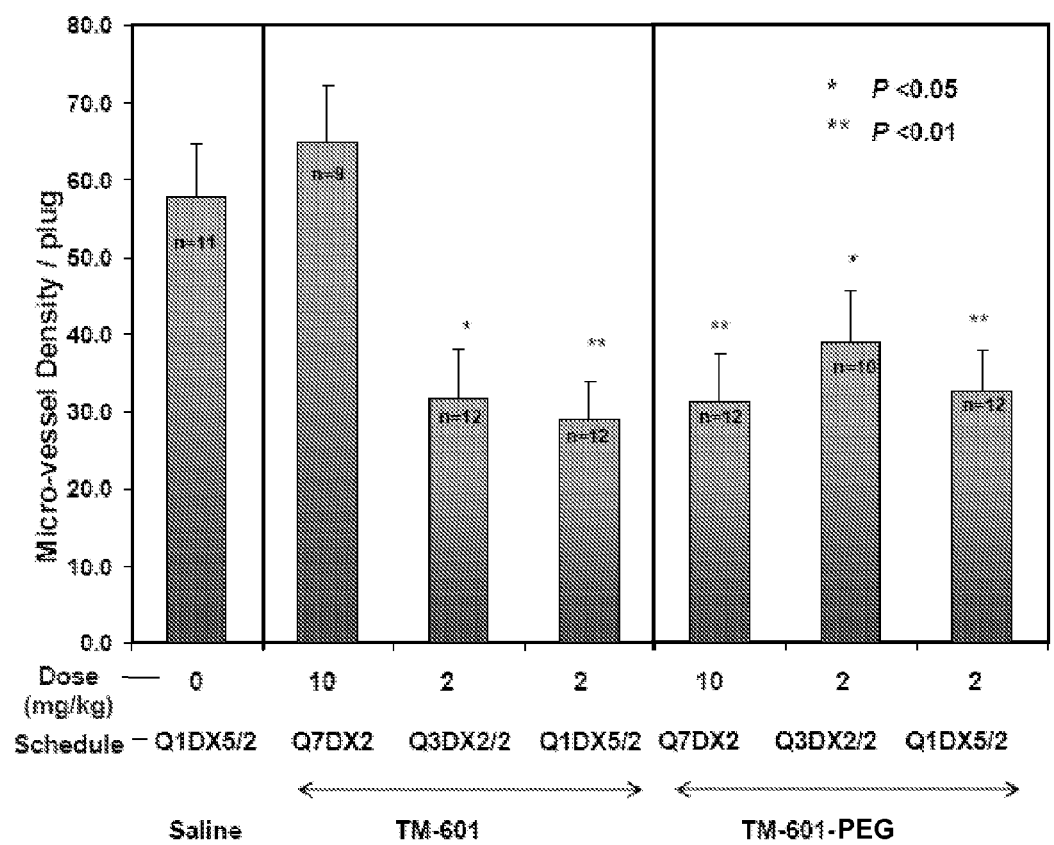

FIG. 29 shows that PEGylated TM-601 can achieve anti-angiogenic effects with less frequent dosing than unmodified TM-601 in a mouse CNV model. Microvessel density in a CNV model was plotted for various dosing regimens for unmodified TM-601 or for PEGylated TM-601.

DEFINITIONS

Throughout the specification, several terms are employed that are defined in the following paragraphs.

As used herein, the terms "about" and "approximately," in reference to a number, is used herein to include numbers that fall within a range of 20%, 10%, 5%, or 1% in either direction (greater than or less than) the number unless otherwise stated or otherwise evident from the context (except where such number would exceed 100% of a possible value).

As used herein, the term "Annexin A2" refers to a protein product of the gene whose official symbol is ANXA2 (in *Homo sapiens*) and whose official full name is "annexin A2" in the Entrez Gene listing at http://www.ncbi.nlm.nih.gov. (A variety of sequences for ANXA2 transcripts can be found, for example, under GenBank accession nos. M62899, NM_001002857, NM_001002858, NM_004039.) Annexin A2 is also known, among other things as "annexin II," and lipocortin 2.

The term "biologically active", when used herein to characterize a polypeptide, refers to a molecule that shares sufficient amino acid sequence homology with a parent polypeptide to exhibit similar or identical properties than the polypeptide (e.g., ability to specifically bind to cancer cells and/or to be internalized into cancer cells and/or to kill cancer cells).

As used herein, the term "cancer" refers to or describes the physiological condition in mammals that is typically characterized by unregulated cell growth. Examples of cancers include, but are not limited to carcinoma, lymphoma, blastoma, sarcoma, and leukemia. More particularly, examples of such cancers include lung cancer, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma.

As used herein, the term "cancer cell" refers to a cell in a mammal (e.g., a human being) in vivo which undergoes undesired and unregulated cell growth or abnormal persistence or abnormal invasion of tissues. In vitro, this term also refers to a cell line that is a permanently immortalized established cell culture that will proliferate indefinitely and in an unregulated manner given appropriate fresh medium and space.

As used herein, the term "cancer patient" can refer to an individual suffering from or susceptible to cancer. A cancer patient may or may not have been diagnosed with cancer. The term also includes individuals that have previously undergone therapy for cancer.

The terms "chemotherapeutics" and "anti-cancer agents or drugs" are used herein interchangeably. They refer to those medications that are used to treat cancer or cancerous conditions. Anti-cancer drugs are conventionally classified in one of the following group: alkylating agents, purine antagonists, pyrimidine antagonists, plant alkaloids, intercalating antibiotics, aromatase inhibitors, anti-metabolites, mitotic inhibitors, growth factor inhibitors, cell cycle inhibitors, enzymes, topoisomerase inhibitors, biological response modifiers, anti-hormones and anti-androgens. Examples of such anti-cancer agents include, but are not limited to, BCNU, cisplatin, gemcitabine, hydroxyurea, paclitaxel, temozolomide, topotecan, fluorouracil, vincristine, vinblastine, procarbazine, decarbazine, altretamine, methotrexate, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomycin, tamoxifen, flutamide, leuprolide, goserelin, aminogluthimide, anastrozole, amsacrine, asparaginase, mitoxantrone, mitotane and amifostine.

The term "combination therapy", as used herein, refers to those situations in which two or more different pharmaceutical agents are administered in overlapping regimens so that the subject is simultaneously exposed to both agents.

As used herein, the abbreviation "CTCAE" refers to Common Terminology Criteria for Adverse Events, a scale developed by the National Cancer Institutes for adverse event (AE) description and grading that is commonly used in clinical trials.

The term "cytotoxic", when used herein to characterize a moiety, compound, drug or agent refers to a moiety, compound, drug or agent that inhibits or prevents the function of cells and/or causes destruction of cells.

A "dosing regimen", as that term is used herein, refers to a set of unit doses (typically more than one) that are administered individually separated by periods of time. The recommended set of doses (i.e., amounts, timing, route of administration, etc.) for a particular pharmaceutical agent constitutes its dosing regimen.

As used herein, the terms "effective amount" and "effective dose" refer to any amount or dose of a compound or composition that is sufficient to fulfill its intended purpose(s), i.e., a desired biological or medicinal response in a tissue or subject at an acceptable benefit/risk ratio. For example, in certain embodiments of the present invention, the purpose(s) may be: to specifically bind to a target tissue, to slow down or stop the progression, aggravation, or deterioration of the symptoms of a cancer, to bring about amelioration of the symptoms of the cancer, and/or to cure the cancer. The relevant intended purpose may be objective (i.e., measurable by some test or marker) or subjective (i.e., subject gives an indication of or feels an effect). A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. In some embodiments, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts.

As used herein, terms "fluorophore", "fluorescent moiety", "fluorescent label", "fluorescent dye" and "fluorescent labeling moiety" are used herein interchangeably. They refer to a molecule that, in solution and upon excitation with light of appropriate wavelength, emits light back. Numerous fluorescent dyes of a wide variety of structures and characteristics are suitable for use in the practice of this invention. Similarly, methods and materials are known for fluorescently labeling nucleic acids (see, for example, R. P. Haugland, "*Molecular Probes: Handbook of Fluorescent Probes and Research Chemicals* 1992-1994", $5^{th}$ Ed., 1994, Molecular Probes, Inc.). In choosing a fluorophore, it is often desirable that the fluorescent molecule absorbs light and emits fluorescence with high efficiency (i.e., high molar absorption coefficient and fluorescence quantum yield, respectively) and is photostable (i.e., it does not undergo significant degradation upon light excitation within the time necessary to perform the analysis).

As used herein, the term "fusion protein" refers to a molecule comprising two or more proteins or fragments thereof linked by a covalent bond via their individual peptide backbones, most preferably generated through genetic expression of a polynucleotide molecule encoding those proteins.

As used herein, the term "homologous" (or "homology") refers to a degree of identity between two polypeptide molecules or between two nucleic acid molecules. When a position in both compared sequences is occupied by the same base or amino acid monomer subunit, then the respective molecules are homologous at that position. The percentage of homology between two sequences corresponds to the number of matching or homologous positions shared by the two sequences divided by the number of positions compared and multiplied by 100. Generally, a comparison is made when two sequences are aligned to give maximum homology. Homologous amino acid sequences share identical or similar amino acid residues. Similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g., that have a similar size, shape, electric charge, chemical properties, including the ability to form covalent or hydrogen bonds, or the like. In some embodiments, conservative substitutions utilized in accordance with the present invention are those fulfilling the criteria defined for an "accepted point mutation" by Dayhoff et al. ("Atlas of Protein Sequence and Structure", 1978, Nat. Biomed. Res. Foundation, Washington, D.C., Suppl. 3, 22: 354-352).

The terms "individual" and "subject" are used herein interchangeably. They refer to a human or another mammal (e.g., mouse, rat, rabbit, dog, cat, cattle, swine, sheep, horse or primate) that can be afflicted with or is susceptible to a disease or disorder (e.g., cancer) but may or may not have the disease or disorder. In many embodiments, the subject is a human being. In many embodiments, the subject is a patient. Unless otherwise stated, the terms "individual" and "subject" do not denote a particular age, and thus encompass adults, children, and newborns.

As used herein, the term "inhibit" means to prevent something from happening, to delay occurrence of something happening, and/or to reduce the extent or likelihood of something happening. Thus, "inhibiting metastases" and "inhibiting the formation of metastases" is intended to encompass preventing, delaying, and/or reducing the likelihood of occurrence of metastases as well as reducing the number, growth rate, size, etc., of metastases.

As used herein, the term "initiation" when applied to a dosing regimen can be used to refer to a first administration of a pharmaceutical agent to a subject who has not previously received the pharmaceutical agent. Alternatively or additionally, the term "initiation" can be used to refer to administration of a particular unit dose of a pharmaceutical agent during therapy of a patient.

The terms "labeled" and "labeled with a detectable agent or moiety" are used herein interchangeably to specify that an entity (e.g., a chlorotoxin or chlorotoxin conjugate) can be visualized, for example following binding to another entity (e.g., a neoplastic tumor tissue). Preferably the detectable agent or moiety is selected such that it generates a signal which can be measured and whose intensity is related to (e.g., proportional to) the amount of bound entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionuclides, fluorophores, chemiluminescent agents, microparticles, enzymes, colorimetric labels, magnetic labels, haptens, Molecular Beacons, aptamer beacons, and the like.

As used herein, the term "metastasis" (sometimes abbreviated as "mets;" plural "metastases") refers to the spread of tumor cells from one organ or tissue to another location. The term also refers to tumor tissue that forms in a new location as a result of metastasis. A "metastatic cancer" is a cancer that spreads from its original, or primary, location, and may also be referred to as a "secondary cancer" or "secondary tumor." Generally, metastastic tumors are named for the tissue of the primary tumor from which they originate. Thus, a breast cancer that has metastasized to the lung may be referred to as "metastatic breast cancer" even though some cancer cells are located in the lung.

As used herein, the term "neovasculature" refers to newly formed blood vessels that have not yet fully matured, i.e., do not have a fully formed endothelial lining with tight cellular junctions or a complete layer of surrounding smooth muscle cells. As used herein, the term "neovessel" is used to refer to a blood vessel in neovasculature.

The terms "normal" and "healthy" are used herein interchangeably. They refer to an individual or group of individuals who do not have a tumor. The term "normal" is also used herein to qualify a tissue sample isolated from a healthy individual.

The terms "pharmaceutical agent", "therapeutic agent" and "drug" are used herein interchangeably. They refer to a substance, molecule, compound, agent, factor or composition effective in the treatment, inhibition, and/or detection of a disease, disorder, or clinical condition.

A "pharmaceutical composition" is herein defined as a composition that comprises an effective amount of at least one active ingredient (e.g., a chlorotoxin or chlorotoxin conjugate that may or may not be labeled), and at least one pharmaceutically acceptable carrier.

As used herein, the term "pharmaceutically acceptable carrier" refers to a carrier medium which does not interfere with the effectiveness of the biological activity of the active ingredient(s) and which is not excessively toxic to the host at the concentration at which it is administered. The term includes solvents, dispersion media, coatings, antibacterial and antifungal agents, isotonic agents, absorption delaying agents, and the like. The use of such media and agents for pharmaceutically active substances is well known in the art (see for example, "*Remington's Pharmaceutical Sciences*", E. W. Martin, 18$^{th}$ Ed., 1990, Mack Publishing Co.: Easton, Pa., which is incorporated herein by reference in its entirety).

As used herein, the term "primary tumor" refers to a tumor that is at the original site where the tumor first arose, i.e., as opposed to having spread there.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative slicing or limited proteolysis), or in the alternative, may arise from differential post-translational modification (e.g., glycosylation, acylation or phosphorylation).

The term "protein analog", as used herein, refers to a polypeptide that possesses a similar or identical function as a parent polypeptide but need not necessarily comprise an amino acid sequence that is similar or identical to the amino acid sequence of the parent polypeptide, or possess a structure that is similar or identical to that of the parent polypeptide. Preferably, in the context of the present invention, a protein analog has an amino acid sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of the parent polypeptide. Moreover, those of ordinary skill in the art will understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90%, 96%, 97%, 98% or 99% in one or more highly conserved regions usually encompassing at least 3-4 and often up to 20 or more amino acids, with the parent polypeptide, is encompassed in the term "protein analog).

As used herein, the term "protein fragment" refers to a polypeptide comprising an amino acid sequence of at least 5 amino acid residues of the amino acid sequence of a second polypeptide. A fragment of a protein may or may not possess a functional activity of the parent polypeptide.

The term "regress," when used to refer to blood vessels and/or vasculature (including neovasculature and/or neovessels), is used herein to mean to retract, shrink, etc.

As used herein, the term "small molecule" includes any chemical or other moiety that can act to affect biological processes. Small molecules can include any number of therapeutic agents presently known and used, or can be small molecules synthesized in a library of such molecules for the purpose of screening for biological function(s). Small molecules are distinguished from macromolecules by size. Small molecules suitable for use in the present invention usually have molecular weight less than about 5,000 daltons (Da), preferably less than about 2,500 Da, more preferably less than 1,000 Da, most preferably less than about 500 Da.

As used herein, the term "susceptible" means having an increased risk for and/or a propensity for (typically based on genetic predisposition, environmental factors, personal history, or combinations thereof) something, i.e., a disease, disorder, or condition such as metastatic cancer, than is observed in the general population. The term takes into account that an individual "susceptible" for a condition may never be diagnosed with the condition.

As used herein, the term "systemic administration" refers to administration of an agent such that the agent becomes widely distributed in the body in significant amounts and has a biological effect, e.g., its desired effect, in the blood and/or reaches its desired site of action via the vascular system. Typical systemic routes of administration include administration by (1) introducing the agent directly into the vascular system or (2) oral, pulmonary, or intramuscular administration wherein the agent is adsorbed, enters the vascular system, and is carried to one or more desired site(s) of action via the blood.

The term "tissue" is used herein in its broadest sense. A tissue may be any biological entity that can (but does not necessarily) comprise a tumor cell. In the context of the present invention, in vitro, in vivo and ex vivo tissues are considered. Thus, a tissue may be part of an individual or may be obtained from an individual (e.g., by biopsy). Tissues may also include sections of tissue such as frozen sections taken for histological purposes or archival samples with known diagnosis, treatment and/or outcome history. The term tissue also encompasses any material derived by processing the tissue sample. Derived materials include, but are not limited to, cells (or their progeny) isolated from the tissue. Processing of the tissue sample may involve one or more of: filtration, distillation, extraction, concentration, inactivation of interfering components, addition of reagents, and the like.

The term "treatment" is used herein to characterize a method or process that is aimed at (1) delaying or preventing the onset of a disease, disorder, or condition; (2) slowing down or stopping the progression, aggravation, or deterioration of one or more symptoms of the disease, disorder, or condition; (3) bringing about ameliorations of the symptoms of the disease, disorder, or condition; (4) reducing the severity or incidence of the disease, disorder, or condition; or (5) curing the disease, disorder., or condition. A treatment may be administered prior to the onset of the disease, disorder, or condition, for a prophylactic or preventive action. Alternatively or additionally, the treatment may be administered after initiation of the disease, disorder, or condition, for a therapeutic action.

DETAILED DESCRIPTION OF CERTAIN EMBODIMENTS

As already mentioned above, the present invention is directed to methods for the treatment and/or detection of tumor metastases. Methods provided herein generally comprise administration of a chlorotoxin agent that may or may not be labeled with a detectable moiety. In certain embodiments, the chlorotoxin agent binds to tumor metastases. In certain embodiments, the chlorotoxin agent inhibits and/or reduces the likelihood of formation of new metastases. In certain embodiments, the chlorotoxin agent is administered systemically (e.g., intravenously) and/or the chlorotoxin agent crosses the blood/brain barrier. Thus, in some embodiments, the invention provides methods of treating, inhibiting, and/or detecting metastases located in the brain. In certain embodiments, the formation of new blood vessels is inhibited and/or existing neovasculature regresses.

In accordance with the present invention there may be employed conventional molecular biology, microbiology, and recombinant DNA techniques within the skill of the art. Such techniques are explained fully in the literature. See, e.g., Maniatis, Fritsch & Sambrook, "*Molecular Cloning: A Laboratory Manual*", 1982; "*DNA Cloning: A Practical Approach*," Volumes I and II, D. N. Glover (Ed.), 1985; "*Oligonucleotide Synthesis*", M. J. Gait (Ed.), 1984; "*Nucleic Acid Hybridization*", B. D. Hames & S. J. Higgins (Eds.), 1985; "*Transcription and Translation*" B. D. Hames & S. J. Higgins (Eds.), 1984; "*Animal Cell Culture*", R. I. Freshney (Ed.), 1986; "*Immobilized Cells And Enzymes*", IRL Press, 1986; B. Perbal, "*A Practical Guide To Molecular Cloning*", 1984.

I. Chlorotoxin Agents

Methods of treatment and/or detection of the present invention involve administering, to an individual in need thereof (such as, for an example, an individual who has, has had, is at risk of developing, and/or susceptible to at least one metastasis), an effective dose of at least one chlorotoxin agent such that the chlorotoxin agent binds to the at least one metastasis. As used herein, the term "chlorotoxin agent" refers to a compound that comprises at least one chlorotoxin moiety. In certain embodiments, a chlorotoxin agent comprises at least one chlorotoxin moiety associated with at least one therapeutic moiety (e.g., an anti-cancer agent). The chlorotoxin moiety (and/or therapeutic moiety) may be associated with at least one labeling moiety.

A. Chlorotoxin Moieties

As used herein, the term "chlorotoxin moiety" refers to a chlorotoxin, a biologically active chlorotoxin subunit or a chlorotoxin derivative.

In certain embodiments, the term "chlorotoxin" refers to the full-length, 36 amino acid polypeptide naturally derived from *Leiurus quinquestriatus* scorpion venom (DeBin et al., Am. J. Physiol., 1993, 264: C361-369), which comprises the amino acid sequence of native chlorotoxin as set forth in SEQ ID NO. 1 of International Application No. WO 2003/101474, the contents of which are incorporated herein by reference. The term "chlorotoxin" includes polypeptides comprising SEQ ID NO. 1 which have been synthetically or recombinantly produced, such as those disclosed in U.S. Pat. No. 6,319,891 (which is incorporated herein by reference in its entirety).

A "biologically active chlorotoxin subunit" is a peptide comprising less than the 36 amino acids of chlorotoxin and which retains at least one property or function of chlorotoxin. As used herein, a "property or function" of chlorotoxin includes, but is not limited to, the ability to arrest abnormal cell growth; ability to specifically bind to a tumor/cancer cell compared to a normal cell; ability to specifically bind to a metastasizing tumor/cancer cell or a tumor/cancer cell in a metastasis compared to a normal cell; ability to be internalized into a tumor/cancer cell; ability to kill a tumor/cancer cell; and/or ability to suppress formation of and/or cause regression of neovessels. The tumor/cancer cell may be in vitro, ex vivo, in vitro, part of a metastasis, a primary isolate from a subject, a cultured cell, or a cell line.

As used herein, the term "biologically active chlorotoxin derivative" refers to any of a wide variety of derivatives, analogs, variants, polypeptide fragments and mimetics of chlorotoxin and related peptides which retain at least one property or function of chlorotoxin (as described above). Examples of chlorotoxin derivatives include, but are not limited to, peptide variants of chlorotoxin, peptide fragments of chlorotoxin, for example, fragments comprising or consisting of contiguous 10-mer peptides of SEQ ID No. 1, 2, 3, 4, 5, 6, or 7 as set forth in International Application No. WO 2003/101474 or comprising residues 10-18 or 21-30 of SEQ ID No. 1 as set forth in International Application No. WO 2003/101474, core binding sequences, and peptide mimetics.

Examples of chlorotoxin derivatives include peptides having a fragment of the amino acid sequence set forth in SEQ ID No. 1 of International Application No. WO 2003/101474, having at least about 7, about 8, about 9, about 10, about 15, about 20, about 25, about 30 or about 35 contiguous amino acid residues, associated with the activity of chlorotoxin. Such fragments may contain functional regions of the chlorotoxin peptide, identified as regions of the amino acid sequence that correspond to known peptide domains, as well as regions of pronounced hydrophilicity. Such fragments may also include two core sequences linked to one another, in any order, with intervening amino acid removed or replaced by a linker.

Derivatives of chlorotoxin include polypeptides comprising a conservative or non-conservative substitution of at least one amino acid residue when the derivative sequence and the chlorotoxin sequence are maximally aligned. The substitution may be one that enhances at least one property or function of chlorotoxin, inhibits at least one property or function of chlorotoxin, or is neutral to at least one property or function of chlorotoxin.

Examples of derivatives of chlorotoxin suitable for use in the practice of the present invention are described in International Application No. WO 2003/101474 (which is incorporated herein by reference in its entirety). Particular examples include polypeptides that comprise or consist of SEQ ID NO. 8 or SEQ ID NO. 13 as set forth in this International Application, as well as variants, analogs, and derivatives thereof.

Other examples of chlorotoxin derivatives include those polypeptides containing predetermined mutations by, e.g., homologous recombination, site-directed or PCR mutagenesis, and the alleles or other naturally-occurring variants of the family of peptides; and derivatives wherein the peptide has been covalently modified by substitution, chemical, enzymatic or other appropriate means with a moiety other than a naturally-occurring amino acid (for example a detectable moiety such as enzyme or a radioisotope).

Chlorotoxin and peptide derivatives thereof can be prepared using any of a wide variety of methods, including standard solid phase (or solution phase) peptide synthesis methods, as is known in the art. In addition, the nucleic acids encoding these peptides may be synthesized using commercially available oligonucleotide synthesis instrumentation and the proteins may be produced recombinantly using standard recombinant production systems.

Other suitable chlorotoxin derivatives include peptide mimetics that mimic the three-dimensional structure of chlorotoxin. Such peptide mimetics may have significant advantages over naturally occurring peptides including, for example, more economical production, greater chemical stability, enhanced pharmacological properties (half-life, absorption, potency, efficacy, etc), altered specificity (e.g., broad-spectrum biological activities, reduced antigenicity and others).

In certain embodiments, mimetics are molecules that mimic elements of chlorotoxin peptide secondary structure. Peptide backbone of proteins exists mainly to orient amino acid side chains in such a way as to facilitate molecular interactions, such as those of antibody and antigen. A peptide mimetic is expected to permit molecular interactions similar to the natural molecule. Peptide analogs are commonly used in the pharmaceutical industry as non-peptide drugs with properties analogous to those of the template peptide. These types of compounds are also referred to as peptide mimetics or peptidomimetics (see, for example, Fauchere, Adv. Drug Res., 1986, 15: 29-69; Veber & Freidinger, 1985, Trends Neurosci., 1985, 8: 392-396; Evans et al., J. Med. Chem., 1987, 30: 1229-1239) and are usually developed with the aid of computerized molecular modeling.

Generally, peptide mimetics are structurally similar to a paradigm polypeptide (i.e., a polypeptide that has a biochemical property or pharmacological activity), but have one or more peptide linkages optionally replaced by a non-peptide linkage. The use of peptide mimetics can be enhanced through the use of combinatorial chemistry to create drug libraries. The design of peptide mimetics can be aided by identifying amino acid mutations that increase or decrease the binding of a peptide to, for example, a tumor cell. Approaches that can be used include the yeast two hybrid method (see, for example, Chien et al., Proc. Natl. Acad. Sci. USA, 1991, 88: 9578-9582) and using the phase display method. The two-hybrid method detects protein-protein interactions in yeast (Field et al., Nature, 1989, 340: 245-246). The phage display method detects the interaction between an immobilized protein and a protein that is expressed on the surface of phages such as lambda and M13 (Amberg et al., Strategies, 1993, 6: 2-4; Hogrefe et al., Gene, 1993, 128: 119-126). These methods allow positive and negative selection of peptide-protein interactions and the identification of the sequences that determine these interactions.

In certain embodiments, a chlorotoxin agent comprises a polypeptide toxin of another scorpion species that displays similar or related activity to chlorotoxin described above. As used herein, the term "similar or related activity to chlorotoxin" refers, in particular, to the selective/specific binding to tumor/cancer cells. Examples of suitable related scorpion toxins include, but are not limited to toxins or related peptides of scorpion origin that display amino acid and/or nucleotide sequence identity to chlorotoxin. Examples of related scorpion toxins include, but are not limited to, CT neurotoxin from *Mesobuthus martenssi* (GenBank Accession No. AAD473730), Neurotoxin BmK 41-2 from *Buthus martensii* karsch (GenBank Accession No. A59356), Neurotoxin Bm12-b from *Buthus martensii* (GenBank Accession No. AAK16444), Probable Toxin LGH 8/6 from *Leiurus quinquestriatus hebraeu* (GenBank Accession No. P55966), and Small toxin from *Mesubutus tamulus sindicus* (GenBank Accession No. P15229).

Related scorpion toxins suitable for use in the present invention comprise polypeptides that have an amino acid sequence of at least about 75%, at least about 85%, at least about 90%, at least about 95%, or at least about 99% sequence identity with the entire chlorotoxin sequence as set forth in SEQ ID No. 1 of International Application No. WO 2003/101474 (which is incorporated herein by reference in its entirety). In certain embodiments, related scorpion toxins include those scorpion toxins that have a sequence homologous to SEQ ID NO. 8 or SEQ ID NO. 13 of chlorotoxin, as set forth in International Application No. WO 2003/101474.

In certain embodiments, a chlorotoxin moiety within a chlorotoxin agent is labeled. Examples of labeling methods and labeling moieties are described below.

B. Therapeutic Moieties

As already mentioned above, in certain embodiments, a chlorotoxin agent comprises at least one chlorotoxin moiety associated with at least one therapeutic moiety. Suitable therapeutic moieties include any of a large variety of substances, molecules, compounds, agents or factors that are effective in the treatment of a disease or clinical condition. In certain embodiments, a therapeutic moiety is a chemotherapeutic (i.e., an anti-cancer drug). Suitable anti-cancer drugs include any of a large variety of substances, molecules, compounds, agents or factors that are directly or indirectly toxic or detrimental to cancer cells.

As will be appreciated by one of ordinary skill in the art, a therapeutic moiety may be a synthetic or natural compound: a single molecule, a mixture of different molecules or a complex of different molecules. Suitable therapeutic moieties can belong to any of a variety of classes of compounds including, but not limited to, small molecules, peptides, proteins, saccharides, steroids, antibodies (including fragments and variants thereof), fusion proteins, antisense polynucleotides, ribozymes, small interfering RNAs, peptidomimetics, radionuclides, and the like.

When a therapeutic moiety comprises an anti-cancer drug, the anti-cancer drug can be found, for example, among the following classes of anti-cancer drugs: alkylating agents, anti-metabolic drugs, anti-mitotic antibiotics, alkaloidal anti-tumor agents, hormones and anti-hormones, interferons, non-steroidal anti-inflammatory drugs, and various other anti-tumor agents such as kinase inhibitors, proteasome inhibitors and NF-κB inhibitors.

Examples of anti-cancer drugs include, but are not limited to, alkylating drugs (e.g., mechlorethamine, chlorambucil, cyclophosphamide, melphalan, ifosfamide, temozolomide, etc.), antimetabolites (e.g., methotrexate, etc.), purine antagonists and pyrimidine antagonists (e.g., 6-mercaptopurine, 5-fluorouracil, cytraribine, gemcitabine, etc.), spindle poisons (e.g., vinblastine, vincristine, vinorelbine, paclitaxel, etc.), podophyllotoxins (e.g., etoposide, irinotecan, topotecan, etc.), antibiotics (e.g., doxorubicin, bleomycin, mitomycin, etc.), nitrosureas (e.g., carmustine, lomustine, nomustine, etc.), inorganic ions (e.g., cisplatin, carboplatin, etc.), enzymes (e.g., asparaginase, etc.), and hormones (e.g., tamoxifen, leuprolide, flutamide, megestrol, etc.), to name a few. For a more comprehensive discussion of updated cancer therapies see, http://www.cancer.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Some anti-cancer drugs act by arresting the growth and/or replication of cancer cells. Such drugs are generally classified as "cytostatic." In certain embodiments, a therapeutic moiety comprises a cytostatic agent. Examples of cytostatic agents include alkylating agents, anti-metabolites, plant alkyloids and terpenoids (including *vinca* alkaloids, podophyllotoxin, taxanes, etc.; VP-16 is an example of a plant alkaloid), topoisomerase inhibitors, antitumor antibodies, hormones, etc.

In certain embodiments, a therapeutic moiety comprises a cytotoxic agent. Examples of cytotoxic agents include toxins, other bioactive proteins, conventional chemotherapeutic agents, enzymes, and radioisotopes.

Examples of suitable cytotoxic toxins include, but are not limited to, bacterial and plant toxins such as gelonin, ricin, saponin, *Pseudomonas* exotoxin, pokeweed antiviral protein, diphtheria toxin, etc.

Examples of suitable cytotoxic bioactive proteins include, but are not limited to, proteins of the complement system (or complement proteins). The complement system is a complex biochemical cascade that helps clear pathogens from an organism, and promotes healing (B. P. Morgan, Crit. Rev. Clin. Lab. Sci., 1995, 32: 265). The complement system consists of more than 35 soluble and cell-bound proteins, 12 of which are directly involved in the complement pathways.

Examples of suitable cytotoxic chemotherapeutic agents include, but are not limited to, taxanes (e.g., docetaxel, paclitaxel, etc.), maytansines, duocarmycins, CC-1065, auristatins, calicheamincins and other enediyne anti-tumor antibiotics. Other examples include the anti-folates (e.g., aminopterin, methotrexate, pemetrexed, raltitrexed, etc.), *vinca* alkaloids (e.g., vincristine, vinblastine, etoposide, vindesine, vinorelbine, etc.), and anthracyclines (e.g., daunorubicin, doxorubicin, epirubicin, idarubicin, mitoxantrone, valrubicin, etc.).

Examples of suitable cytotoxic enzymes include, but are not limited to, nucleolytic enzymes.

Examples of suitable cytotoxic radioisotopes include any α-, β- or γ-emitter which, when localized at a tumor site, results in cell destruction (S.E. Order, "*Analysis, Results, and Future Prospective of the Therapeutic Use of Radiolabeled Antibody in Cancer Therapy*", Monoclonal Antibodies for Cancer Detection and Therapy, R. W. Baldwin et al. (Eds.), Academic Press, 1985). Examples of such radioisotopes include, but are not limited to, iodine-131 ($^{131}$I), iodine-125 ($^{125}$I), bismuth-212 ($^{212}$Bi), bismuth-213 ($^{213}$Bi), astatine-211 ($^{211}$At), rhenium-186 ($^{186}$Re), rhenium-186 ($^{188}$Re), phosphorus-32 ($^{32}$P), yttrium-90 ($^{90}$Y), samarium-153 ($^{153}$Sm), and lutetium-177 ($^{117}$Lu).

Alternatively or additionally, therapeutic moieties suitable for use in the present invention may be any of the therapeutic moieties described in co-owned provisional applications entitled "Chlorotoxins as Drug Carriers" (U.S. Ser. No. 60/954,409) filed on Aug. 7, 2007 and "Systemic Administration of Chlorotoxin Agents for the Diagnosis and Treatment of Tumors" (U.S. Ser. No. 60/) filed on Oct. 12, 2007, the entire contents of which are incorporated herein by reference in their entirety. Examples of classes of such therapeutic moieties include, but are not limited to, poorly water soluble anti-cancer agents, anti-cancer agents associated with drug resistance, antisense nucleic acids, ribozymes, triplex agents, short-interfering RNAs (siRNAs), photosensitizers, radiosensitizers, superantigens, prodrug activating enzymes, and anti-angiogenic agents.

In certain embodiments, a therapeutic (e.g., anti-cancer) agent within a chlorotoxin agent is a nucleic acid agent.

Numerous cancers and tumors have been shown to be associated with varying degrees of genetic impairment, such as point mutations, gene deletions, or duplications. Many new strategies for the treatment of cancer, such as "antisense", "antigene", and "RNA interference" have been developed to modulate the expression of genes (A. Kalota et al., Cancer Biol. Ther., 2004, 3: 4-12; Y. Nakata et al., Crit. Rev. Eukaryot. Gene Expr., 2005, 15: 163-182; V. Wacheck and U. Zangmeister-Wittke, Crit. Rev. Oncol. Hematol., 2006, 59: 65-73; A. Kolata et al., Handb. Exp. Pharmacol., 2006, 173: 173-196). These approaches utilize, for example, antisense nucleic acids, ribozymes, triplex agents, or short interfering RNAs (siRNAs) to block the transcription or translation of a specific mRNA or DNA of a target gene, either by masking that mRNA with an antisense nucleic acid or DNA with a triplex agent, by cleaving the nucleotide sequence with a ribozyme, or by destruction of the mRNA, through a complex mechanism involved in RNA-interference. In all of these strategies, mainly oligonucleotides are used as active agents, although small molecules and other structures have also been applied. While the oligonucleotide-based strategies for modulating gene expression have a huge potential for the treatment of some cancers, pharmacological applications of oligonucleotides have been hindered mainly by the ineffective delivery of these compounds to their sites of action within cancer cells. (P. Herdewijn et al., Antisense Nucleic Acids Drug Dev., 2000, 10: 297-310; Y. Shoji and H. Nakashima, Curr. Charm. Des., 2004, 10: 785-796; A. W Tong et al., Curr. Opin. Mol. Ther., 2005, 7: 114-124).

Chlorotoxin agents are provided herein that comprise a toxin moiety (e.g., chlorotoxin moiety) and a nucleic acid molecule that is useful as a therapeutic (e.g., anti-cancer) agent. A variety of chemical types and structural forms of nucleic acid can be suitable for such strategies. These include, by way of non-limiting example, DNA, including single-stranded (ssDNA) and double-stranded (dsDNA); RNA, including, but not limited to ssRNA, dsRNA, tRNA, mRNA, rRNA, enzymatic RNA; RNA:DNA hybrids, triplexed DNA (e.g., dsDNA in association with a short oligonucleotide), and the like.

In some embodiments of the present invention, the nucleic acid agent present in a chlorotoxin agent is between about 5 and 2000 nucleotides long. In some embodiments, the nucleic acid agent is at least about 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50 or more nucleotides long. In some embodiments, the nucleic acid agent is less than about 2000, 1900, 1800, 1700, 1600, 1500, 1400, 1300, 1200, 1100, 1000, 900, 800, 700, 600, 500, 450, 400, 350, 300, 250, 200, 150, 100, 50, 45, 40, 35, 30, 25, 20 or fewer nucleotides long.

In some embodiments, a nucleic acid agent present in a chlorotoxin agent of the present invention comprises a promoter and/or other sequences that regulate transcription. In some embodiments, a nucleic acid agent present in a chlorotoxin agent of the present invention comprises an origin of replication and/or other sequences that regulate replication. In some embodiments, a nucleic acid agent present in a chlorotoxin agent of the present invention does not include a promoter and/or an origin of replication.

Nucleic acid anti-cancer agents suitable for use in the practice of the present invention include those agents that target genes associated with tumorigenesis and cell growth or cell transformation (e.g., proto-oncogenes, which code for proteins that stimulate cell division), angiogenic/anti-angiogenic genes, tumor suppressor genes (which code for proteins that suppress cell division), genes encoding proteins associated with tumor growth and/or tumor migration, and suicide genes which induce apoptosis or other forms of cell death, especially suicide genes that are most active in rapidly dividing cells.

Examples of gene sequences associated with tumorigenesis and/or cell transformation include MLL fusion genes, BCR-ABL, TEL-AML1, EWS-FLI1, TLS-FUS, PAX3-FKHR, Bcl-2, AML1-ETO, AML1-MTG8, Ras, Fos PDGF, RET, APC, NF-1, Rb, p53, MDM2 and the like; overexpressed sequences such as multidrug resistance genes; cyclins; beta-Catenin; telomerase genes; c-myc, n-myc, Bcl-2, Erb-B1 and Erb-B2; and mutated sequences such as Ras, Mos, Raf, and Met. Examples of tumor suppressor genes include, but are not limited to, p53, p21, RB1, WT1, NF1, VHL, APC, DAP kinase, p16, ARF, Neurofibromin, and PTEN. Examples of genes that can be targeted by nucleic acid molecules useful in anti-cancer therapy include genes encoding proteins associated with tumor migration such as integrins, selectins and metalloproteinases; anti-angiogenic genes encoding proteins that promote the formation of new vessels such as Vascular Endothelial Growth Factor (VEGF) or VEGFr; anti-angiogenic genes encoding proteins that inhibit neovascularization such as endostatin, angiostatin, and VEGF-R2; and genes encoding proteins such as interleukins, interferon, fibroblast growth factor ($\alpha$-FGF and $\beta$-FGF), insulin-like growth factor (e.g., IGF-1 and IGF-2), Platelet-derived growth factor (PDGF), tumor necrosis factor (TNF), Transforming Growth Factor (e.g., TGF-$\alpha$ and TGF-$\beta$), Epidermal growth factor (EGF), Keratinocyte Growth Factor (KGF), stem cell factor and its receptor c-Kit (SCF/c-Kit) ligand, CD40L/CD40, VLA-4 VCAM-1, ICAM-1/LFA-1, hyalurin/CD44, and the like. As will be recognized by one skilled in the art, the foregoing examples are not exclusive.

Nucleic acids in chlorotoxin agents of the present invention may have any of a variety of activities including, for example, as anti-cancer or other therapeutic agents, probes, primers, etc. Nucleic acids in chlorotoxin agents of the present invention may have enzymatic activity (e.g., ribozyme activity), gene expression inhibitory activity (e.g., as antisense or siRNA agents, etc), and/or other activities. Nucleic acids in chlorotoxin agents of the present invention may be active themselves or may be vectors that deliver active nucleic acid agents (e.g., through replication and/or transcription of a delivered nucleic acid). For purposes of the present specification, such vector nucleic acids are considered "therapeutic agents" if they encode or otherwise deliver a therapeutically active agent, even if they do not themselves have therapeutic activity.

In certain embodiments, a chlorotoxin agent comprises a nucleic acid therapeutic agent that comprises or encodes an antisense compound. The terms "antisense compound or agent", "antisense oligomer", "antisense oligonucleotide", and "antisense oligonucleotide analog" are used herein interchangeably, and refer to a sequence of nucleotide bases and a subunit-to-subunit backbone that allows the antisense compound to hybridize to a target sequence in an RNA by Watson-Crick base pairing to form an RNA oligomer heteroduplex within the target sequence. The oligomer may have exact sequence complementarity within the target sequence or near complementarity. Such antisense oligomers may block or inhibit translation of the mRNA containing the target sequence, or inhibit gene transcription. Antisense oligomers may bind to double-stranded or single-stranded sequences.

Examples of antisense oligonucleotides suitable for use in the practice of the present invention include, for example, those mentioned in the following reviews: R. A Stahel et al., Lung Cancer, 2003, 41: S81-S88; K. F. Pirollo et al., Pharmacol. Ther., 2003, 99: 55-77; A. C. Stephens and R. P. Rivers, Curr. Opin. Mol. Ther., 2003, 5: 118-122; N. M. Dean and C. F. Bennett, Oncogene, 2003, 22: 9087-9096; N. Schiavone et al., Curr. Pharm. Des., 2004, 10: 769-784; L. Vidal et al., Eur. J. Cancer, 2005, 41: 2812-2818; T. Aboul-Fadl, Curr. Med. Chem., 2005, 12: 2193-2214; M. E. Gleave and B. P. Monia, Nat. Rev. Cancer, 2005, 5: 468-479; Y. S. Cho-Chung, Curr. Pharm. Des., 2005, 11: 2811-2823; E. Rayburn et al., Lett. Drug Design & Discov., 2005, 2: 1-18; E. R. Rayburn et al., Expert Opin. Emerg. Drugs, 2006, 11: 337-352; I. Tamm and M. Wagner, Mol. Biotechnol., 2006, 33: 221-238 (each of which is incorporated herein by reference in its entirety).

Examples of suitable antisense oligonucleotides include, for example olimerson sodium (also known as Genasense™ or G31239, developed by Genta, Inc., Berkeley Heights, N.J.), a phosphorothioate oligomer targeted towards the initiation codon region of the bcl-2 mRNA, which is a potent inhibitor of apoptosis and is overexpressed in many cancer including, follicular lymphomas, breast, colon and prostate cancers, and intermediate/high-grade lymphomas (C. A. Stein et al., Semin. Oncol., 2005, 32: 563-573; S. R. Frankel, Semin. Oncol., 2003, 30: 300-304). Other suitable antisense oligonucleotides include GEM-231 (HYB0165, Hybridon, Inc., Cambridge, Mass.), which is a mixed backbone oligonucleotide directed against cAMP-dependent protein kinase A (PKA) (S. Goel et al., Clin. Cancer Res., 203, 9: 4069-4076); Affinitak (ISIS 3521 or aprinocarsen, ISIS pharmaceuticals, Inc., Carlsbad, Calif.), an antisense inhibitor of PKC-alpha; OGX-011 (Isis 112989, Isis Pharmaceuticals, Inc.), a 2'-methoxyethyl modified antisense oligonucleotide against clusterin, a glycoprotein implicated in the regulation of the cell cycle, tissue remodeling, lipid transport and cell death and which is overexpressed in cancers of breast, prostate and colon; ISIS 5132 (Isis 112989, Isis Pharmaceuticals, Inc.), a phosphorothioate oligonucleotide complementary to a sequence of the 3'-unstranslated region of the c-raf-1 mRNA (S. P. Henry et al., Anticancer Drug Des., 1997, 12: 409-420; B. P. Monia et al., Proc. Natl. Acad. Sci. USA, 1996, 93: 15481-15484; C. M. Rudin et al., Clin. Cancer Res., 2001, 7: 1214-1220); ISIS 2503 (Isis Pharmaceuticals, Inc.), a phosphorothioate oligonucleotide antisense inhibitor of human H-ras mRNA expression (J. Kurreck, Eur. J. Biochem., 2003, 270: 1628-1644); oligonucleotides targeting the X-linked inhibitor of apoptosis protein (XIAP), which blocks a substantial portion of the apoptosis pathway, such as GEM 640 (AEG 35156, Aegera Therapeutics Inc. and Hybridon, Inc.) or targeting survivin, an inhibitor of apoptosis protein (IAP), such as ISIS 23722 (Isis Pharmaceuticals, Inc.), a 2'-O-methoxyethyl chimeric oligonucleotide; MG98, which targets DNA methyl transferase; and GTI-2040 (Lorus Therapeutics, Inc. Toronto, Canada), a 20-mer oligonucleotide that is complementary to a coding region in the mRNA of the R2 small subunit component of human ribonucleotide reductase.

Other suitable antisense oligonucleotides include antisense oligonucleotides that are being developed against Her-2/neu, c-Myb, c-Myc, and c-Raf (see, for example, A. Biroccio et al., Oncogene, 2003, 22: 6579-6588; Y. Lee et al., Cancer Res., 2003, 63: 2802-2811; B. Lu et al., Cancer Res., 2004, 64: 2840-2845; K. F. Pirollo et al., Pharmacol. Ther., 2003, 99: 55-77; and A. Rait et al., Ann. N. Y. Acad. Sci., 2003, 1002: 78-89).

In certain embodiments, anchlorotoxin agent of the present invention comprises a nucleic acid anti-cancer agent that comprises or encodes an interfering RNA molecule. The terms "interfering RNA" and "interfering RNA molecule" are used herein interchangeably, and refer to an RNA molecule that can inhibit or downregulate gene expression or silence a gene in a sequence-specific manner, for example by mediating RNA interference (RNAi). RNA interference (RNAi) is an evolutionarily conserved, sequence-specific mechanism triggered by double-stranded RNA (dsRNA) that induces degradation of complementary target single-stranded mRNA and "silencing" of the corresponding translated sequences (McManus and Sharp, 2002, Nature Rev. Genet., 2002, 3: 737). RNAi functions by enzymatic cleavage of longer dsRNA strands into biologically active "short-interfering RNA" (siRNA) sequences of about 21-23 nucleotides in length (Elbashir et al., Genes Dev., 2001, 15: 188). RNA interference has emerged as a promising approach for therapy of cancer.

An interfering RNA suitable for use in the practice of the present invention can be provided in any of several forms. For example, an interfering RNA can be provided as one or more of an isolated short interfering RNA (siRNA), double-stranded RNA (dsRNA), micro-RNA (miRNA), or short hairpin RNA (shRNA).

Examples of interfering RNA molecules suitable for use in the present invention include, for example, the iRNAs cited in the following reviews: O. Milhavet et al., Pharmacol. Rev., 2003, 55: 629-648; F. Bi et al., Curr. Gene. Ther., 2003, 3: 411-417; P. Y. Lu et al., Curr. Opin. Mol. Ther., 2003, 5: 225-234; I. Friedrich et al., Semin. Cancer Biol., 2004, 14: 223-230; M. Izquierdo, Cancer Gene Ther., 2005, 12: 217-227; P. Y. Lu et al., Adv. Genet., 2005, 54: 117-142; G. R. Devi, Cancer Gene Ther., 2006, 13: 819-829; M. A. Behlke, Mol. Ther., 2006, 13: 644-670; and L. N. Putral et al., Drug News Perspect., 2006, 19: 317-324 (each of which is incorporated herein by reference in its entirety).

Other examples of suitable interfering RNA molecules include, but are not limited to, p53 interfering RNAs (e.g., T. R. Brummelkamp et al., Science, 2002, 296: 550-553; M. T. Hemman et al., Nat. Genet., 2003, 33: 396-400); interfering RNAs that target the bcr-abl fusion, which is associated with development of chronic myeloid leukemia and acute lymphoblastic leukemia (e.g., M. Scherr et al., Blood, 2003, 101: 1566-1569; M. J. Li et al., Oligonucleotides, 2003, 13: 401-409), interfering RNAs that inhibit expression of NPM-ALK, a protein that is found in 75% of anaplastic large cell lymphomas and leads to expression of a constitutively active kinase associated with tumor formation (U. Ritter et al., Oligonucleotides, 2003, 13: 365-373); interfering RNAs that target oncogenes, such as Raf-1 (T. F. Lou et al., Oligonucleotides, 2003, 13: 313-324), K-Ras (T. R. Brummelkamp et al., Cancer Cell, 2002, 2: 243-247), erbB-2 (G. Yang et al., J. Biol. Chem., 2004, 279: 4339-4345); interfering RNAs that target b-catenin protein, whose over-expression leads to transactivation of the T-cell factor target genes, which is thought to be the main transforming event in colorectal cancer (M. van de Wetering et al., EMBO Rep., 2003, 4: 609-615).

C. Labeling Moieties

In certain embodiments, a chlorotoxin agent is labeled with at least one labeling moiety. For example, one or more chlorotoxin moieties and/or one or more therapeutic moieties within a chlorotoxin agent may be labeled with a labeling moiety.

The role of a labeling moiety is to facilitate detection of the chlorotoxin agent after binding to the tissue to be tested. Preferably, the labeling moiety is selected such that it generates a signal that can be measured and whose intensity is related to (e.g., proportional to) the amount of diagnostic agent bound to the tissue.

Preferably, labeling does not substantially interfere with the desired biological or pharmaceutical activity of the chlorotoxin agent. In certain embodiments, labeling involves attachment or incorporation of one or more labeling moieties to a chlorotoxin moiety, preferably to non-interfering positions on the peptide sequence of the chlorotoxin moiety. Such non-interfering positions are positions that do not participate in the specific binding of the chlorotoxin moiety to tumor cells.

A labeling moiety may be any entity that allows detection of achlorotoxin agent after binding to a tissue or system of interest. Any of a wide variety of detectable agents can be used as labeling moieties in chlorotoxin agents of the present invention. A labeling moiety may be directly detectable or indirectly detectable. Examples of labeling moieties include, but are not limited to: various ligands, radionuclides (e.g., $^{3}H$, $^{14}C$, $^{18}F$, $^{19}F$, $^{32}P$, $^{35}S$, $^{135}I$, $^{125}$, $^{123}I$, $^{64}Cu$, $^{187}Re$, $^{111}In$, $^{90}Y$, $^{99m}Tc$, $^{177}Lu$, etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

In certain embodiments, a labeling moiety comprises a fluorescent label. Numerous known fluorescent labeling moieties of a wide variety of chemical structures and physical characteristics are suitable for use in the practice of methods of diagnosis of the present invention. Suitable fluorescent dyes include, but are not limited to, fluorescein and fluorescein dyes (e.g., fluorescein isothiocyanine or FITC, naphthofluorescein, 4',5'-dichloro-2',7'-dimethoxy-fluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxy-coumarin, dialkylaminocoumarin, hydroxycoumarin, aminomethylcoumarin (AMCA), etc.), Oregon Green Dyes (e.g., Oregon Green 488, Oregon Green 500, Oregon Green 514., etc.), Texas Red, Texas Red-X, Spectrum Red™, Spectrum Green™, cyanine dyes (e.g., Cy-3™, Cy-5™, Cy-3.5™, Cy-5.5™, etc.), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660, Alexa Fluor 680, etc.), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "*The Handbook of Fluorescent Probes and Research Products*", $9^{th}$ Ed., Molecular Probes, Inc., Eugene, Oreg. Favorable properties of fluorescent labeling agents include high molar absorption coefficient, high fluorescence quantum yield, and photostability. In certain embodiments, labeling fluorophores desirably exhibit absorption and emission wavelengths in the visible (i.e., between 400 and 750 nm) rather than in the ultraviolet range of the spectrum (i.e., lower than 400 nm).

In certain embodiments, a labeling moiety comprises an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme may be conjugated to a chlorotoxin moiety using a linker group such as a carbodiimide, a diisocyanate, a glutaraldehyde, and the like.

In certain embodiments, a labeling moiety comprises a radioisotope that is detectable by Single Photon Emission Computed Tomography (SPECT) or Position Emission Tomography (PET). Examples of such radionuclides include, but are not limited to, iodine-131 ($^{131}I$), iodine-125 ($^{125}I$), bismuth-212 ($^{212}Bi$), bismuth-213 ($^{213}Bi$), astatine-221 ($^{211}At$), copper-67 ($^{67}Cu$), copper-64 ($^{64}Cu$),) rhenium-186 ($^{186}Re$), rhenium-186 ($^{188}Re$), phosphorus-32 ($^{32}P$), samarium-153 ($^{153}Sm$), lutetium-177 ($^{117}Lu$), technetium-99m ($^{99m}Tc$), gallium-67 ($^{67}Ga$), indium-111 ($^{111}In$), and thallium-201 ($^{201}Tl$).

In certain embodiments, a labeling moiety comprises a radioisotope that is detectable by Gamma camera. Examples of such radioisotopes include, but are not limited to, iodine-131 ($^{131}I$), and technetium-99m ($^{99m}Tc$).

In certain embodiments, a labeling moiety comprises a paramagnetic metal ion that is a good contrast enhancer in Magnetic Resonance Imaging (MRI). Examples of such paramagnetic metal ions include, but are not limited to, gadolinium III ($Gd^{3+}$), chromium III ($Cr^{3+}$), dysprosium III ($Dy^{3+}$), iron III ($Fe^{3+}$), manganese II ($Mn^{2+}$), and ytterbium III ($Yb^{3+}$). In certain embodiments, the labeling moieties comprises gadolinium III ($Gd^{3+}$). Gadolinium is an FDA-approved contrast agent for MRI, which accumulates in abnormal tissues causing these abnormal areas to become very bright (enhanced) on the magnetic resonance image. Gadolinium is known to provide great contrast between normal and abnormal tissues in different areas of the body, in particular in the brain.

In certain embodiments, a labeling moiety comprises a stable paramagnetic isotope detectable by nuclear magnetic resonance spectroscopy (MRS). Examples of suitable stable paramagnetic isotopes include, but are not limited to, carbon-13 ($^{13}C$) and fluorine-19 ($^{19}F$).

D. Formation of Chlorotoxin Agents

In certain embodiments, a chlorotoxin agent comprises at least one chlorotoxin moiety associated with at least one therapeutic moiety. Thus, a chlorotoxin agent results from the association (e.g., binding, interaction, fusion, or coupling) of at least two other molecules.

Association between a chlorotoxin moiety and a therapeutic moiety within a chlorotoxin agent may be covalent or non-covalent. Irrespective of the nature of the binding, interaction, or coupling, the association between a chlorotoxin moiety and a therapeutic moiety is preferably selective, specific and strong enough so that the chlorotoxin agent does not dissociate before or during transport/delivery to and into the tumor. Association between a chlorotoxin moiety and a therapeutic moiety within a chlorotoxin agent may be achieved using any chemical, biochemical, enzymatic, or genetic coupling known to one skilled in the art.

In certain embodiments, association between a chlorotoxin moiety and a therapeutic moiety is non-covalent. Examples of non-covalent interactions include, but are not limited to, hydrophobic interactions, electrostatic interactions, dipole interactions, van der Waals interactions, and hydrogen bonding.

In certain embodiments, association between achlorotoxin moiety and a therapeutic moiety is covalent. As will be appreciated by one skilled in the art, the moieties may be attached to each other either directly or indirectly (e.g., through a linker, as described below).

In certain embodiments, the chlorotoxin moiety and therapeutic moiety are directly covalently linked to each other. Direct covalent binding can be through a linkage such as an amide, ester, carbon-carbon, disulfide, carbamate, ether, thioether, urea, amine, or carbonate linkage. The covalent binding can be achieved by taking advantage of functional groups present on the chlorotoxin moiety and/or the therapeutic moiety. Alternatively, a non-critical amino acid may be replaced by another amino acid that will introduce a useful group (amino, carboxy or sulfhydryl) for coupling purposes. Alternatively, an additional amino acid may be added to the chlorotoxin moiety to introduce a useful group (amino, carboxy or sulfhydryl) for coupling purposes. Suitable functional groups that can be used to attach moieties together include, but are not limited to, amines, anhydrides, hydroxyl groups, carboxy groups, thiols, and the like. An activating agent, such as a carbodiimide, can be used to form a direct linkage. A wide variety of activating agents are known in the art and are suitable for linking a therapeutic agent and a chlorotoxin moiety.

In other embodiments, a chlorotoxin moiety and a therapeutic moiety within a chlorotoxin agent are indirectly covalently linked to each other via a linker group. This can be accomplished by using any number of stable bifunctional agents well known in the art, including homofunctional and heterofunctional agents (for examples of such agents, see, e.g., Pierce Catalog and Handbook). The use of a bifunctional linker differs from the use of an activating agent in that the former results in a linking moiety being present in the resulting chlorotoxin agent, whereas the latter results in a direct coupling between the two moieties involved in the reaction. The role of a bifunctional linker may be to allow reaction between two otherwise inert moieties. Alternatively or additionally, the bifunctional linker that becomes part of the reaction product may be selected such that it confers some degree of conformational flexibility to the chlorotoxin agent (e.g., the bifunctional linker comprises a straight alkyl chain containing several atoms, for example, the straight alkyl chain contains between 2 and 10 carbon atoms). Alternatively or additionally, the bifunctional linker may be selected such that the linkage formed between a chlorotoxin moiety and therapeutic moiety is cleavable, e.g. hydrolysable (for examples of such linkers, see e.g. U.S. Pat. Nos. 5,773,001; 5,739,116 and 5,877,296, each of which is incorporated herein by reference in its entirety). Such linkers are for example preferably used when higher activity of the chlorotoxin moiety and/or of the therapeutic moiety is observed after hydrolysis of the conjugate. Exemplary mechanisms by which a therapeutic moiety may be cleaved from a chlorotoxin moiety include hydrolysis in the acidic pH of the lysosomes (hydrazones, acetals, and cis-aconitate-like amides), peptide cleavage by lysosomal enzymes (the capthepsins and other lysosomal enzymes), and reduction of disulfides). Another mechanism by which a therapeutic moiety is cleaved from the chlorotoxin agent includes hydrolysis at physiological pH extra- or intra-cellularly. This mechanism applies when the crosslinker used to couple the therapeutic moiety to the chlorotoxin moiety is a biodegradable/bioerodible entity, such as polydextran and the like.

For example, hydrazone-containing chlorotoxin agents can be made with introduced carbonyl groups that provide the desired release properties. Chlorotoxin agents can also be made with a linker that comprise an alkyl chain with a disulfide group at one end and a hydrazine derivative at the other end. Linkers containing functional groups other than hydrazones also have the potential to be cleaved in the acidic milieu of lysosomes. For example, chlorotoxin agents can be made from thiol-reactive linkers that contain a group other than a hydrazone that is cleavable intracellularly, such as esters, amides, and acetals/ketals.

Another example of class of pH sensitive linkers are the cis-aconitates, which have a carboxylic acid group juxtaposed to an amide group. The carboxylic acid accelerates amide hydrolysis in the acidic lysosomes. Linkers that achieve a similar type of hydrolysis rate acceleration with several other types of structures can also be used.

Another potential release method for chlorotoxin agents is the enzymatic hydrolysis of peptides by the lysosomal enzymes. In one example, a peptidic toxin is attached via an amide bond to para-aminobenzyl alcohol and then a carbamate or carbonate is made between the benzyl alcohol and the therapeutic moiety. Cleavage of the peptide leads to collapse of the amino benzyl carbamate or carbonate, and release of the therapeutic moiety. In another example, a phenol can be cleaved by collapse of the linker instead of the carbamate. In another variation, disulfide reduction is used to initiate the collapse of a para-mercaptobenzyl carbamate or carbonate.

In embodiments where a therapeutic moiety within a chlorotoxin agent is a protein, a polypeptide or a peptide, the chlorotoxin agent may be a fusion protein. As already defined above, a fusion protein is a molecule comprising two or more proteins or peptides linked by a covalent bond via their individual peptide backbones. Fusion proteins used in methods of the present invention can be produced by any suitable method known in the art. For example, they can be produced by direct protein synthetic methods using a polypeptide synthesizer. Alternatively, PCR amplification of gene fragments can be carried out using anchor primers which give rise to complementary overhangs between two consecutive gene fragments that can subsequently be annealed and re-amplified to generate a chimeric gene sequence. Fusion proteins can be obtained by standard recombinant methods (see, for example, Maniatis et al. "*Molecular Cloning: A Laboratory Manual*", $2^{nd}$ Ed., 1989, Cold Spring Harbor Laboratory, Cold Spring, N.Y.). These methods generally comprise (1) construction of a nucleic acid molecule that encodes the desired fusion protein; (2) insertion of the nucleic acid molecule into a recombinant expression vector; (3) transformation of a suitable host cell with the expression vector; and (4) expression of the fusion protein in the host cell. Fusion proteins produced by such methods may be recovered and isolated, either directly from the culture medium or by lysis of the cells, as known in the art. Many methods for purifying proteins produced by transformed host cells are well-known in the art. These include, but are not limited to, precipitation, centrifugation, gel filtration, and (ion-exchange, reverse-phase, and affinity) column chromatography. Other purification methods have been described (see, for example, Deutscher et al. "*Guide to Protein Purification*" in Methods in Enzymology, 1990, Vol. 182, Academic Press).

As can readily be appreciated by one skilled in the art, a chlorotoxin agent used in methods of the present invention can comprise any number of chlorotoxin moieties and any number of therapeutic moieties, associated to one another by any number of different ways. The design of a conjugate will be influenced by its intended purpose(s) and the properties that are desirable in the particular context of its use. Selection of a method to associate or bind a chlorotoxin moiety to a therapeutic moiety to form a chlorotoxin agent is within the knowledge of one skilled in the art and will generally depend on the nature of the interaction desired between the moieties (i.e., covalent vs. non-covalent and/or cleavable vs.

non-cleavable), the nature of the therapeutic moiety, the presence and nature of functional chemical groups on the moieties involved and the like.

In labeled chlorotoxin agents, association between a chlorotoxin moiety (or therapeutic moiety) and a labeling moiety may be covalent or non-covalent. In case of covalent association, the chlorotoxin (or therapeutic) and labeling moieties may be attached to each other either directly or indirectly, as described above.

In certain embodiments, association between a chlorotoxin moiety (or therapeutic moiety) and a labeling moiety is non-covalent. Examples of non-covalent associations include, but are not limited to, hydrophobic interactions, electrostatic interactions, dipole interactions, van der Waals interactions, and hydrogen bonding. For example, a labeling moiety can be non-covalently attached to a chlorotoxin moiety (or therapeutic moiety) by chelation (e.g., a metal isotope can be chelated to a polyHis region attached, e.g., fused, to a chlorotoxin moiety).

In certain embodiments, a chlorotoxin moiety (or therapeutic moiety) is isotopically labeled (i.e., it contains one or more atoms that have been replaced by an atom having an atomic mass or mass number different from the atomic mass or mass number usually found in nature). Alternatively or additionally, an isotope may be attached to a chlorotoxin moiety and/or therapeutic moiety.

As can readily be appreciated by one skilled in the art, a labeled chlorotoxin agent used in certain methods of the present invention can comprise any number of chlorotoxin moieties, any number of therapeutic moieties, and any number of labeling moieties, associated to one another by any number of different ways. The design of a labeled chlorotoxin agent will be influenced by its intended purpose(s), the properties that are desirable in the context of its use, and the method selected from the detection.

E. Modifications

In certain embodiments, chlorotoxin agents are modified by covalent attachment to macromolecules such as polymers. Without wishing to be bound by any particular theory, covalent attachment of, for example, polymers, may mask the chlorotoxin agent antigenically such that the agent's bioavailability and/or tolerance in an animal's body is improved. An example of such a polymer is polyethylene glycol (PEG), which can often be covalently attached to N and/or C termini and/or to cysteines in peptides and/or polypeptides. "PEGylation" refers to the covalent addition of PEG to a molecule. In some embodiments, chlorotoxin agents are not modified at any site. In some embodiments, chlorotoxin agents are modified (e.g., by PEGylation) at one site per molecule. In some embodiments, chlorotoxin agents are modified (e.g., by PEGylation) at more than one site per molecule.

In some embodiments, such modifications increase the half life of chlorotoxin agents in vivo. For example, the half life may be at least approximately 10 hours, at least approximately 16 hours, etc. (See, e.g., Example 9). Such improved bioavailability may in some embodiments facilitate dosing regimens that involve lower frequencies of dosing. (Dosing regimens are discussed herein.)

II. Methods of Treatment and/or Detection

Methods of treatment of the invention include administration of an effective dose of a chlorotoxin agent, or a pharmaceutical composition thereof, to an individual in need thereof (e.g., a individual who has, has had, is at risk of developing, and/or is susceptible to at least one tumor metastastis). Thus, methods of treatment of the present invention may be used for reducing the sizes and/or numbers of tumor metastases, inhibiting the growth and/or formation of metastases, and/or prolonging the survival time of mammals (including humans) suffering from metastatic cancers and metastatic cancer conditions.

Without wishing to be bound by any particular theory, we note that formation of new blood vessels (angiogenesis) may be important for developing and/or maintaining metastases. As demonstrated in Example 4, chlorotoxin can inhibit new blood vessel formation. Chlorotoxin may also cause the regression of newly developed blood vessels (neovasculature). In some embodiments of the invention, neovasculature of at least one metastasis regresses. In some embodiments of the invention, neovascularization is inhibited.

A. Indications

Throughout the specification, the convention of naming a metastastic tumor after the site of its primary origin is used. Thus, for example, "metastatic prostate cancer" refers to cancer originating from the prostate that has spread to other organs, regardless of the location of the metastasis. Metastases may form in a variety of organs including, for example, brain, lung, bone, liver, lymph nodes, ovary, etc. Certain kinds of tumors may typically metastasize to certain organs. For example, melanomas often metastasize to the brain, prostate cancers often metastasize to bone, stomach cancers in women often metastasize to the ovary, breast cancers often metastasize to bone, and colon cancers often metastasize to the liver. Inventive methods may be used to treat metastases in a variety of organs as described above, including metastases that are distant from the site of the primary tumor. Furthermore, because chlorotoxin agents may cross the blood/brain barrier (see, for example, Examples 2 and 3) inventive methods may be used to treat metastases in brain.

Primary tumors may often spread to nearby lymph nodes. Inventive methods may be used to control or eliminate spreading to lymph nodes as well. Cancer/tumor cells may break away from a primary tumor and metastasize by traveling through the bloodstream or lymphatic channels. In certain embodiments of the invention, for example some of those in which the chlorotoxin agent is systemically delivered, such metastasizing cells are bound by the chlorotoxin agent and targeted for destruction.

In some embodiments, inventive treatment methods further comprise detecting at least one metastasis prior to administration of the chlorotoxin agent. In some such embodiments, detecting at least one metastasis comprises administering an effective dose of a labeled chlorotoxin agent.

It will be understood, nevertheless, that inventive methods can be used to treat individuals having, having had, or at risk of having one or more metastases even though the location or existence of the one or more metastases may not be known. A patient may not have been diagnosed as having any metastases at all, or only a subset of metastases in the patient may have been identified and/or located. In some embodiments of invention, the chlorotoxin agent is delivered systemically, resulting in chlorotoxin agent being delivered throughout the body. Thus, it is not necessary to target delivery of chlorotoxin agent to a particular tissue or set of tissues in order to effect delivery of chlorotoxin agent to metastases.

Examples of primary cancers and cancer conditions that can develop into metastatic cancers that can be treated according to the present invention include, but are not limited to, tumors of the brain and central nervous system (e.g., tumors of the meninges, brain, spinal cord, cranial nerves and other parts of the CNS, such as glioblastomas or medulloblastomas); head and/or neck cancer, breast tumors, tumors of the circulatory system (e.g., heart, mediastinum and pleura, and other intrathoracic organs, vascular tumors, and tumor-associated vascular tissue); tumors of the blood and lymphatic system (e.g., Hodgkin's disease, Non-Hodgkin's disease lymphoma, Burkitt's lymphoma, AIDS-related lymphomas, malignant immunoproliferative diseases, multiple myeloma, and malignant plasma cell neoplasms, lymphoid leukemia, myeloid leukemia, acute or chronic lymphocytic leukemia, monocytic leukemia, other leukemias of specific cell type, leukemia of unspecified cell type, unspecified malignant neoplasms of lymphoid, haematopoietic and related tissues, such as diffuse large cell lymphoma, T-cell lymphoma or cutaneous T-cell lymphoma); tumors of the excretory system (e.g., kidney, renal pelvis, ureter, bladder, and other urinary organs); tumors of the gastrointestinal tract (e.g., oesophagus, stomach, small intestine, colon, colorectal, rectosigmoid junction, rectum, anus, and anal canal); tumors involving the liver and intrahepatic bile ducts, gall bladder, and other parts of the biliary tract, pancreas, and other digestive organs; tumors of the oral cavity (e.g., lip, tongue, gum, floor of mouth, palate, parotid gland, salivary glands, tonsil, oropharynx, nasopharynx, puriform sinus, hypopharynx, and other sites of the oral cavity); tumors of the reproductive system (e.g., vulva, vagina, Cervix uteri, uterus, ovary, and other sites associated with female genital organs, placenta, penis, prostate, testis, and other sites associated with male genital organs); tumors of the respiratory tract (e.g., nasal cavity, middle ear, accessory sinuses, larynx, trachea, bronchus and lung, such as small cell lung cancer and non-small cell lung cancer); tumors of the skeletal system (e.g., bone and articular cartilage of limbs, bone articular cartilage and other sites); tumors of the skin (e.g., malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland, and other endocrine glands and related structures, secondary and unspecified malignant neoplasms of lymph nodes, secondary malignant neoplasm of respiratory and digestive systems and secondary malignant neoplasms of other sites.

In certain embodiments of the present invention, inventive compositions and methods are used in the treatment of metastatic sarcomas. In some embodiments, compositions and methods of the present invention are used in the treatment of metastatic cancers originating from bladder cancer, breast cancer, chronic lymphoma leukemia, head and neck cancer, endometrial cancer, Non-Hodgkin's lymphoma, non-small cell lung cancer, ovarian cancer, pancreatic cancer, and prostate cancer.

In certain embodiments of the present invention, compositions and methods are used for the treatment of metastatic tumors of neuroectodermal origin. Any metastatic tumor of neuroectodermal origin present in a human patient can generally be treated using a composition/method of the present invention. In certain embodiments, the metastatic tumor of neuroectodermal origin affecting the patient is a member of the group consisting of gliomas, meningiomas, ependymomas, medulloblastomas, neuroblastomas, gangliomas, pheochromocytomas, melanomas, peripheral primitive neuroectodermal tumors, small cell carcinoma of the lung, Ewing's sarcoma, and metastatic tumors of neuroectodermal origin in the brain. In some embodiments, the metastatic tumor of neuroectodermal origin is melanoma. In some such embodiments, the melanoma is cutaneous or intraocular melanoma.

In certain embodiments, the metastatic tumor of neuroectodermal origin affects the brain of the patient. In certain embodiments, the brain tumor is a glioma. About half of all primary brain tumors are gliomas. There are 4 main types of glioma: astrocytoma (which is the most common type of glioma in both adults and children), ependymoma, oligodendroglioma, and mixed glioma. Gliomas can be classified according to their location: infratentorial (i.e., located in the lower part of the brain, found mostly in children patients) or supratentorial (i.e., located in the upper part of the brain, found mostly in adult patients).

Gliomas are further categorized according to their grade, which is determined by pathologic evaluation of the tumor. The World Health Organization (WHO) has developed a grading system, from Grade I gliomas, which tend to be the least aggressive, to Grade IV gliomas, which tend to be the most aggressive and malignant. Examples of low grade (i.e., Grade I or Grade II) gliomas include, but are not limited to, pilocytic astrocytoma (also called juvenile pilocytic astrocytoma), fibrillary astrocytoma, pleomorphic xantroastrocytomoa, and desembryoplastic neuroepithelial tumor. High-grade gliomas encompass Grade III gliomas (e.g., anaplastic astrocytoma, AA) and Grade IV gliomas (glioblastoma multiforme, GBM). Anaplastic astrocytoma is most frequent among men and women in theirs 30s-50s, and accounts for 4% of all brain tumors. Glioblastoma multiforme, the most invasive type of glial tumor, is most common in men and women in their 50s-70s and accounts for 23% of all primary brain tumors. The prognosis is the worst for Grade IV gliomas, with an average survival time of 12 months. In certain embodiments, methods of the present invention are used for the treatment of high-grade gliomas.

Despite aggressive treatment, gliomas usually recur, often with a higher grade and sometimes with a different morphology. While recurrence varies, Grade IV gliomas invariably recur. Thus, in certain embodiments, methods of the present invention are used for the treatment of metastatic recurrent gliomas, in particular, recurrent high-grade gliomas.

Metastatic tumors that can be treated using compositions and methods of the present invention also include metastatic tumors that are refractory to treatment with other chemotherapeutics. The term "refractory", when used herein in reference to a tumor means that the tumor (and/or metastases thereof), upon treatment with at least one chemotherapeutic other than an inventive composition, shows no or only weak anti-proliferative response (i.e., no or only weak inhibition of tumor growth) after the treatment with such a chemotherapeutic agent—that is, a tumor that cannot be treated at all or only with unsatisfying results with other (preferably standard) chemotherapeutics. The present invention, where treatment of refractory tumors and the like is mentioned, is to be understood to encompass not only (i) tumors where one or more chemotherapeutics have already failed during treatment of a patient, but also (ii) tumors that can be shown to be refractory by other means, e.g., biopsy and culture in the presence of chemotherapeutics.

Patients who can receive a treatment according to the present invention generally include any patient who is or has been diagnosed with a tumor. In some embodiments, the patient is diagnosed as having one or more metastasis. In some embodiments, the patient is diagnosed as having a tumor that is known to metastasize. In some embodiments, the patient is diagnosed as having a tumor that is determined to be at a stage during which metastasis is likely or possible. In some embodiments, the patient has had a tumor, but no longer exhibits signs of having the primary tumor; in some such embodiments, the patient has metastases nevertheless that may be treated with inventive methods. As will be recognized by one skilled in the art, different methods of diagnosis may be performed depending on the location and nature of the tumor and/or metastases, including imaging, biopsy, etc.

B. Dosages and Administrations

In a method of treatment of the present invention, a chlorotoxin agent, or a pharmaceutical composition thereof, will generally be administered in such amounts and for such a time as is necessary or sufficient to achieve at least one desired result. For example, a chlorotoxin agent can be administered in such amounts and for such a time that it kills cancer cells, reduces tumor size, reduces the size of one or more metastases, inhibits or delay tumor growth or metastasis, prolongs the survival time of patients, or otherwise yields clinical benefits.

A treatment according to the present invention may consist of a single dose or a plurality of doses over a period of time. Administration may be one or multiple times daily, weekly (or at some other multiple day interval) or on an intermittent schedule. The exact amount of a chlorotoxin agent, or pharmaceutical composition thereof, to be administered will vary from subject to subject and will depend on several factors (see below).

Chlorotoxin agents, or pharmaceutical compositions thereof, may be administered using any administration route effective for achieving the desired therapeutic effect. In certain embodiments of the invention, chlorotoxin agents (or pharmaceutical compositions thereof) are delivered systemically. Typical systemic routes of administration include, but are not limited to, intramuscular, intravenous, pulmonary, and oral routes. Systemic administration may also be performed, for example, by infusion or bolus injection, or by absorption through epithelial or mucocutaneous linings (e.g., oral, mucosa, rectal and intestinal mucosa, etc). In certain embodiments, the chlorotoxin agent is administered intravenously. Exemplary procedures for the intravenous administration of a chlorotoxin agent in human patients are described in Example 2.

Depending on the route of administration, effective doses may be calculated according to the body weight; body surface area; primary organ/tumor size; and/or number, sizes, and/or types of metastases of the subject to be treated. Optimization of the appropriate dosages can readily be made by one skilled in the art in light of pharmacokinetic data observed in human clinical trials. The final dosage regimen will be determined by the attending physician, considering various factors which modify the action of the drugs, e.g., the drug's specific activity, the severity of the damage and the responsiveness of the patient, the age, condition, body weight, sex and diet of the patient, the severity of any present infection, time of administration, the use (or not) of other therapies, and other clinical factors. As studies are conducted using chlorotoxin agents, further information will emerge regarding the appropriate dosage levels and duration of treatment.

Typical dosages comprise 1.0 pg/kg body weight to 100 mg/kg body weight. For example, for systemic administration, dosages may be 100.0 ng/kg body weight to 10.0 mg/kg body weight.

More specifically, in certain embodiments where a chlorotoxin agent is administered intravenously, dosing of the agent may comprise administration of one or more doses comprising about 0.005 mg/kg to about 5 mg/kg, e.g., from about 0.005 mg/kg to about 5 mg/kg, from about 0.01 mg/kg to about 4 mg/kg, from about 0.02 mg/kg to about 3 mg/kg, from about 0.03 mg/kg to about 2 mg/kg or from about 0.03 mg/kg to about 1.5 mg/kg of chlorotoxin. For example, in certain embodiments, one or more doses of chlorotoxin agent may be administered that each contains about 0.03 mg/kg, about 0.04 mg/kg, about 0.05 mg/kg, about 0.06 mg/kg, about 0.07 mg/kg, about 0.09 mg/kg, about 1.0 mg/kg or more than 1.0 mg/kg of chlorotoxin. In other embodiments, one or more doses of chlorotoxin agent may be administered that each contains about 0.05 mg/kg, about 0.10 mg/kg, about 0.15 mg/kg, about 0.20 mg/kg, about 0.25 mg/kg, about 0.30 mg/kg, about 0.35 mg/kg, about 0.40 mg/kg, about 0.45 mg/kg, about 0.50 mg/kg, about 0.55 mg/kg, about 0.60 mg/kg, about 0.65 mg/kg, about 0.70 mg/kg, about 0.75 mg/kg, about 0.80 mg/kg, about 0.85 mg/kg, about 0.90 mg/kg, about 0.95 mg/kg, about 1.0 mg/kg, or more than about 1 mg/kg of chlorotoxin. In yet other embodiments, one or more doses of chlorotoxin agent may be administered that each contains about 1.0 mg/kg, about 1.05 mg/kg, about 1.10 mg/kg, about 1.15 mg/kg, about 1.20 mg/kg, about 1.25 mg/kg, about 1.3 mg/kg, about 1.35 mg/kg, about 1.40 mg/kg, about 1.45 mg/kg, about 1.50 mg/kg, or more than about 1.50 mg/kg of chlorotoxin. In such embodiments, at treatment may comprise administration of a single dose of chlorotoxin agent or administration of 2 doses, 3 doses, 4 doses, 5 doses, 6 doses or more than 6 doses. Two consecutive doses may be administered at 1 day interval, 2 days interval, 3 days interval, 4 days interval, 5 days interval, 6 days interval, 7 days interval, or more than 7 days interval (e.g., 10 days, 2 weeks, or more than 2 weeks).

C. Combination Therapies

It will be appreciated that methods of treatment of the present invention can be employed in combination with additional therapies (i.e., a treatment according to the present invention can be administered concurrently with, prior to, or subsequently to one or more desired therapeutics or medical procedures). The particular combination of therapies (therapeutics or procedures) to employ in such a combination regimen will take into account compatibility of the desired therapeutics and/or procedures and the desired therapeutic effect to be achieved.

For example, methods of treatment of the present invention can be employed together with other procedures including surgery, radiotherapy (e.g., γ-radiation, neuron beam radiotherapy, electron beam radiotherapy, proton therapy, brachytherapy, systemic radioactive isotopes), endocrine therapy, hyperthermia, and cryotherapy, depending on the tumor to be treated.

In many cases of metastatic brain tumor, a treatment of the present invention will often be administered after surgery to remove the primary tumor. In the treatment of brain tumor, the main goal of surgery is to achieve a gross-total resection, i.e., removal of all visible primary tumor. One of the difficulties in achieving such a goal is that these tumors are infiltrative, i.e., they tend to weave in and out among normal brain structures. Furthermore, there is a great variability in the amount of tumor that can be safely removed from the brain of a patient. Removal is generally not possible if all or part of the tumor is located in a region of the brain controlling critical functions. Furthermore, it may not be possible or practical to remove and/or destroy metastases at distant sites with surgery alone.

In many cases of metastatic brain tumor, a treatment of the present invention will often be administered in combination with (i.e., concurrently with, prior to, or subsequently to) radiotherapy. In conventional treatments, radiotherapy generally follows surgery. Radiation is generally given as a series of daily treatments (called fractions) over several weeks. This "fractionated" approach to administering radiation is important to maximize the destruction of tumor cells and minimize side effects on normal adjacent brain. The area over which the radiation is administered (called the radiation field) is carefully calculated to avoid including as much of normal brain as is feasible.

Alternatively or additionally, methods of treatment of the present invention can be administered in combination with other therapeutic agents, such as agents that attenuate any adverse effects (e.g., antiemetics, etc.) and/or with other approved chemotherapeutic drugs. Examples of chemotherapeutics include, but are not limited to, alkylating drugs (e.g., mechlorethamine, chlorambucil, cyclophosphamide, melphalan, ifosfamide, etc.), antimetabolites (e.g., methotrexate, etc.), purine antagonists and pyrimidine antagonists (e.g., 6-mercaptopurine, 5-fluorouracil, cytarabine, gemcitabine, etc.), spindle poisons (e.g., vinblastine, vincristine, vinorelbine, paclitaxel, etc.), podophyllotoxins (e.g., etoposide, irinotecan, topotecan, etc.), antibiotics (e.g., doxorubicin, bleomycin, mitomycin, etc.), nitrosureas (e.g., carmustine, lomustine, nomustine, etc.), inorganic ions (e.g., cisplatin, carboplatin, etc.), enzymes (e.g., asparaginase, etc.), and hormones (e.g., tamoxifen, leuprolide, flutamide, megestrol, etc.), to name a few. For a more comprehensive discussion of updated cancer therapies see, http://www.cancer.gov/, a list of the FDA approved oncology drugs at http://wwwfda.gov/cder/cancer/druglistframe.htm, and The Merck Manual, Seventeenth Ed. 1999, the entire contents of which are hereby incorporated by reference.

Methods of the present invention can also be employed together with one or more further combinations of cytotoxic agents as part of a treatment regimen, wherein the further combination of cytotoxic agents is selected from: CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, procarbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine); ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and procarbazine); ABVD (adriamycin/doxorubicin, bleomycin, vinblastine, and dacarbazine); MOPP (mechloethamine, vincristine, prednisone and procarbazine) alternating with ABV (adriamycin/doxorubicin, bleomycin, and vinblastine); MOPP (mechloethamine, vincristine, prednisone, and procarbazine) alternating with ABVD (adriamycin/doxorubicin, bleomycin, vinblastine, and dacarbazine); ChlVPP (chlorambucil, vinblastine, procarbazine, and prednisone); IMVP-16 (ifosfamide, methotrexate, and etoposide); MIME (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP(B) (cyclophosphamide, etoposide, procarbazine, prednisone, and bleomycin); CAMP (lomustine, mitoxantrone, cytarabine, and prednisone); CVP-1 (cyclophosphamide, vincristine, and prednisone), ESHOP (etoposide, methylpredisolone, high-dose cytarabine, vincristine and cisplatin); EPOCH (etoposide, vincristine, and doxorubicin for 96 hours with bolus doses of cyclophosphamide and oral prednisone), ICE (ifosfamide, cyclophosphamide, and etoposide), CEPP(B) (cyclophosphamide, etoposide, procarbazine, prednisone, and bleomycin), CHOP-B (cyclophosphamide, doxorubicin, vincristine, prednisone, and bleomycin), CEPP-B (cyclophosphamide, etoposide, procarbazine, and bleomycin), and P/DOCE (epirubicin or doxorubicin, vincristine, cyclophosphamide, and prednisone).

As will be appreciated by one skilled in the art, the selection of one or more therapeutic agents to be administered in combination with a method of treatment of the present invention will depend on the metastatic tumor to be treated.

For example, chemotherapeutic drugs prescribed for brain tumors include, but are not limited to, temozolomide (Temodar®), procarbazine (Matulane®), and lomustine (CCNU), which are taken orally; vincristine (Oncovin® or Vincasar PFS®), cisplatin (Platinol®), carmustine (BCNU, BiCNU), and carboplatin (Paraplatin®), which are administered intravenously; and mexotrexate (Rheumatrex® or Trexall®), which can be administered orally, intravenously or intrathecally (i.e., injected directly into spinal fluid). BCNU is also given under the form of a polymer wafer implant during surgery (Giadel® wafers). One of the most commonly prescribed combination therapy for brain tumors is PCV (procarbazine, CCNU, and vincristine) which is usually given every six weeks.

In embodiments where the tumor to be treated is a brain tumor of neuroectodermal origin, a method of the present invention may be used in combination with agents for the management of symptoms such as seizures and cerebral edema. Examples of anticonvulsants successfully administered to control seizures associated with brain tumors include, but are not limited to, phenytoin (Dilantin®), Carbamazepine (Tegretol®) and divalproex sodium (Depakote®). Swelling of the brain may be treated with steroids (e.g., dexamethasone (Decadron®).

D. Pharmaceutical Compositions

As mentioned above, methods of treatment, inhibition and/or reduction, and/or detection of the present invention include administration of a chlorotoxin agent per se or in the form of a pharmaceutical composition. A pharmaceutical composition will generally comprise an effective amount of at least one chlorotoxin agent and at least one pharmaceutically acceptable carrier or excipient.

Pharmaceutical compositions may be formulated using conventional methods well-known in the art. The optimal pharmaceutical formulation can be varied depending upon the route of administration and desired dosage. Such formulations may influence the physical state, stability, rate of in vivo release, and rate of in vivo clearance of the administered compounds. Formulation may produce solid, liquid or semi-liquid pharmaceutical compositions.

Pharmaceutical compositions may be formulated in dosage unit form for ease of administration and uniformity of dosage. The expression "unit dosage form", as used herein, refers to a physically discrete unit of chlorotoxin agent for the patient to be treated. Each unit contains a predetermined quantity of active material calculated to produce the desired therapeutic effect. It will be understood, however, that the total dosage of the composition will be decided by the attending physician within the scope of sound medical judgment.

As mentioned above, in certain embodiments, the chlorotoxin agent is administered intravenously through injection or infusion. Pharmaceutical compositions suitable for administration by injection or infusion may be formulated according to the known art using suitable dispersing or wetting agents, and suspending agents. The pharmaceutical composition may also be a sterile injectable solution, suspension or emulsion in a non-toxic diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspension medium. For this purpose, any bland fixed oil can be used including synthetic mono- or di-glycerides. Fatty acids such as oleic acid may also be used in the preparation of injectable formulations.

Injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from injection. This may be accomplished by dissolving or suspending the active ingredient in an oil vehicle. Injectable depot forms are made by forming micro-encapsulated matrices of the drug in biodegradable polymers such as polylactide-polyglycolide. Depending on the ratio of drug to polymer and the nature of the particular polymer employed, the rate of drug release can be controlled. Depot injectable formulations can also be prepared by entrapping the drug in liposomes or microemulsions that are compatible with body tissues.

III. Methods of Detecting

A. Administration

In another aspect, the present invention provides methods for in vivo detection of tumor metastases. For example, it may be desirable to use inventive methods to detect tumor metastases in individuals who have or have had at least one primary tumor. Such methods include administering to a patient an effective amount of a labeled chlorotoxin agent described herein, or a pharmaceutical composition thereof, such that specific binding of the labeled chlorotoxin agent to cells in primary tumor tissue and/or metastatic tumor tissue can occur.

Generally, the dosage of a labeled chlorotoxin agent will vary depending on considerations such as age, sex, and weight of the patient, area(s) of the body to be examined, as well as the administration route. Factors such as contraindications, concomitant therapies, and other variables are also to be taken into account to adjust the dosage of the labeled chlorotoxin agent to be administered. This can, however, be readily achieved by a trained physician. In general, a suitable dose of a labeled chlorotoxin agent corresponds to the lowest amount of agent that is sufficient to allow detection of neoplastic tumor tissue in the patient.

For example, in embodiments where the chlorotoxin agent is labeled with $^{131}$I and administered intravenously, dosing of the labeled chlorotoxin agent may comprise administration of one or more doses each comprising about 5 mCi to about 50 mCi, e.g., about 5 mCi to about 40 mCi, or about 10 mCi to about 30 mCi $^{131}$I. For example, one or more doses of $^{131}$I-radiolabeled chlorotoxin agent may be administered that each contain about 10 mCi, about 20 mCi, or about 30 mCi $^{131}$I. In such embodiments, a diagnosis procedure may comprise administration of a single dose of $^{131}$I-radiolabeled chlorotoxin agent or administration of multiple doses, e.g., 2 doses, 3 doses, or 4 doses. Two consecutive doses may be administered at 1 day interval, 2 days interval, 3 days interval, 4 days interval, 5 days interval, 6 days interval, 7 days interval, or more than 7 days interval.

In embodiments where a $^{131}$I-radiolabeled chlorotoxin agent is used, the patient may be administered supersaturated potassium iodide prior to administration of the $^{131}$I-radiolabeled chlorotoxin (e.g., 1 day, 2 days, or 3 days before treatment according to the present invention). Administration of supersaturated potassium iodide blocks uptake of $^{131}$I by the thyroid gland, thus preventing conditions such as hypothyroidism.

Following administration of the labeled chlorotoxin agent and after sufficient time has elapsed for specific binding to take place, detection of the bound labeled chlorotoxin agent is performed.

In some embodiments, a second effective amount of a labeled chlorotoxin agent is administered at a second time period and binding of the labeled chlorotoxin agent in the individual's body is measured. Measurement of binding after the second administration of labeled chlorotoxin agent may allow assessment of any change in binding (e.g., in extent and/or location of binding), which may be indicative of progression, stability, and/or regression of one or more metastases. Subsequent (i.e., third, fourth, etc.,) administrations of effective amounts of a labeled chlorotoxin agent during subsequent time periods to obtain additional measurements may also be performed. This may be desirable, for example, to assess the progression, stability, and/or regression of one or more metastases over a longer period of time.

In some embodiments, the length of time between consecutive administrations of effective amounts of a labeled chlorotoxin agent varies. In some embodiments, administrations of a labeled chlorotoxin agent are performed at approximately regular intervals. In some embodiments, timing of administration matches or parallels the timing of a dosing regimen that the patient undergoes for treatment.

B. Metastasis Detection and Localization

As will be recognized by one skilled in the art, detection of binding of a labeled chlorotoxin agent to a tissue of interest may be carried out by any of a wide variety of methods including, but not limited to, spectroscopic, photochemical, biochemical, immunochemical, electrical, optical or chemical means. Selection of a detection method will generally be based on the nature of the labeling moiety of the agent (i.e., fluorescent moiety, radionuclide, paramagnetic metal ion, and the like). In certain embodiments, detection and localization of one or more metastases within a patient are carried out using an imaging technique.

Different imaging techniques can be used depending on the nature of the labeling moiety. For example, the binding may be detected using Magnetic Resonance Imaging (MRI) if the labeling moiety comprises a paramagnetic metal ion (e.g., $Gd^{3+}$). Single Photon Emission Computed Tomography (SPECT) and/or Positron Emission Tomography (PET) can be used for binding detection if the labeling moiety comprises a radioisotope (e.g., $^{131}$I, and the like). Other imaging techniques include gamma camera imaging.

According to detection methods of the present invention, a tissue other than the tissue of the primary tumor is identified as a metastasis if the level of binding of the labeled chlorotoxin agent to the tissue of interest is elevated compared to the level of binding of the labeled chlorotoxin agent to a normal tissue. As already mentioned above, a normal tissue is herein defined as a non-neoplastic tissue. For example, when the method is performed in vivo, the level of binding of the labeled chlorotoxin agent measured in a region of an organ of interest (e.g., the brain) may be compared to the level of binding of the labeled chlorotoxin agent measured in a normal region of the same organ.

In certain embodiments, the tissue of interest is identified as a neoplastic tissue if the level of binding measured is higher than the level of binding to a normal tissue. For example, the level of binding may be at least about 2 times higher, at least about 3 times higher, at least about 4 times higher, at least about 5 times higher, at least about 10 times higher, at least about 25 times higher, at least about 50 times higher, at least about 75 times higher, at least about 100 times higher, at least about 150 times higher, at least about 200 times higher, or more than 200 times higher than the level of binding to a normal tissue.

EXAMPLES

The following examples describe some of the modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

Chlorotoxin Binds Melanoma Metastasized to the Brain and Lung

The experiments described in this Example demonstrate that chlorotoxin binds to melanoma that has metastasized to the brain and/or the lung in biopsy sections.
Materials and Methods Frozen or paraffin sections of human biopsy tissues were histochemically stained with a chemically synthesized form of chlorotoxin containing a detectable biotin group chemically attached to the N terminus (TM-601). Samples of human tissue were from both sexes and different ages and races. Most samples were obtained through the Cooperative Human Tissue Network, Tissue Procurement at UAB (the University of Alabama at Birmingham), UAB hospitals, and the Human Brain Tissue Bank in London, Canada. Snap frozen tissue and fresh tissue embedded in a freezing gel were sliced at 8 microns and picked up onto positively charged glass slides. The sections were then fixed in 4% paraformaldehyde or Milloniqs solution (composed of 4% formaldehyde, 0.4% NaOH, and 7% methanol in a buffered sodium phosphate solution) according to the staining protocol. Paraffin blocks were sectioned and prepared according to standard procedures.

Biopsy sections were blocked for 1 hour in 10% normal goat serum in PBS and treated with a dilution of biotinylated chlorotoxin overnight at 4° C. After thorough rinsings, the stainings were developed by the avidin-biotin complex (ABC) system (Vectastain Elite ABC Kit from Vector Laboratories, Burlignton, Calif.) and visualized by the colorimetric reaction of DAB (3,3'-diaminobenzidine, Vector Laboratories) with the ABC complex.

The biopsy sections were counterstained with methyl green, a nuclear dye, to visualize unstained cells. Non-specific background label can vary from experiment to experiment due to changes in the effective concentration of the label, condition of the tissue, or the duration of the reaction. Therefore, a control section was identically stained with methyl green but without the biotinylated chlorotoxin. Positive cell staining was defined by chlorotoxin-labeling above background when compared to an adjacent control section. Cells containing high amounts of endogenous peroxidase exhibit dark background staining in the controls due to the reaction of DAB with the peroxidases.

Figure 1:
FIG. 1 depicts photomicrographs showing that biotinylated chlorotoxin binds melanoma cells that have metastasized to the brain. Photomicrographs depict staining of adjacent sections as follows: "TM-601," section stained with biotinylated chlorotoxin detected by a brown reaction product of DAB with biotin and further counterstained with methyl green; "Control," section stained with only methyl green; and "H&E," section stained with hematoxylin and eosin.
Figure 1:
Figure 1:
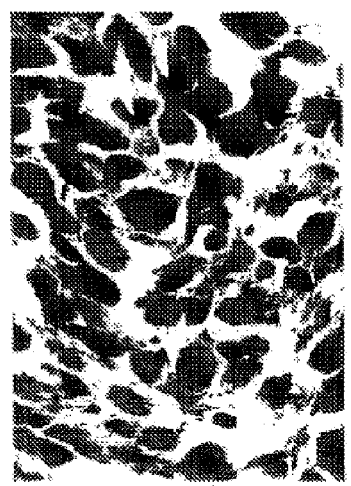
Figure 2:
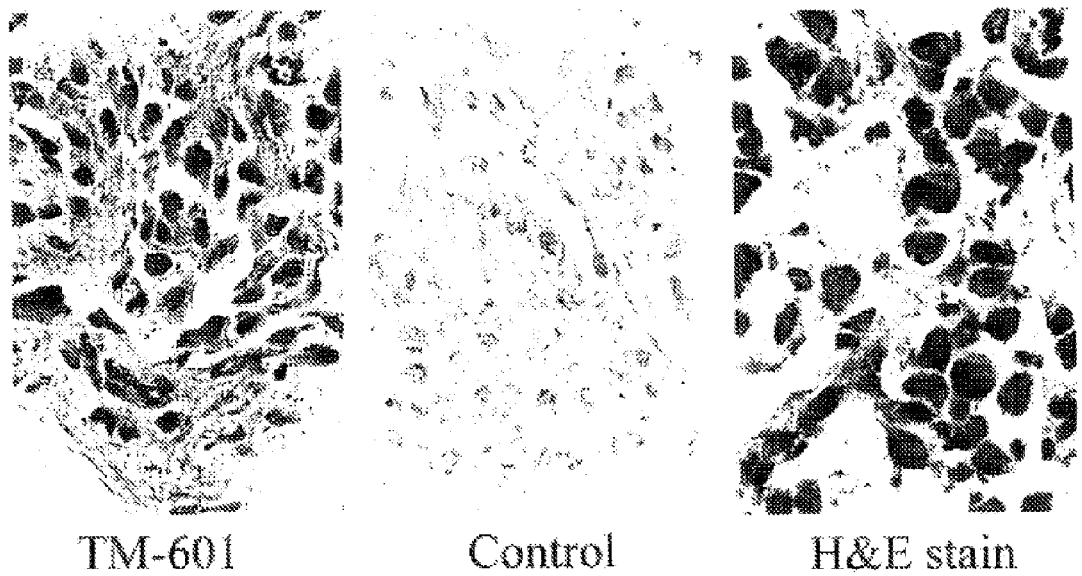
FIG. 2 depicts photomicrographs showing that biotinylated chlorotoxin binds melanoma tumor cells that have metastasized to the lung. Photomicrographs depict staining of adjacent sections as follows: "TM-601," section stained with biotinylated chlorotoxin detected by a brown reaction product of DAB with biotin and further counterstained with methyl green; "Control," section stained with only methyl green; and "H&E," section stained with hematoxylin and eosin.
Figure 3:
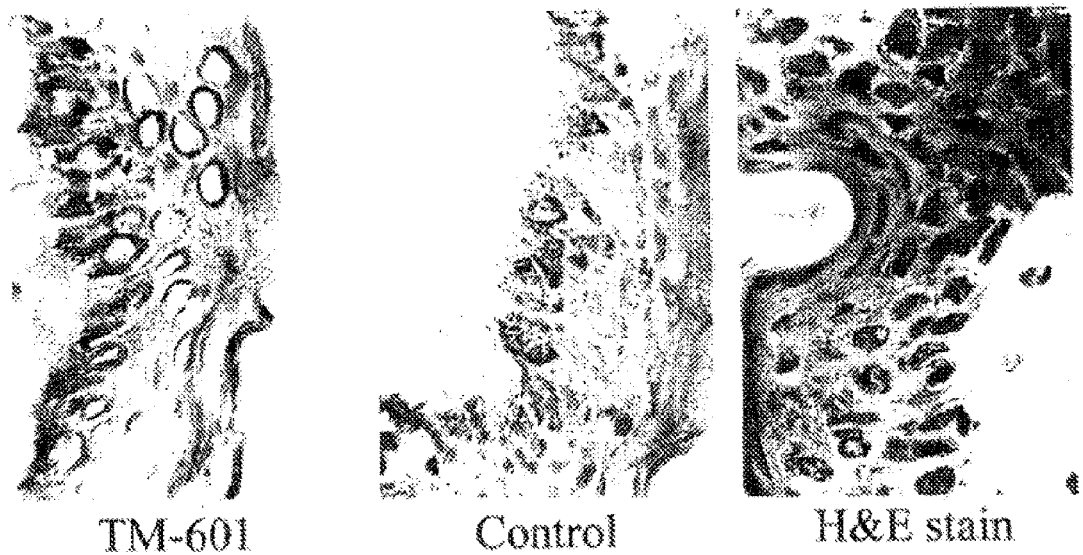
FIG. 3 depicts photomicrographs of adjacent sections of normal skin stained as follows: "TM-601," section stained with biotinylated chlorotoxin detected by a brown reaction product of DAB with biotin and further counterstained with methyl green; "Control," section stained with only methyl green; and "H&E," section stained with hematoxylin and eosin.

A third adjacent section was stained with both hematoxylin (which stains cell nuclei) and eosin (which stains cytoplasm). Therefore, for each tissue analyzed, three adjacent sections were stained.
Results FIG. 1 depicts photomicrographs showing that biotinylated chlorotoxin stains melanoma metastasized to the brain. Eleven out of 11 melanoma brain metastases were positive for TM-601, and 5 out of 5 primary melanoma tumors were positive. In addition, chlorotoxin also binds to melanoma metastasized to the lung (FIG. 2). On the other hand, normal skin is unreactive to TM-601 (6/6 negative) (FIG. 3), although there is some background staining in melanocytes even in controls.

Example 2

Phase I Imaging and Safety Study of Intravenous $^{131}$I-TM-601 in Patients with Recurrent or Refractory Somatic and/or Cerebral Metastatic Solid Tumors The present Example describes preliminary results from a Phase I trial conducted at 5 clinical sites. In this clinical trial, TM-601 was administered intravenously to 48 patients. This multi-center, open-label, non-randomized, sequential "within subject" escalation study included patients with histologically confirmed primary solid tumor malignancy, either recurrent or refractory, who had demonstrated unequivocal evidence of detectable metastatic involvement that was not amenable to standard therapy.

Figure 4:
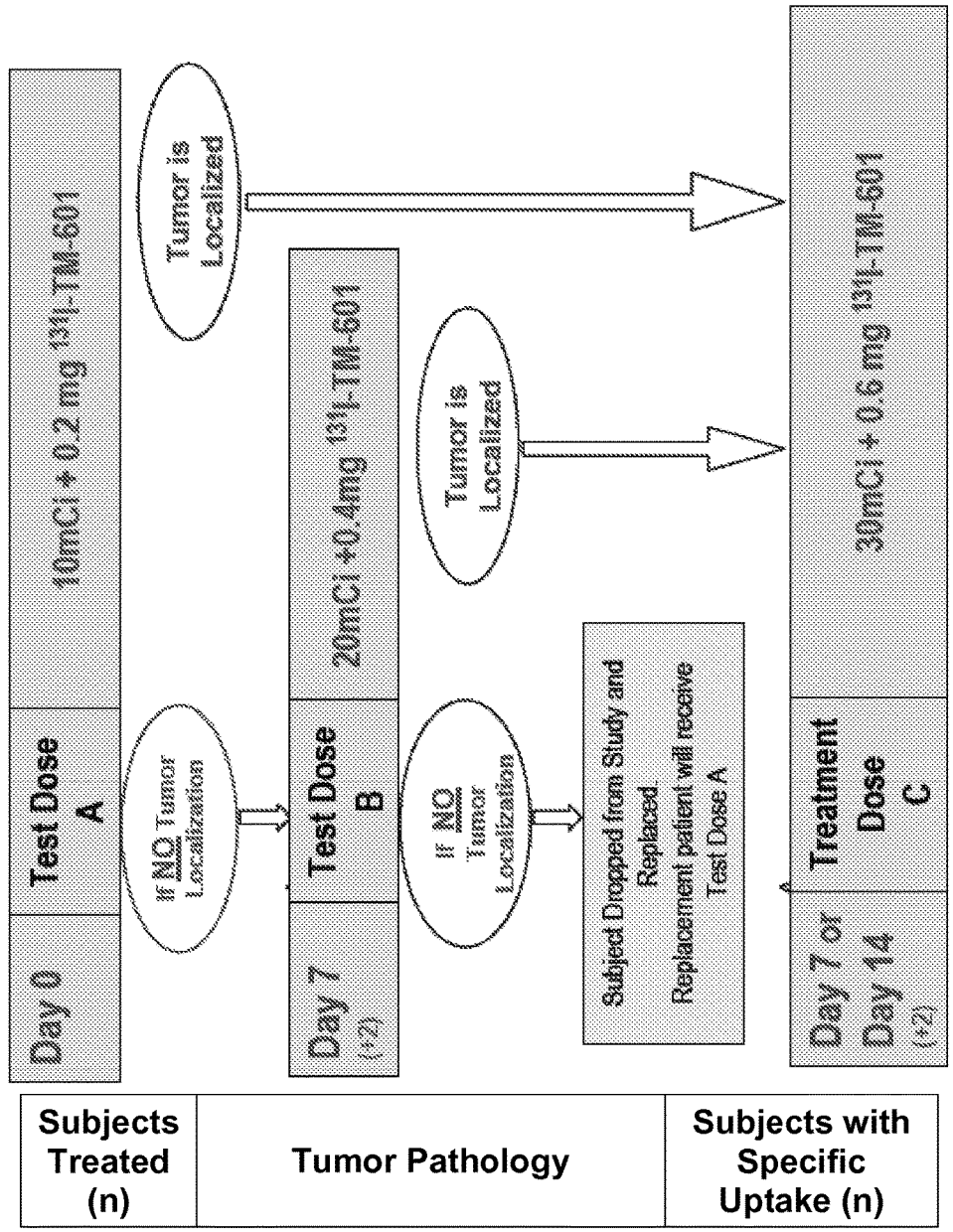
FIG. 4 is the dosing scheme used in the Phase I imaging and safety study of intravenous $^{131}$I-TM-601 in patients with recurrent or refractory metastatic solid tumors.
Figure 6:
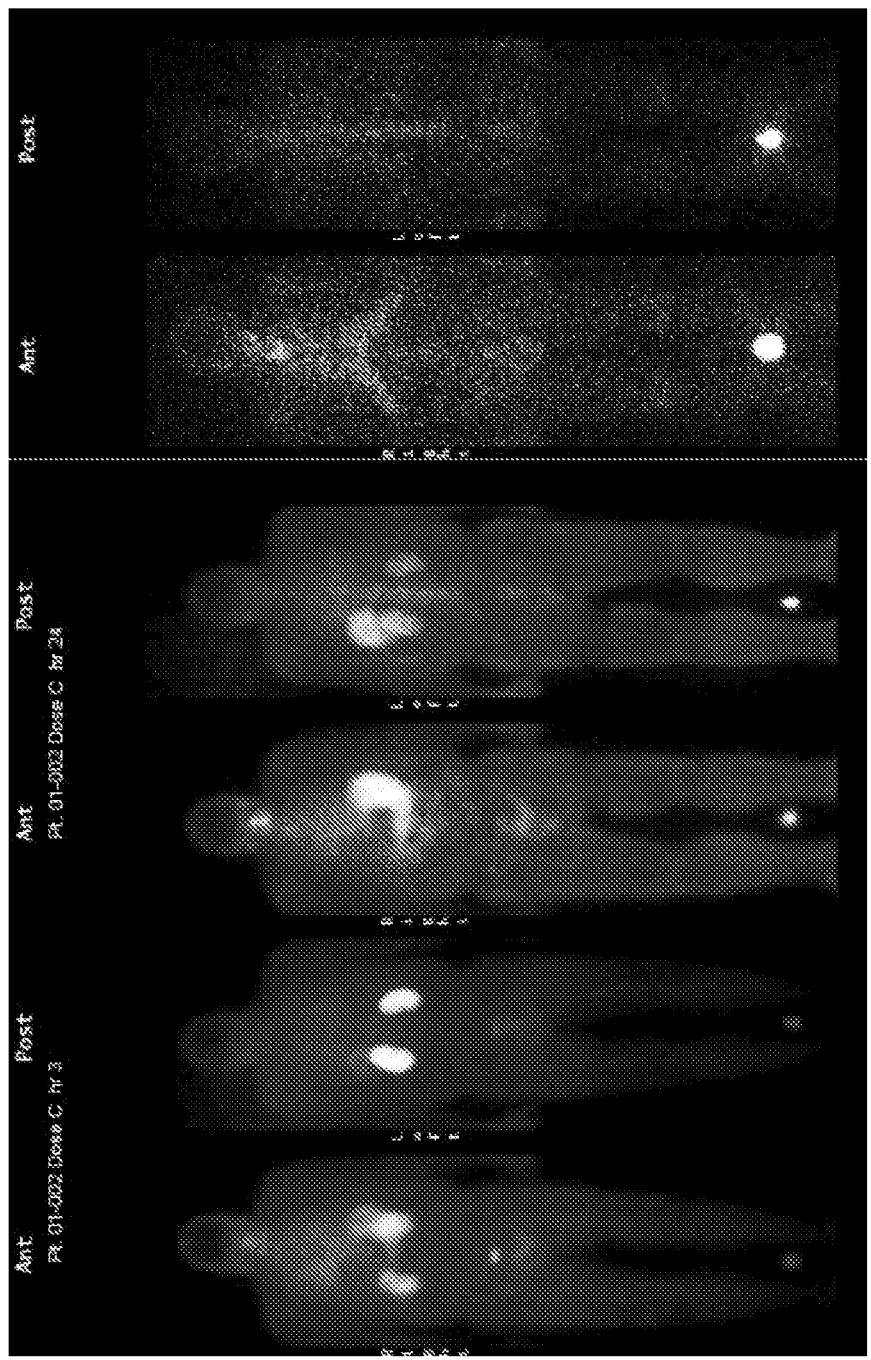
FIG. 6 shows gamma camera images recorded 3 hours, 24 hours, and 7 days after intravenous injection of $^{131}$I-TM-601 (30 mCi/0.6 mg) to a patient with metastatic prostate cancer with known diffuse bone metastases.
Figure 7:
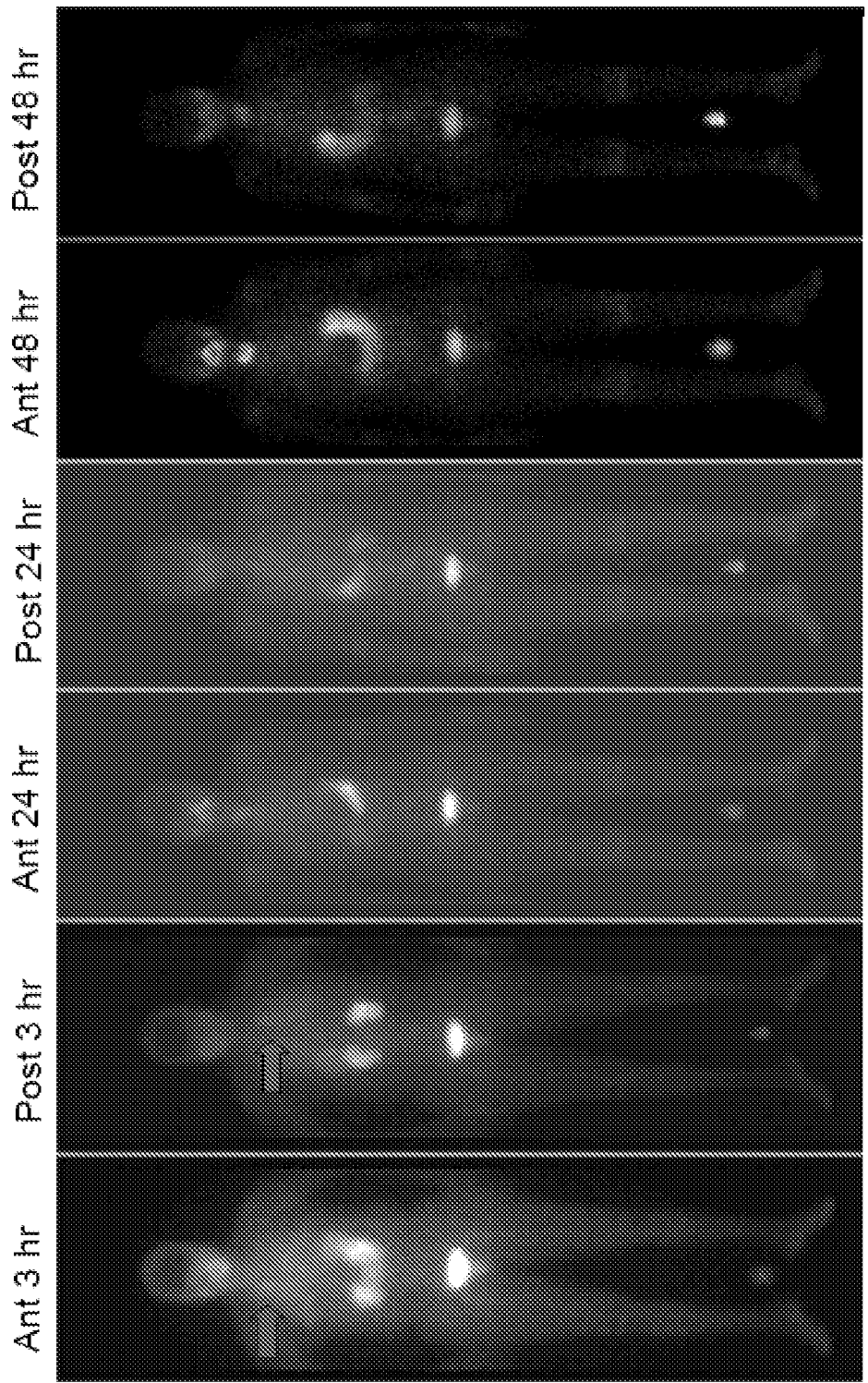
FIG. 7 shows gamma camera images recorded 3 hours, 24 hours, and 48 hours after intravenous injection of $^{131}$I-TM-601 (30 mCi/0.6 mg to) a patient with metastatic non-small cell lung cancer.
Figure 8:
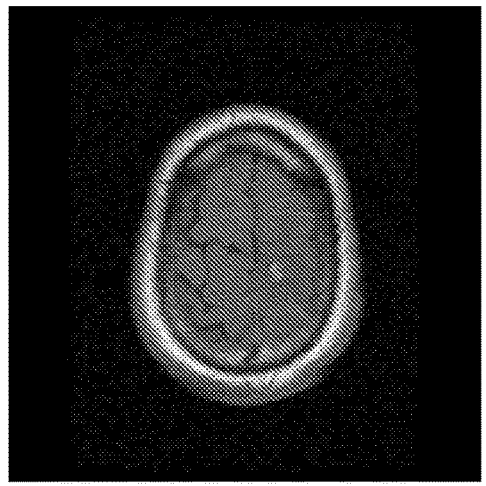
FIG. 8 shows Magnetic Resonance and SPECT images.
Figure 8:
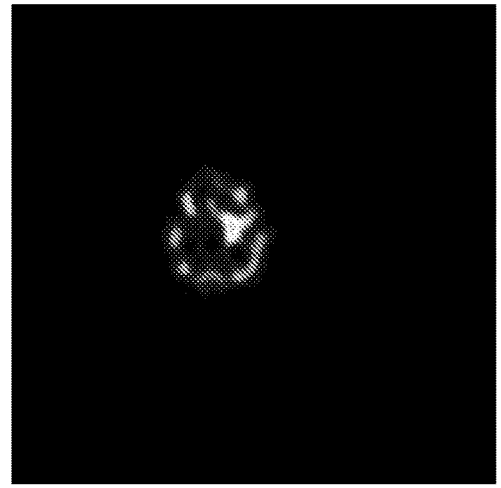
Figure 8:
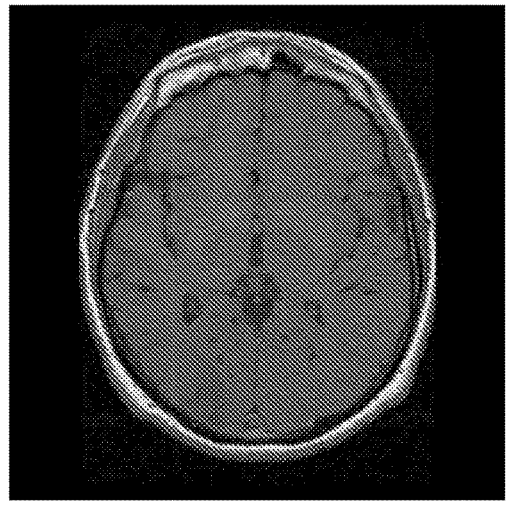
Figure 8:
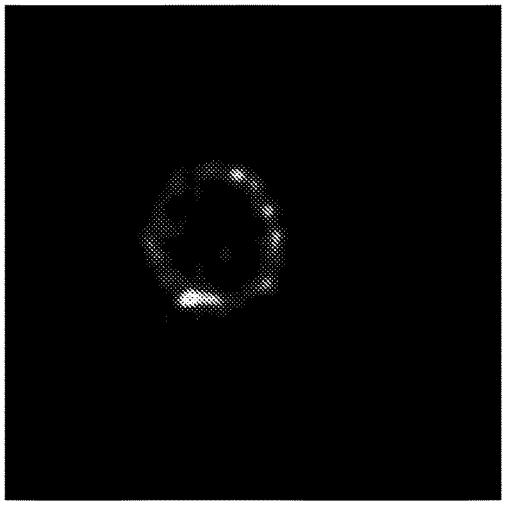
Figure 9:
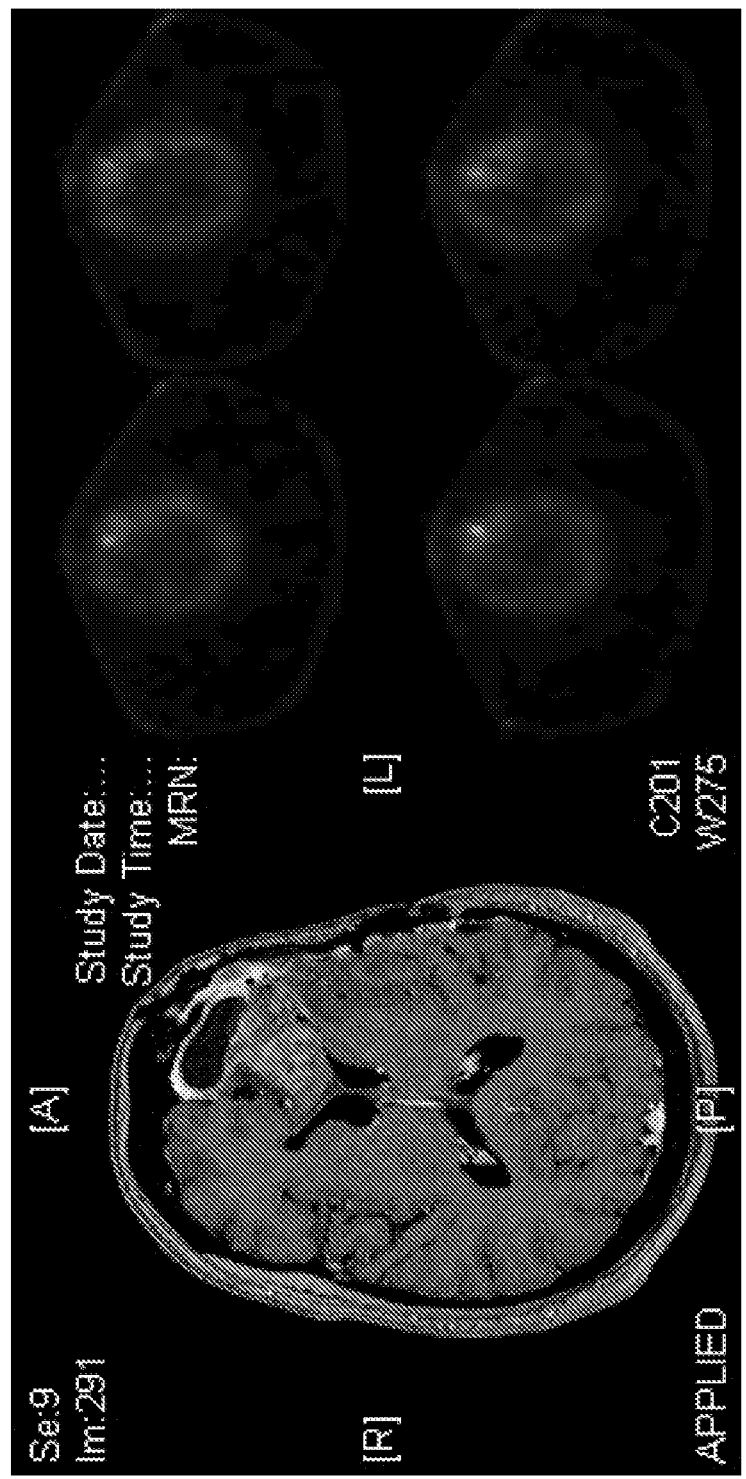
FIG. 9 shows a pre-treatment MRI showing left frontal tumor of a patient with malignant glioma (left), and SPECT scans taken 48 hours after intravenous injection of $^{131}$I-TM-601 to the patient (right).

The objectives of this Phase I study were: a) to evaluate whether intravenous $^{131}$I-TM-601 provides tumor-specific localization in patients with recurrent or refractory metastatic (including brain metastases) solid tumors; b) to determine the distribution and dosimetry of intravenously administered $^{131}$I-TM-601; and c) to determine the safety and tolerability of intravenously administered $^{131}$I-TM-601.
Patients and Treatment Protocol Forty-eight subjects were enrolled in this study. Protocols described below were used with these subjects. Subjects underwent 1 to 2 escalating intravenous doses of $^{131}$I-TM-601 followed by a series of whole body scans to determine whether the $^{131}$I-TM-601 has localized to target tumor cells, and one intravenous therapeutic dose of $^{131}$I-TM-601 once tumor-specific uptake of $^{131}$I-TM-601 was demonstrated. The graphic in FIG. 4 illustrates the dosing scheme. Study patients received up to three doses of $^{131}$I-TM-601 (ranging from 10 mCi/0.2 mg to 30 mCi/0.6 mg) by intravenous (IV) infusion. Only patients demonstrating tumor specific uptake of $^{131}$I-TM-601 by imaging performed 24 hours after administration of the 10 or 20 mCi dose were administered the 30 mCi dose of $^{131}$I-TM-601.
Preparation of $^{131}$I-TM-601

The final TM-601 drug product is a sterile, lyophilized white to off-white powder vialed in stoppered glass vials. The imaging and therapeutic doses used in this trial were doses of radio-labeled TM-601.

TM-601 final drug product was reconstituted in 0.56 mL of radio-labeling buffer to yield a 1 mg/mL solution radio-labeled with $^{131}$I, and delivered to the clinical site. The syringe contained approximately 4 mL of solution for infusion and was approximately labeled as to content and amount of radioactivity. Once received at the site, the radiation safety officer or other appropriate site personnel confirmed that the radiation count of the $^{131}$I-TM-601 was within prescribed specifications. The syringe containing the final radio-labeled drug product was shielded and then transferred to the appropriate hospital area for administration to the patient. The $^{131}$I-TM-601 solution was stored protected from light at 2-8° C. and shielded until use. After radio-labeling with $^{131}$I, the product was recommended to be used within 24 hours.

Administration of $^{131}$I-TM-601 and Imaging Study

All patients receiving the radio-labeled test dose, $^{131}$I-TM-601, received supersaturated potassium iodide (SSKI) at a dose of 300 mg/day orally, beginning on the day of and just prior to radio-labeled $^{131}$I-TM-601 infusion and for a minimum of three days to block uptake of $^{131}$I to the thyroid and other organs. SSKI was dispensed to the patient prior to study drug administration with instructions provided to the patient on the proper use of the drug while not in the clinic/hospital.

The syringe containing $^{131}$I-TM-601 was inserted "piggy-back" fashion into an infusion port within six-inches of the intravenous needle/catheter. While running 0.9% sodium chloride at 100 mL/hour, the product was administered by "slow IV push" over approximately 5-10 minutes. $^{131}$I-TM-601 infusion was terminated if any of the following were observed: (1) a fall in systolic blood pressure>25 mmHg, (2) a significant respiratory distress documented by the investigator, (3) temperature>102° F., (4) seizures, (5) changes in level of consciousness or onset of new neurological deficit, or other reasons, such as clinician's judgment or patient's request.

Imaging by gamma camera and in some cases SPECT was performed 24 hours post $^{131}$I-TM-601 administration to determine localization and eligibility for receiving the 30 mCi dose of $^{131}$I-TM-601.

Safety Results

As of May 2008, a total of 22 serious adverse events were reported for 17 patients. All SAEs were judged by the Investigator to be "unlikely" or "unrelated" to the study drug and four of these events occurred in two patients following consent who did not go on to receive $^{131}$I-TM-601 study drug. A fifth event occurred in a patient prior to receipt of study drug who later was successfully dosed.

Efficacy Results

Tumor specific uptake was observed in a variety of tumor types following intravenous administration, including seven out of eight patients with malignant glioma; two out of two patients with metastatic prostate cancer including one with diffuse bone metastases; three out of five patients with metastatic non-small cell lung cancer; seven out of eight patients with metastatic melanoma; six out of eight patients with metastatic colon cancer; two of three patients with metastatic pancreatic cancer; one out of four patients with metastatic breast cancer; one patient with metastatic transitional cell carcinoma; one patient with metastatic paraganglioma, and one patient with pleomorphic xanthoastrocytoma (as summarized in FIG. 5; see also FIGS. 6-9).

All patients received a test dose of 10 mCi (0.2 mg peptide)$^{131}$I-TM-601 intravenously. Five sequential, whole body gamma camera images were acquired at immediate ≤60 minutes), 3 hours, 24 hours, 48-72 hours, and 168 hours post $^{131}$I-TM-601 injection for tumor localization and dosimetry analysis. Patients showing tumor localization by gamma camera or SPECT imaging received a second therapeutic dose of 30 mCi (0.6 mg peptide)$^{131}$I-TM-601 one week later. Patients not showing uptake were re-treated a week later with 20 mCi (0.4 mg peptide)$^{131}$I-TM-601 to determine possible localization at a higher dose.

Figure 10:
FIG. 10 depicts MRI images from a glioma patient taken before treatment (left panel) and 3 weeks after a dose of 30 mCi of $^{131}$I-TM-601 (right panel) delivered systemically. The patient exhibited a significant reduction in enhancing tumor volume and edema.
Figure 10:
Figure 11:
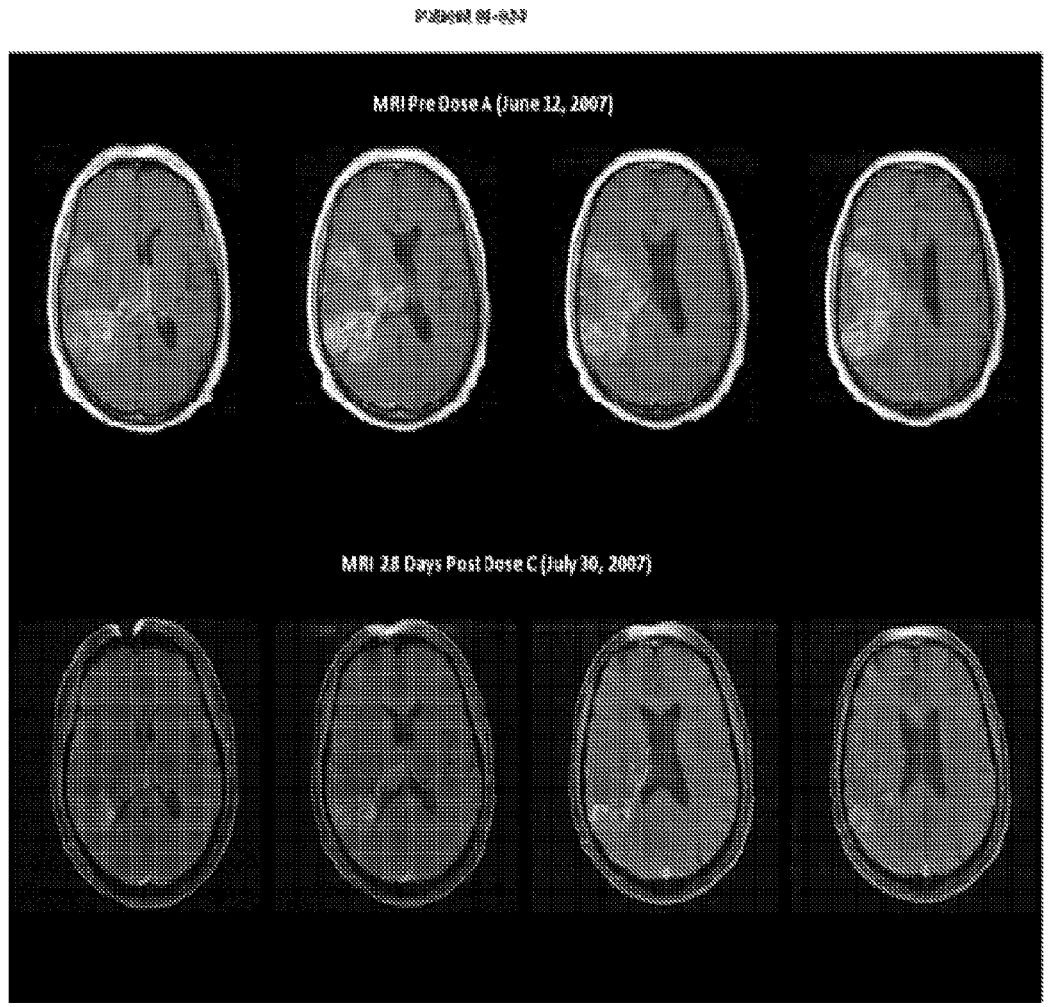
FIG. 11 depicts MRI images from another glioma patient taken before treatment (top panel) and three weeks after a dose of 30 mCi of $^{131}$I-TM-601 (bottom panel) delivered systemically. The patient exhibited a significant reduction in enhancing tumor volume and edema.

Tumor response (as defined by a decrease in the volume of gadolinium-enhancing disease) has been seen in magnetic resonance imaging (MRI) of two of the eight glioma patients at the day 28 evaluation, which demonstrated a measurable reduction in tumor volume from baseline. (see FIGS. 10 and 11).

Figure 12:
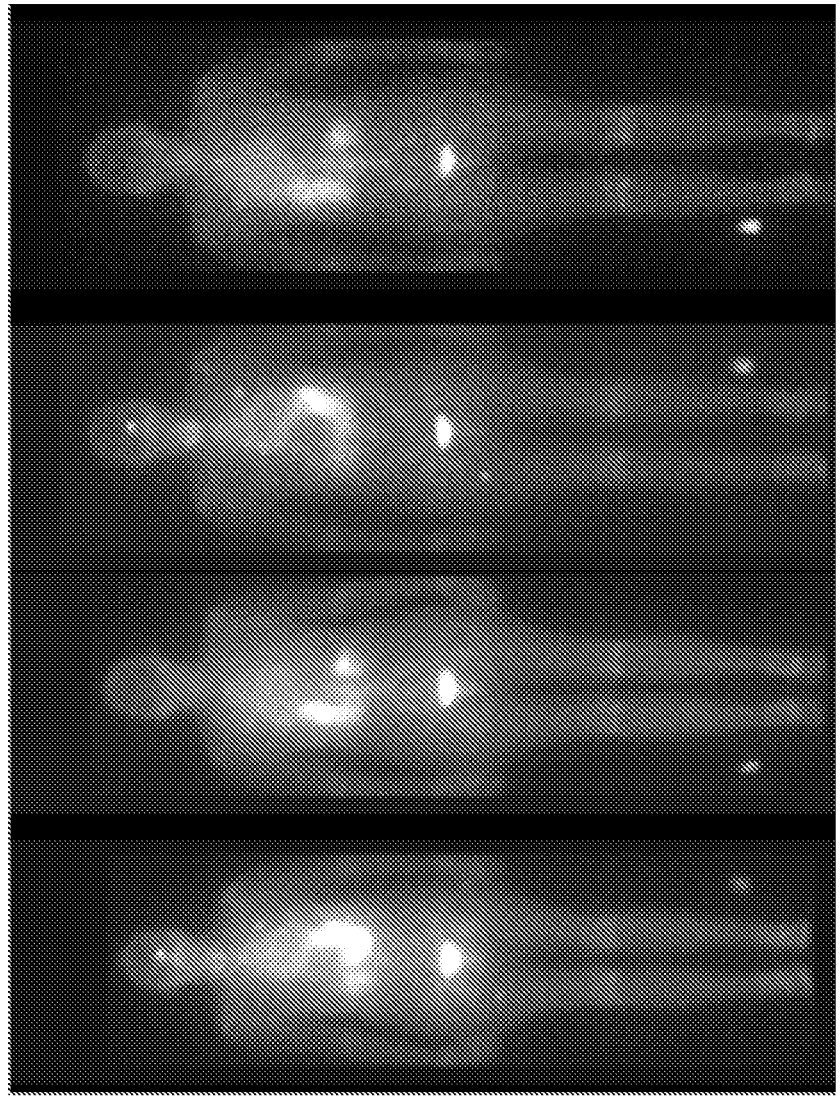
FIG. 12 shows gamma camera images recorded 24 and 48 hours (anterior and posterior views) after intravenous injection of $^{131}$I-TM-601 (30 mCi/0.6 mg) to a patient with metastatic melanoma. Uptake of $^{131}$I-TM-601 was observed in known distant metastases to the brain, lung, liver, and subcutaneous nodules.

These results demonstrate the therapeutic effect of chlorotoxin agents such as $^{131}$I-TM-601 delivered systemically in vivo. These results also demonstrate that $^{131}$I-TM-601 administered intravenously will cross the blood brain barrier and can result in MRI imaging improvement in patients with inoperable gliomas. Furthermore, in patients with metastatic cancers, $^{131}$I-TM-601 delivered intravenously is able to target distant metastases (see, e.g., FIG. 12).

Example 3

Tumor-Specific Targeting of Intravenous $^{131}$I-Chlorotoxin ($^{131}$I-TM-601) in Patients with Metastatic Melanoma In previous clinical trials, patients with recurrent glioblastoma multiforme were administered $^{131}$I-chlorotoxin locally into a tumor resection cavity. In the present Example, distribution of intravenously (IV) administered $^{131}$I-chlorotoxin was examined to determine if the intravenous route of administration would be feasible and would result in intratumoral uptake in patients with metastatic melanoma, including metastases to the CNS. The experiments described in this Example demonstrate that $^{131}$I-chlorotoxin delivered intravenously localizes to tumor sites throughout the body as well as to metastases in the brain. Thus, $^{131}$I-chlorotoxin administered intravenously crosses the blood brain barrier and may be used to target distant metastases.

Materials and Methods

Seven patients with metastatic melanoma were enrolled in the prospective clinical trial of systemically administered $^{131}$I-chlorotoxin discussed in Example 2. The present Example discusses in greater detail the results with these seven patients. All patients received a test dose of 10 mCi (0.2 mg peptide)$^{131}$I-chlorotoxin intravenously. Five sequential whole body gamma camera images were acquired immediately (≤60 minutes) and 3 hours, 24 hours, 48-72 hours, and 168 hours post $^{131}$I-chlorotoxin injection for tumor localization and dosimetry analysis. Patients showing tumor localization by gamma camera or SPECT imaging received a second therapeutic dose of 30 mCi (0.6 mg peptide) $^{131}$I-chlorotoxin one week later. Patients not showing uptake were re-treated a week later with 20 mCi (0.4 mg peptide) $^{131}$I-chlorotoxin to determine possible localization at a higher dose.

Results

Six of the seven enrolled patients with melanoma demonstrated tumor-specific localization on follow-up gamma camera or SPECT imaging after intravenous administration of $^{131}$I-chlorotoxin. Tumor localization was observed in the central nervous system and at extracranial sites. (See FIG. 13 for an example.) The remaining patient was withdrawn from study following the first test dose (10 mCi/0.20 mg peptide) and was not considered evaluable. Dose limiting toxicity was not observed. Full dosimetric analysis was available on three patients treated at the University of Alabama at Birmingham. The mean radiation dose was approximately 0.24 cGy/mCi (ranging from approximately 0.21 to approximately 0.27 cGy/mCi) to total body and approximately 2.56 cGy/mCi (ranging from approximately 1.36 to approximately 4.43 cGy/mCi) to tumor with a calculated therapeutic ratio of approximately 10 (tumor dose/body dose).

The results demonstrate that $^{131}$I-chlorotoxin administered intravenously crosses the blood brain barrier and produces a high rate of tumor specific targeting. Thus, $^{131}$I-chlorotoxin may be used to target distant metastases including those in the brain. Future clinical trials will evaluate the safety and efficacy of higher doses of intravenously administered $^{131}$I-chlorotoxin in a variety of tumor types.

Example 4

Inhibition and Regression of Choroidal Neovascularization by TM-601

The formation of new blood vessels (angiogenesis) and maintenance of such blood vessels is thought to be an important element of metastasis. In the present Example, the ability of chlorotoxin to inhibit angiogenesis and/or cause regression of existing newly formed blood vessels was evaluated using a choroidal neovascularization assay. When TM-601 was administered beginning around the time of induction of blood vessel formation, TM-601 caused a significant decrease in new blood vessel formation. In an experimental paradigm in which TM-601 was administered several days after blood vessel formation was induced, TM-601 caused significant regression of choroidal neovascularization.

Materials and Methods

Choroidal neovascularization (CNV) was induced in mice by photocoagulation with a 530 nm laser. Three burns were delivered to each retina in the 9, 12, and 3 o'clock positions of the posterior pole of the retina. Rupture of Bruch's membrane was judged to be successful when a bubble was produced at the time of laser induction. Only burns for which bubbles were observed were included in this study.

In the first experiment, intravitreal injection of 1 µL of a 50 mg/mL solution of TM-601 dissolved in saline was injected in one eye (n=17 animals, 49 quantifiable burns) and 1 µL of saline was injected in the fellow eye following laser photocoagulation (n=17 animals, 44 quantifiable burns). Seven days later, the injections were repeated. On day 14 of the study, mice were perfused with fluorescein-labeled dextran (2×10$^6$ average molecular weight, Sigma) and choroidal flat mounts were prepared and examined by fluorescence microscopy.

In the second experiment, laser photocoagulation was performed on day 1. One group of 10 mice (30 quantifiable burns) were perfused with fluorescein-labeled dextran on day 7 for CNV baseline measurement prior to treatment initiation. The remainder of the mice received an intraocular injection of 1 µL of a 50 mg/mL solution of TM-601 in one eye (n=12 animals, 34 quantifiable burns) and saline in the fellow eye (n=13 animals, 32 quantifiable burns). On day 14, all remaining mice were perfused with fluorescein-labeled dextran and choroidal flat mounts were prepared and examined by fluorescence microscopy.

Sizes of choroidal neovascularization lesions were measured in choroidal flat mounts. After perfusion with fluorescein-labeled dextran, eyes were removed and fixed for 1 hour in 10% buffered formalin. The cornea and lenses were removed and the entire retina was dissected from the eye cup. Radial cuts of the choroids were made from the edge to the equator and the eyecup was flat mounted. Flat mounts were examined by fluorescence microscopy and images were digitized. Image-Pro Plus software (Media Cybernetics) was used to measure the total area of choroidal neovascularization associated with each burn.

Results

Figure 13:
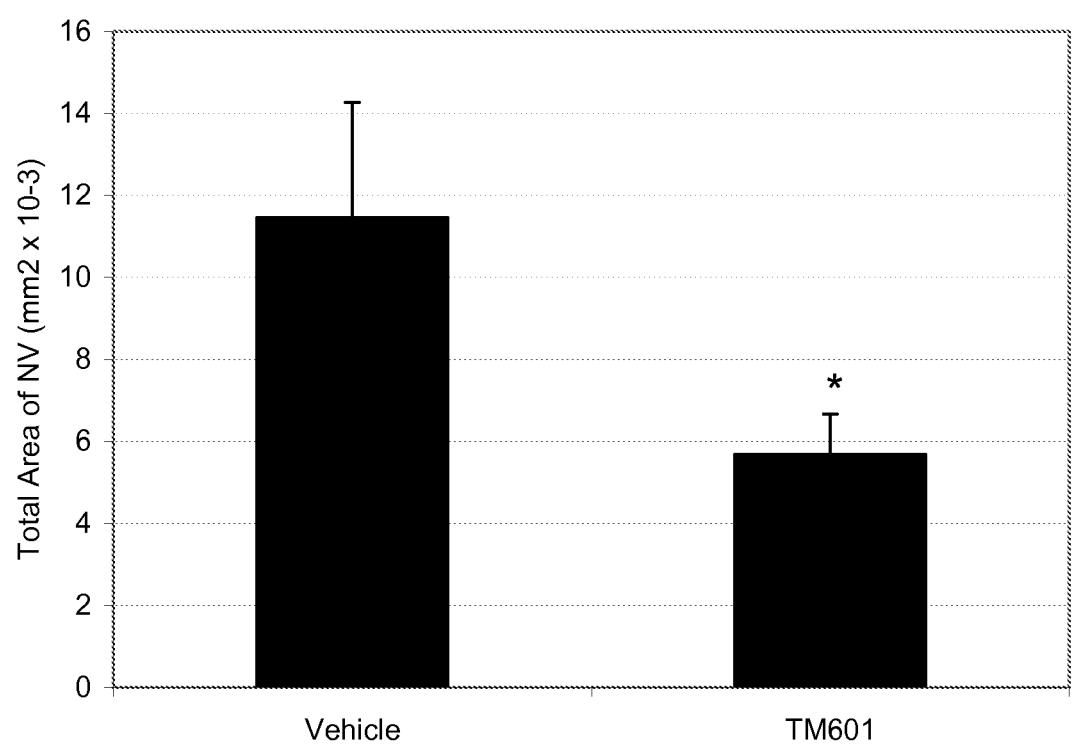
FIG. 13 depicts results from experiments testing the ability of TM-601 to inhibit blood vessel formation in a mouse model of choroidal neovascularization (CNV). Total area of neovascularization (NV) in mm$^2$×10$^{-3}$ is shown for animals receiving either TM-601 or saline vehicle. A statistically significant decrease in choroidal neovascularization was observed in animals receiving intraocular injections of 50 µg TM-601 on the day of disruption of Bruch's membrane and on day 7 ($*p<0.05$). Choroidal lesions were analyzed on day 14.
Figure 15:
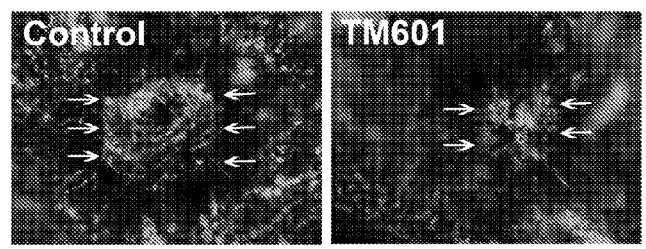
FIG. 15 depicts representative microscope images showing that intravitreal injection with TM-601 led to decreased blood vessels at the site of laser-induced blood vessels in a mouse model of choroidal neovascularization. Neovascularization was inhibited when TM-601 was administered the same day as laser induction (top panel). Existing neovasculature regressed when TM-601 was administered 7 days after laser induction (bottom panel). On day 14, all mice were perfused with fluorescein-labeled dextran and choroidal flat mounts were prepared and examined by fluorescence microscopy.
Figure 15:
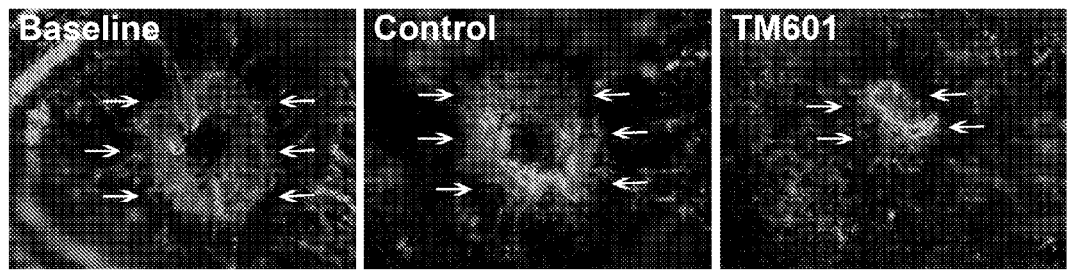

Rupture of Bruch's membrane with laser photocoagulation in mice causes choroidal neovascularization (CNV), which mimics many aspects of CNV that occurs in patients with neovascular age-related macular degeneration. To determine whether TM-601 impacts the formation of new blood vessels in this model, intravitreal injections of 50 µg TM-601 were performed on the day of laser photocoagulation (day 1) and on day 7. Control eyes were injected with saline at the same time points. Fourteen days after rupture of Bruch's membrane, choroidal flat mounts from each eye were analyzed. TM-601 treatment was found to significantly decrease the formation of new blood vessels with intraocular TM-601 doses of 50 µg (FIGS. 13 and 15).

Figure 14:
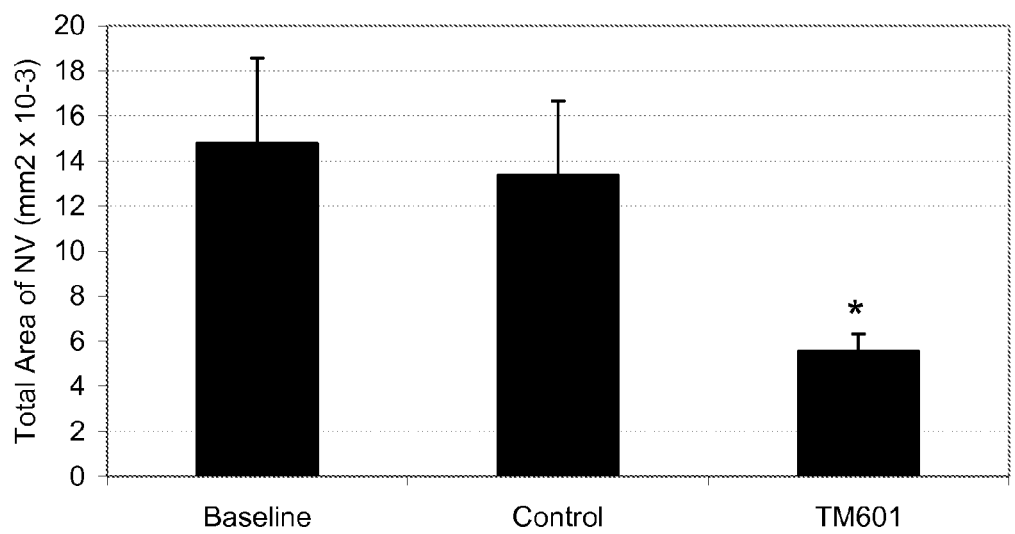
FIG. 14 depicts results from experiments testing the ability of TM-601 to cause regression of existing neovessels in a mouse model of CNV. Total area of neovascularization (NV) in mm$^2$×10$^{-3}$ is shown for animals receiving either TM-601 or saline vehicle. "Baseline" refers to the measurement taken at day 7 after disruption of Bruch's membrane (i.e., before treatment with TM-601). A statistically significant regression of choroidal neovascularization was observed in animals receiving intraocular injections of 50 µg TM-601 on the day 7 ($*p<0.05$). For "control" and "TM-601" values, choroidal lesions were analyzed on day 14.

To assess the effect of TM-601 on pre-existing neovasculature in this model, treatment with intraocular injection with 50 µg TM-601 was delayed until 7 days after disruption of Bruch's membrane. At this time point, large sites of neovascularization were already present (see baseline in FIG. 14). A single saline injection on day 7 had no effect on new blood vessel formation measured on day 14 (control in FIG. 14), whereas a single injection of TM-601 significantly caused regression of CNV (FIGS. 14 and 15).

Discussion/Conclusion

The present Example demonstrates that locally administered TM-601 can significantly suppress CNV and cause regression of CNV. The CNV mouse model mimics the disease state for the wet form of macular degeneration. The intravitreal route of administration used in this study may be clinically relevant, since it is the route used for administering Lucentis®, a clinically approved therapy for macular degeneration.

Example 5

TM-601 Inhibits Angiogenesis in a Mouse CNV Model Via Various Routes of Delivery The experiments described in the present Example were conducted to evaluate anti-angiogenic ability of TM-601 delivered by various routes of administration. A choroidal neovascularization assay was used to measure new blood vessel growth around sites of laser-induced rupture of Bruch's membrane and to determine whether local or systemic administration of TM-601 cause decreased angiogenesis. Three new routes of administration were tested: periocular (also referred to as subconjunctival), intravenous, and topical (eye drops).

Materials and Methods

Choroidal neovascularization (CNV) in mice was induced by 530 nm laser photocoagulation. Three burns were delivered to each retina in the 9, 12 and 3 o'clock positions of the posterior pole of the retina. Successful rupture of Bruch's membrane was evident when production of a bubble occurred at the time of the laser induction. Only burns in which a bubble was observed were included in the study.

Dosing

Periocular injections of 5 μL TM-601 solution were performed with TM-601 concentrations of 2, 10, 50 and 200 mg/mL dissolved in saline. Five microliters of saline was injected in the fellow eye following laser photocoagulation. Seven days later, injections were repeated. On day 14 of the study, mice were perfused with fluorescein-labeled dextran ($2\times10^6$ average molecular weight, Sigma) and choroidal flat mounts were prepared and examined by fluorescence microscopy.

Intravenous dosing was performed by tail vein injections at a dose of 20 mg/kg TM-601 three times per week.

Topical application of TM-601 was achieved by application of eye drops three times a day, each eye drop containing a volume of 10 μL TM-601. TM-601 was dissolved in over-the-counter Artificial Tears (Rite Aide) which contains as active ingredients 70% dextran and 0.3% hypromellose. Inactive ingredients include 0.1% benzalkonium, edetate disodium, potassium chloride, purified water and sodium chloride. The final concentrations of TM-601 were 1, 5 and 25 mg/mL to give a single dose of 10, 50, and 250 μg respectively per 10 μL drop.

Histology and Imaging

Sizes of choroidal neovascularization lesions were measured in choroidal flat mounts. After perfusion with fluorescein-labeled dextran, the eyes were removed and fixed for 1 hr in 10% buffered formalin. Cornea and lenses were removed and the entire retina was dissected from the eye cup. Radial cuts of the choroids were made from the edge to the equator and the eyecup was flat mounted. Flat mounts were examined by florescence microscopy and images were digitized. Image-Pro Plus software (Media Cybernetics) was used to measure the total area of choroidal neovascularization associated with each burn.

Results

Rupture of Bruch's membrane with laser photocoagulation in mice causes choroidal neovascularization (CNV), which mimics many aspects of CNV that occurs in patients with neovascular age-related macular degeneration. Using this model, the inventors had previously shown that intraocular injections of TM-601 significantly decreases neovascularization and also causes regression of new blood vessels. (See Example 4).

Figure 16:
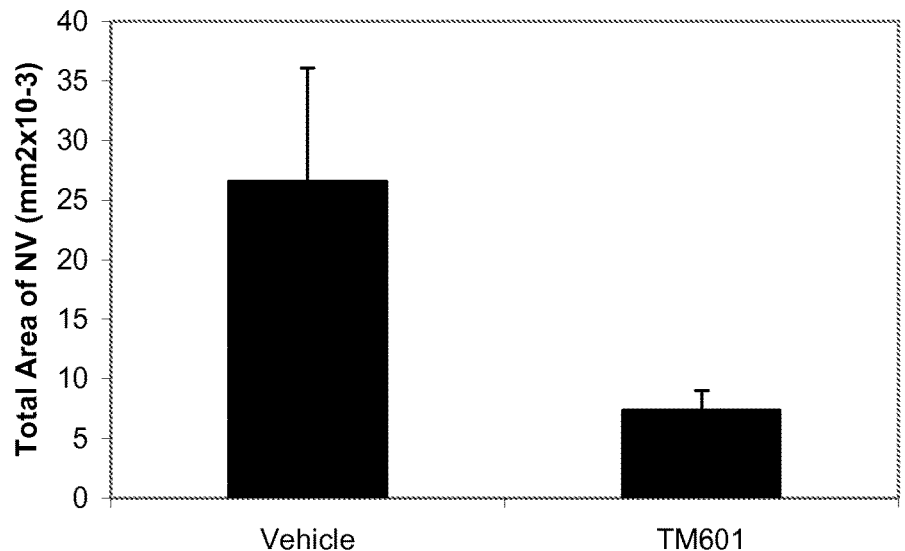
FIG. 16 depicts experimental results showing a Statistically significant decrease in choroidal neovascularization in animals receiving periocular injections of 250 µg TM-601 on the day of disruption of Bruch's membrane and on day 7 ($*p<0.05$). Choroidal lesions were analyzed on day 14.

In the current study, other routes of administration (periocular, intravenous and topical) were examined. In the first periocular study, periocular injections of 250 μg TM-601 were performed on the day of laser photocoagulation (day 1) and on day 7. Control eyes were injected with saline at the same time points. Fourteen days after rupture of Bruch's membrane, choroidal flat mounts from each eye were analyzed. TM-601 treatment was found to significantly decrease the formation of new blood vessels with periocular TM601 doses of 250 μg (FIG. 16).

Figure 17:
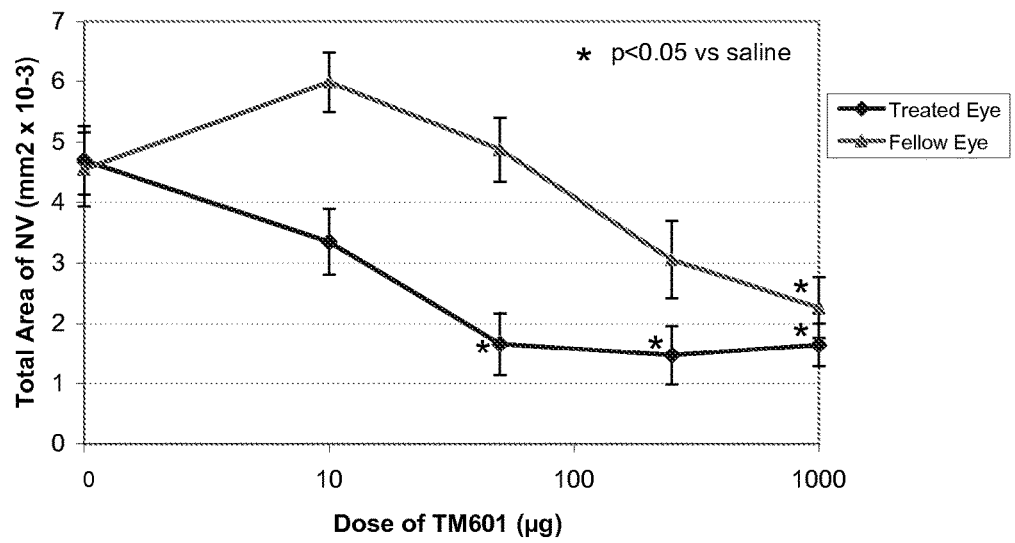
FIG. 17 depicts experimental results showing dose-dependent inhibition of choroidal neovascularization with periocular injections of TM-601 on days 1 and 7 of the study. Choroidal lesions were analyzed on day 14. ($*p<0.05$).

To determine the dose response for periocular injections, TM-601 was injected at a dose of 10 μg, 50 μg, 250 μg or 1000 μg. The 10 μg dose did not significantly decrease choroidal neovascularization, but doses of 50 μg or greater reduced CNV to a similar extent (FIG. 17). Interestingly, fellow eyes in animals that received periocular injections also exhibited reductions in CNV (green curve in FIG. 17).

Figure 18:
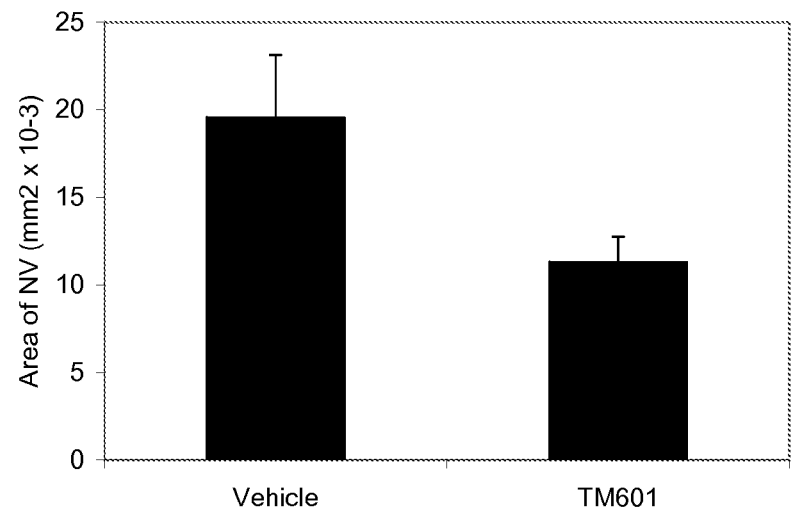
FIG. 18 depicts experimental results showing statistically significant regression of choroidal neovascularization in animals receiving intravenous injections of TM-601 (3× per week at a dose of 20 mg/kg). Choroidal lesions were analyzed on day 14. ($*p<0.05$).

To determine whether systemically injected TM-601 would also penetrate into the choroid and inhibit angiogenesis, TM-601 was injected by tail vein three times per week over the course of the two week study at a dose of 20 mg/kg. With intravenous injections, TM-601 was found to significantly reduce CNV (FIG. 18).

Figure 19:
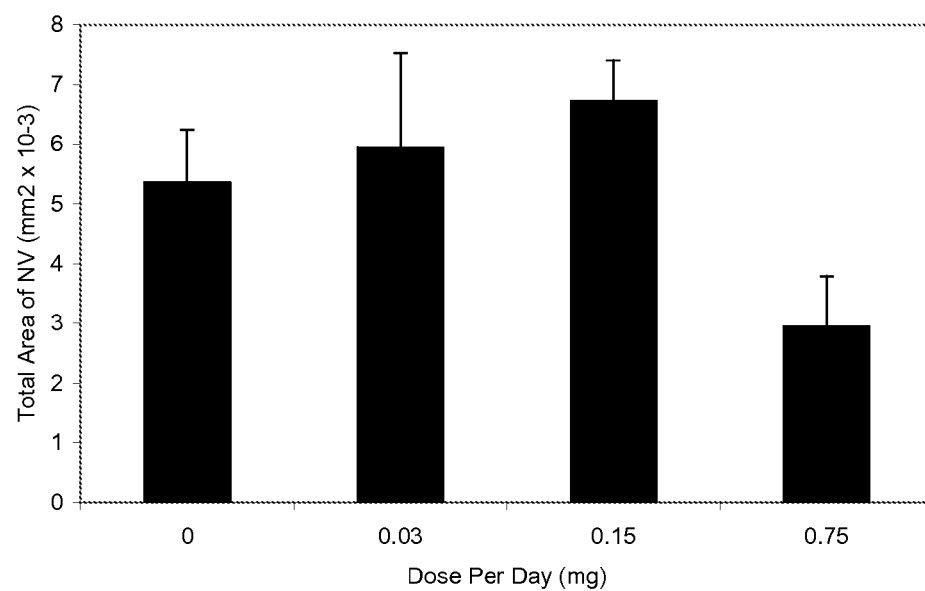
FIG. 19 depicts experimental results showing decreased choroidal neovascularization in animals receiving intravenous topical application of TM-601 (eye drops 3× per day). Choroidal lesions were analyzed on day 14. The difference between areas of NV for eyes that received a dose of 0.75 mg/day TM-601 and eyes that received the saline control reached a p-value of 0.059.

Topical eye drop application, the least invasive of the three routes of administration examined in this Example, was also tested. TM-601 was resuspended in an over-the-counter eye drop lubricant and was applied three times per day via a 10 μL eye drop. At the highest dose delivered (0.25 mg/drop, three times per day), a decline in CNV was observed, but it was not statistically different from the saline control (FIG. 19).

Discussion/Conclusion

The CNV mouse model mimics the disease state for the wet form of macular degeneration. As shown in Example 4, an intravitreal route of administration can significantly decrease choroidal neovascularization. This is the same route used for administering Lucentis®, a clinically approved therapy for macular degeneration. However, the inventors recognized that a less invasive mode of delivery may be advantageous and tested periocular, intravenous and topical delivery of TM-601. In all cases, TM-601 was shown to decrease CNV, although the decrease seen with topical drops was not observed to reach statistical significance. Periocular injections of TM-601 may be advantageous over drugs that require intraocular delivery (e.g. Lucentis®).

The "fellow-eye effect" observed in FIG. 17 may be interesting. TM-601 injected periocularly caused significant reductions in CNV in the adjacent eye (which did not receive injections). Without wishing to be bound by any particular theory, a possible explanation for this phenomenon is that the injected material entered systemic circulation, thus resulting in drug exposure to the fellow eye. A similar fellow-eye effect was not observed with topical eye drops.

These results indicate that TM-601 delivered by different routes of administration showed anti-angiogenic effects, thus providing further support for chlorotoxin's utility as a therapeutic agent for metastatic cancers.

Example 6

Localization of TM-601 to New Blood Vessels and TM-601-Induced Apoptosis of Neovascular Endothelial Cells Experiments described in Examples 4 and 5 demonstrated that chlorotoxin can inhibit angiogenesis and cause regression of new blood vessels in a mouse model of choroidal neovascularization (CNV). Experiments described in the present Example were directed to understanding the mechanism of chlorotoxin's anti-angiogenic effects as demonstrated in Examples 4 and 5. Results in the present Example demonstrated that TM-601 localizes to new blood vessels and induces apopotosis of neovascular endothelial cells in a mouse CNV model. Furthermore, results in the present Example demonstrated that TM-601 colocalizes with Annexin A2, which the inventors have observed in previous studies to bind to TM-601, in areas of neovascularization in both a CNV model and a retinopathy model.

Although TM-601 was shown to inhibit choroidal neovascularization and regression of newly formed vessels in the eye, it was not previously known whether TM-601 directly bound to a particular cell type in the eye, or was pharmacologically active in a non-specific manner. Generalized binding to the vasculature was not observed in whole body planar images after intravenous injection of $^{131}$I-TM-601. It was therefore hypothesized, without wishing to be bound by any particular theory, that TM-601 selectively binds only to a subset of activated or proliferating cells at a site of new blood vessel formation.

New blood vessel formation was induced in a mouse model of CNV, and the location of TM-601 after intravitreal or subconjunctival injection in such a model was determined. In addition, a TUNEL assay was used to determine whether regression of new blood vessels was due to apoptosis of endothelial cells at the site of choroidal neovascularization.

To further understand the mechanism of TM-601's anti-angiogenic effects, colocalization of TM-601 with chlorotoxin's likely cellular receptor, Annexin A2, in areas of neovascularization was examined by immunohistochemistry. Annexin A2 has been observed by the inventors to bind to TM-601. Annexin A2 is expressed on surfaces of endothelial cells and is overexpressed in certain tumor types. Annexin A2 has been characterized as a docking station that regulates the conversion of pro- and/or anti-angiogenic proteins such as plasminogen and plasmin.

Materials and Methods

Choroidal neovascularization (CNV) in mice was induced by 530 nm laser photocoagulation. Three burns were delivered to each retina in the 9, 12 and 3 o'clock positions of the posterior pole of the retina. Successful rupture of Bruch's membrane was evident when production of a bubble occurred at the time of the laser induction. Only burns in which a bubble was observed were included in the study.

Dosing

Intraocular injections of 1 µL TM-601 (50 µg/µL dissolved in saline) were performed on day 7 following CNV lesion. Subconjunctival injections of 5 µL were performed on days 7 and 8 using a TM-601 concentration of 10 µg/µL dissolved in saline. No injections were given to the fellow eye. Animals were sacrificed on day 9, the eyes were removed, and sections were cut through CNV lesions. Frozen sections were stained as described below.

Immunohistochemistry

For TM-601 localization studies, rabbit anti-TM-601 (red in FIGS. 20A, B, and C and FIGS. 21A, B, and C) primary antibody was used. Fluorescence detection was performed using a fluorescent-tagged anti-rabbit IgG secondary antibody. Sections were also stained with fluorescently tagged GSA lectin (green in FIGS. 20D, E, and F and FIGS. 21D, E, and F) to identify endothelial cells. For detection of apoptotic cells, sections were stained for Terminal deoxynucleotidyl Transferase dUTP Nick End Labeling (TUNEL). This assay is used to detect cell nuclei that exhibit DNA fragmentation, a hallmark of apoptotic cell death. Sections were also stained with a nuclear stain. For colocalization studies with Annexin A2, sections were also stained with anti-Annexin A2.

Endothelial Cell Proliferation Assay

Endothelial cell proliferation assay was performed using the CellTiter 96® Aqueous One Solution Cell Proliferation Kit from Promega (catalogue number #G3582). Briefly, either 4,000 cells (72 hr assay) or 1,000 cells (120 hr assay) were plated overnight in each well of a 96 well tray. The next day, TM-601 or diluent was added to the wells. The cells were then cultured for either 72 or 120 hrs at 37° C. Cell number was determined by staining with MTS tetrazolium according to kit protocol. The quantity of formazan product as measured by the absorbance at 490 nm is directly proportional to the number of living cells in culture.

Results

Figure 20:
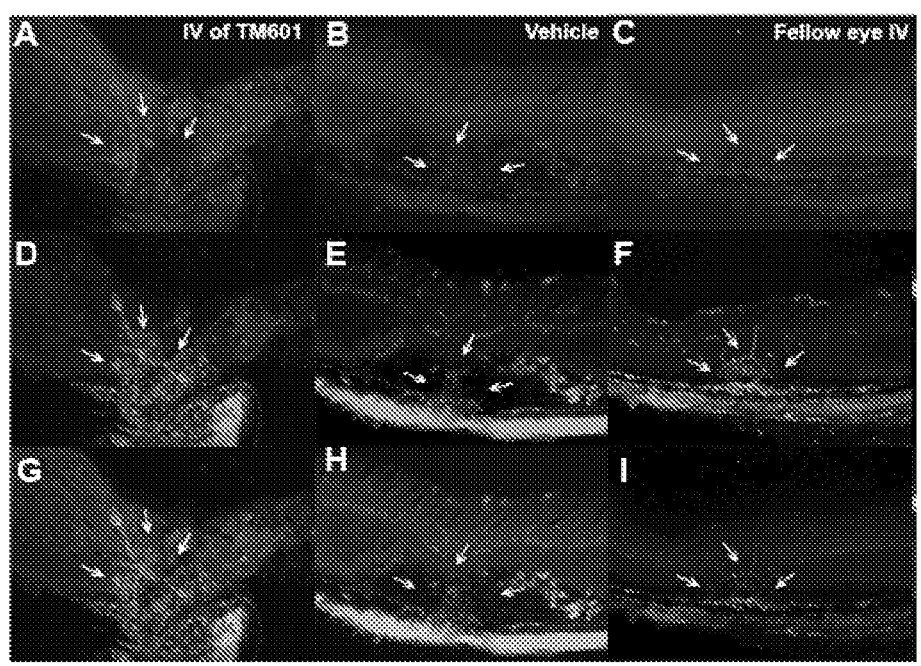
FIG. 20 depicts microscope images of frozen sections showing localization of TM-601 in CNV areas after intraocular injection of TM-601. TM-601 was injected on day 7 after laser-induced rupture of Bruch's membrane. Mice were euthanized on day 9. Frozen sections were stained with rabbit anti-TM-601 (red in A, B and C) and with a GSA lectin (green in D, E, and F) to visualize endothelial cells. Eyes injected with vehicle (B, E, and H) and eyes that were not injected (C, F, and I) did not show positive stained cells within the CNV area. On the contrary, sections from eyes treated with TM-601 (A, D, and G) showed prominent staining for TM-601 throughout the area of CNV (A and D). Coregistration of red and green staining is shown on the bottom row (G, H and I). Arrows show the CNV area.
Figure 21:
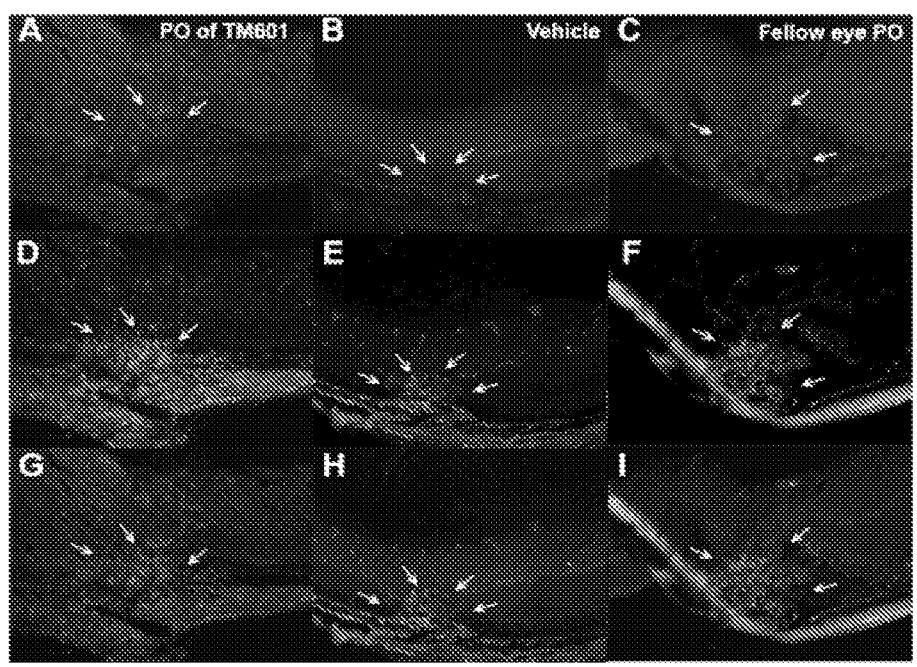
FIG. 21 depicts microscope images of frozen sections showing localization of TM-601 in CNV areas after periocular injection of TM-601. TM-601 was injected, mice were euthanized, and frozen sections were stained as described for FIG. 16. (See also Materials and Methods in Example 6). Staining with rabbit anti-TM-601 is visualized as red in A, B and C and staining with a GSA lectin (to visualize endothelial cells) is visualized as green in D, E, and F. Eyes injected with vehicle (B, E, and H) and eyes that were not injected (C, F, and I) did not show positive stained cells within the CNV area. On the contrary, sections from eyes treated with TM-601 (A, D, and G) showed prominent staining for TM-601 throughout the area of CNV (A and D). Coregistration of red and green staining is shown on the bottom row (G, H and I). Arrows show the CNV area.

To investigate the mechanism of TM-601's antiangiogenic effects in a mouse model of CNV, localization of TM-601 was studied by injecting TM-601 intraocularly into mouse eyes on day 7 or periocularly on days 7 and 8 after laser-induced photocoagulation. On day 9 of the study, eyes were immunostained for TM-601. With both routes of administration, TM-601 was found to specifically localize to endothelial cells in the choroid (FIGS. 20 and 21). No detectable TM-601 was observed to be associated with pre-existing vessels below the retinal layer, indicating that TM-601 bound selectively to newly formed vessels in the choroid.

Figure 22:
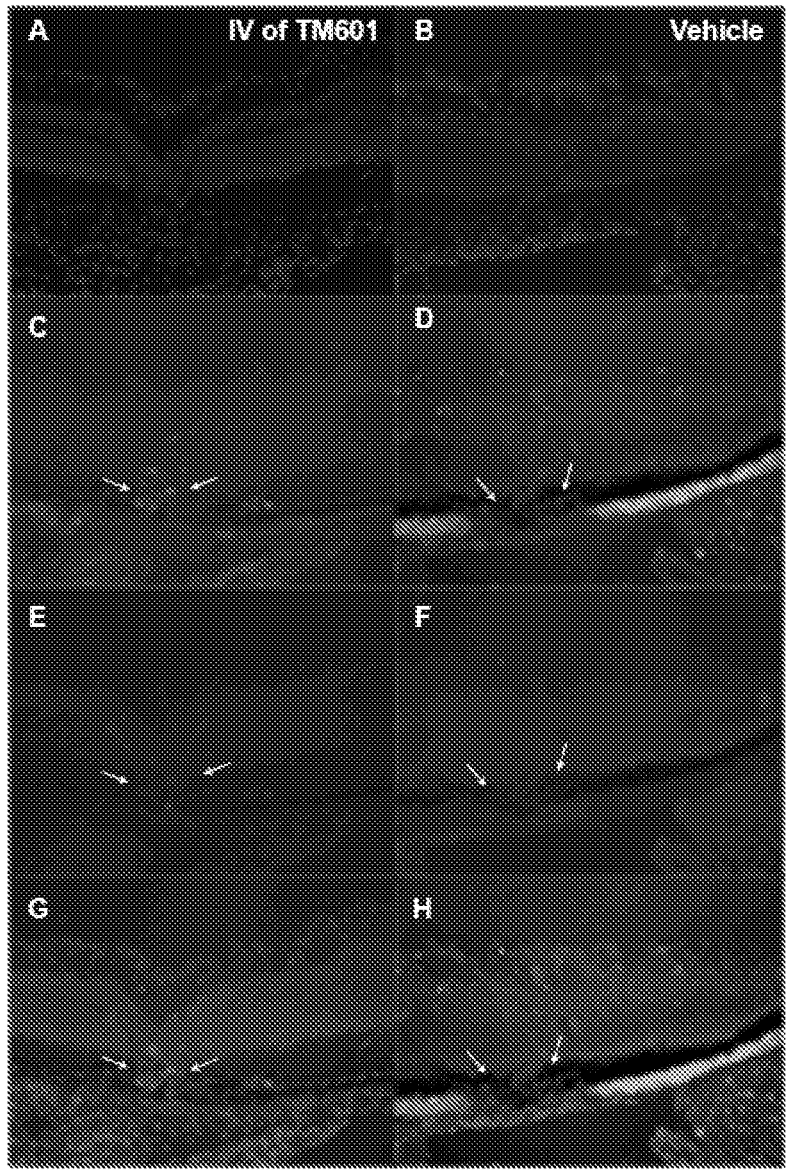
FIG. 22 depicts microscope images of frozen sections showing the effect of TM-601 on apoptosis within CNV lesions by intraocular injection. TM-601 was injected and mice were euthanized as described for FIG. 16. (See also Materials and Methods in Example 6). Sections were stained with nuclear stain (A, B) GSA (C, D) and TUNEL (E, F).

As described in Example 4, one week after new blood vessel formation as a result of laser photocoagulation, a single intraocular injection of TM-601 caused significant regression of CNV. However, the mechanism of this effect was unknown. To test whether TM-601 could cause apoptosis of cells that contribute to the newly forming vasculature in this model, sections cut through CNV lesions were stained for TUNEL. Apoptotic cells (as identified by positive TUNEL staining) co-localized with an endothelial stain, indicating that endothelial cells in the region of choroidal neovascularization were undergoing apoptosis following either intraocular or periocular TM-601 treatment (FIGS. 22 and 23). No apoptosis was detected in eyes injected with saline. Apoptosis of endothelial cells in treated eyes in vivo was unexpected because in vitro treatment of cultured endothelial cells with TM-601 is not cytotoxic over a wide range of TM-601 concentrations (FIG. 24).

To further understand the mechanism of TM-601's anti-angiogenic effects, colocalization studies were conducted with TM-601 and Annexin A2, chlorotoxin's likely cellular receptor. Neovascularization was induced in the eye in two different models, choroidal neovascularization induced by laser disruption of Bruch's membrane and retinopathic neovascularization induced by oxygen-induced ischemia. TM-601 was injected intraocularly as described herein for similar experiments. In both models of neovascularization, TM-601 colocalized with Annexin A2 (FIG. 25).

Discussion/Conclusion

Results presented in this Example support several important findings related to chlorotoxin's anti-angiogenic effects. First, TM-601 injected intraocularly or periocularly selectively binds to endothelial cells in newly formed vasculature in the choroid layer after laser-induced rupture of Bruch's membrane. TM-601 did not bind to pre-existing mature vessels. These results are consistent with the observation $^{131}$I-TM-601 does not indiscriminately bind to all vessels in the body following intravenous injection. Instead, radiolabel is detected predominantly in the region of the tumor due to tumor-specific and/or neovascular-specific binding. Second, binding of TM-601 to endothelial cells results in selective apoptosis of new vessels forming around the site of laser injury, but not in pre-existing vessels. Third, TM-601 colocalizes with Annexin A2, which is involved in regulating the conversion of pro- and/or anti-angiogenic proteins such as plasminogen and plasmin, raising the possibility that chlorotoxin exerts at least some of its anti-angiogenic effects through Annexin A2.

Example 7

Effect of TM-601 on Tumor Cell Migration In Vitro

Experiments described in this Example were directed to elucidating the role of chlorotoxin on cell migration, which plays a major role in metastasis. TM-601 showed a dose-dependent inhibitory effect on cell migration, as assessed by a Transwell invasion assay.

Materials and Methods

Migration of Human Umbilical Vein Endothelial Cells (HUVEC) across a Transwell (Corning, 8 μm) was performed on ~5×10$^4$ serum-starved cells in triplicate. Chemoattractants in the bottom well included VEGF or bFGF (50 ng/ml) in media containing 0.4% FBS. Ten micromolar TM-601 was incubated with the cells for 30 min at room temperature prior to loading cells into the Transwell. After 22 hrs at 37° C., non-migrated cells on the upper surface were removed using a Q-tip. Cells that migrated through the membrane were fixed in methanol and visualized with Giemsa stain. Quantitative counts of invaded cells were performed by superimposing the Transwell over a hemocytometer and counting the number of cells in each of five regions.

Results

As shown in FIG. 26A, TM-601 inhibited cell migration in a dose-dependent manner. Approximately fifty-percent Fewer cells migrated in the presence of TM-601 whether they were stimulated by VEGF or bFGF (FIG. 26B).

Example 8

Effect of TM-601 on MMP2 Activity

As discussed previously, cell migration plays a major role in metastasis. Degradation of the extracellular matrix facilitates cell movement and is a key step in cell migration. In the present example, the effect of TM-601 on matrix metalloproteinase 2 (MMP2), an enzyme that degrades the extracellular matrix, was studied in two different cell types: HUVECs and U87, a glioma cell line. Results from these experiments demonstrated that TM-601 inhibits MMP2 activity.

MMP-2 activity was measured in media taken from cultured HUVEC cells without treatment, treatment with bFGF, or treatment with bFGF together with 10 μM TM-601. (HUVEC cells were cultured as described in Example 7.) As depicted in FIG. 26C, treatment with TM-601 nearly obliterated the increase of MMP2 activity induced by bFGF.

MMP-2 activity was also measured in media taken from cultured U87 cells treated with 10 μM TM-601 or with no TM-601. As depicted in FIG. 27, TM-601 decreases MMP-2 activity secreted from U87 human glioma cells.

These results suggest that TM-601 has an inhibitory effect on MMP-2 activity.

Discussion for Examples 6-8

Taken together, data presented in Examples 6-8 provide a better understanding of the anti-angiogenic effects of TM-601. In cell culture, TM-601 has been shown to bind to proliferating endothelial cells and block cell migration (see Example 7), a critical step in the formation of new blood vessels. Without wishing to be bound by any particular theory, it appears that some form of cellular activation is required in vivo for binding of TM-601 to endothelial cells because only newly formed vessels bind TM-601, whereas quiescent cells in the mature vasculature do not. In addition, proliferating HUVEC cells in culture do not mimic activated endothelial cells of the neovasculature because TM-601 does not decrease the proliferation of HUVEC cells (as would be expected if apoptosis were occurring in vitro). Therefore, the data suggest that one effect of TM-601 on newly forming vasculature is to inhibit formation of new vessels by blocking endothelial cell migration. TM-601 has been observed to exert a second effect in CNV models: newly formed blood vessels that bind TM-601 undergo apoptosis.

In summary, in vitro evidence suggests that TM-601 blocks endothelial cell migration, thus preventing a key early step in angiogenesis. In addition, TM-601 has been shown to cause regression of newly formed vessels via apoptosis in a CNV model.

Results described in these Examples shed light on the mechanism of chlorotoxin's anti-angiogenic properties, which are particularly attractive qualities as regards chlorotoxin's utility as a therapeutic agent against metastatic tumors.

Example 9

Effect of Intravenously Delivered Unlabeled TM-601 on Tumors in Human Patients

Human clinical data presented in this Example examine the ability of intravenously delivered unlabeled TM-601 to treat cancer. As previously discussed, in vitro data demonstrated that TM-601 binds to vascular endothelial cells and blocks endothelial cell migration. The inventors had also obtained in vivo data demonstrating that intravenous infusion of TM-601 decreases neovascularization. These observations prompted initiation of a phase I trial to evaluate the use of intravenously delivered unlabeled TM-601 in an invasive cancer with known hypervascularity, malignant glioma. Primary objectives of this study are: a) to determine the safety and tolerability of TM-601 in adult patients with recurrent malignant glioma; b) to determine the target recommended phase II dose and biologically active dose of TM-601 when administered intravenously based on magnetic resonance (MR) perfusion imaging changes; and c) to determine the pharmacokinetics of TM-601 at each dose level.

Patients and Treatment Protocol

Patients with recurrent malignant glioma eligible for this study are administered 10 mCi/0.2 mg of $^{131}$I-TM-601 by intravenous (IV) infusion to demonstrate tumor specific localization (imaging dose). Only patients demonstrating tumor specific uptake of $^{131}$I-TM-601 on a brain SPECT scan remain on study to receive treatment with non-labeled TM-601. One week after the imaging dose, study patients receive non-labeled TM-601 by intravenous infusion at one of six dose levels (0.04 mg/kg, 0.08 mg/kg, 0.16 mg/kg, 0.3 mg/kg, 0.6 mg/kg, and 1.2 mg/kg) once per week for 3 weeks in a 4 week cycle. Subsequent cycles of non-labeled TM-601 are administered as long as there is no evidence of disease progression and the patient experiences no dose-limiting toxicities. Patients are evaluated at week 4 of each cycle with conventional and dynamic susceptibility contrast MRI to assess perfusion.

As of January 2009, six patients with recurrent malignant glioma had been enrolled in the study and had imaging data available for analysis. With respect to safety, there had been one event of intratumoral hemorrhage which was considered to be possibly related to therapy. Three other serious adverse events considered to be unrelated to therapy included disease progression on therapy, a hip fracture, and renal calculi in a patient with a history of renal calculi. Two of six patients in this first dosing cohort demonstrated a greater than 25% reduction in relative cerebral blood flow (rCBF) and/or relative cerebral blood volume (rCBV) compared to pre-treatment baseline. Both patients with improvement in perfusion MRI parameters had extended response to intravenous TM-601 marked by multiple cycles of therapy without evidence of tumor progression.

These results indicate that unlabeled chlorotoxin shows promise as a therapeutic against an invasive cancer with strong metastatic potential, which in the present Example is malignant glioma.

Example 10

Bioavailability and Anti-Angiogenic Effects of PEGylated Chlorotoxin

In the present Example, PEGylated chlorotoxin was studied to determine if the half-life of chlorotoxin in vivo could be increased. Anti-angiogenic effects of PEGylated chlorotoxin was also examined.

Materials and Methods

PEGylation

TM-601 was PEGylated at the N-terminus of the peptide via reductive animation using a polydispersed, linear, 40 kDa PEG-propionaldehyde (DowPharma).

Half-Life Measurements of TM-601

Non-tumor-bearing C57BL/6 mice were injected with TM-601 (at a dose of approximately 2 mg/kg) intravenously by a single tail vein injection. Blood samples were obtained at various timepoints, and levels of TM-601 were determined by ELISA using an anti-TM-601 antibody.

Mouse Matrigel Plug

Matrigel Matrix High Concentration (from BD Biosciences) was mixed with 100 ng/ml VEGF, 100 ng/ml bFGF, and 3 ng/ml heparin at 4° C. Eight-week old female C57BL/6 mice were randomly assigned to each groups with 6 mice in each group. Each mouse received two 500 µL Matrigel plugs injected bilaterally in subcutaneous tissue. To form a round shaped plug, a wide subcutaneous pocket was formed by swaying the needlepoint right and left after a routine subcutaneous insertion. The injection was performed rapidly with a 21-25G needle to ensure the entire contents were delivered into the plug. Matrigel plugs were implanted on Day 0 of the study and treatment began on Day 1. Animals were dosed with intravenous injections with either vehicle (saline), TM-601, or PEGylated TM-601. Three dosing regimens were used: once a week for two weeks (once on D1 and once on D8; "Q7Dx2"), twice a week for two weeks (on D1, D4, D8, and D11; "Q3Dx2/2"), and five times a week for two weeks (on D1, D2, D3, D4, D5, D8, D9, D10, D11, and D12; "Q1Dx5/2"). Plugs were collected after 14 days. Mice were euthanized and the skin over the plugs was pulled back. Plugs were dissected out, fixed, and embedded in paraffin for histological analysis. Three sections of 5 µm thickness from each evaluable plug were immunostained with a CD31 antibody and counterstained with hematoxylin & eosin. Blood vessel counts in a cross sectional area of each matrigel plug was analyzed under a microscope.

Results/Discussion

As shown in FIG. 28, PEGylated TM-601 exhibited an increased half-life in vivo as compared to unmodified TM-601. PEGylation increased the half life of TM-601 approximate 32-fold, that is, approximately 25 minutes (TM-601) to approximately 16 hrs (TM-601-PEG).

Increased half life translated into the ability to dose the animals less frequently in a model of angiogenesis. In mouse Matrigel plug assays, animals were dosed according to a variety of schedules with either TM-601 or PEGylated TM-601 (TM-601-PEG). Microvessel densities were measured and reduction of such densities was interpreted to signify anti-angiogenic effects.

Both TM-601 and TM-601-PEG had anti-angiogenic effects with the two most frequent dosing schedules tested (twice a week for two weeks, "Q3DX2/2"; and five times a week for two weeks, "Q1Dx5/2") (FIG. 29). Whereas TM-601 did not exhibit any anti-angiogenic effects with the least frequent dosing schedule tested (once a week for two weeks, "Q7DX2") treatment with TM-601-PEG with such a dosing schedule resulted in a significant reduction of microvessel density (FIG. 29).

Without wishing to be bound by any particular theory, the ability to dose animals less frequently may be due to availability of TM-601-PEG for a longer period of time as compared to TM-601. Such increased availability could result in longer exposure at sites of new blood vessel formation, allowing more prolonged effects. These characteristics (e.g., increased availability, prolonged effects, etc.) may be advantageous in treatment of metastatic tumors.

Example 11

Effect of TM-601 on Lung Metastases

In the present Example, the ability of TM-601 to inhibit metastases in the lung is investigated using a mouse model in which melanoma cells are injected into mice. The number of resultant lung metastases in mice with or without treatment with TM-601 is counted.

The B16/F10 mouse melanoma cell line is obtained from ATCC and cultured according to recommended specifications. Each mouse is inoculated intravenously with 0.2 mL of a 0.9% NaCl solution containing a suspension of tumor cells ($1 \times 10^5$ cells/mouse).

Drug injections are administered concurrently with tumor cells according to Table 1 below. Animals receive doses of test article as described in Table 1 below. Animals receive doses daily five times per week for two weeks. Sterile PBS are used as the vehicle control. TM-601 are reconstituted in sterile PBS solution. Following treatment initiation, mouse body weight measurements are recorded twice weekly and gross observations are made at least once daily. All mice are sacrificed from all groups at Day 14 (or upon determination of moribund state) and the number of B16/F10 lung colonies are counted. The counted colonies are visible as black colored lung nodules on a yellow background visible in inflated lungs with Bouin fixative solution instilled via trachea.

TABLE 1

Evaluation of TM-601 as a Single Agent versus pulmonary metastasis of B16/F10 mouse melanoma

| Group Name | N | Vehicle (qd × 5 × 2) | TM-601 (qd × 5 × 2) |
| --- | --- | --- | --- |
| 1. Vehicle* | 5 | X | |
| 2. TM-601 2 mg/kg (IV)* | 5 | | X |
| 3. TM-601 20 mg/kg (IV)* | 5 | | X |

*First dose to be administered concurrently w/tumor cells on Day 0

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method comprising a step of:
systemically administering an effective amount of a chlorotoxin agent to a subject suffering from a primary tumor and at least one metastasis that arose from the primary tumor, which metastasis is located in the brain, wherein the chlorotoxin agent comprises a chlorotoxin peptide whose amino acid sequence is at least 90% identical to that set forth in SEQ ID NO:1, the chlorotoxin agent being characterized in that it selectively targets metastatic cancer cells over normal cells and localizes to the at least one metastasis in the brain upon being systemically administered.

2. The method of claim 1, wherein the systemic administration comprises intravenous administration.

3. The method of claim 1, wherein the systemic administration comprises an infusion or bolus injection.

4. The method of claim 1, wherein the chlorotoxin agent comprises a chlorotoxin peptide associated with at least one therapeutic moiety.

5. The method of claim 4, wherein the chlorotoxin peptide and therapeutic moiety are directly covalently associated.

6. The method of claim 4, wherein the chlorotoxin peptide and therapeutic moiety are fused to form a fusion protein.

7. The method of claim 4, wherein the chlorotoxin peptide and therapeutic moiety are covalently associated through a linker.

8. The method of claim 4, wherein the therapeutic moiety comprises an anti-cancer agent, cytostatic agent, or cytotoxic agent.

9. The method of claim 8, wherein the therapeutic moiety comprises a cytotoxic agent and the cytotoxic agent is selected from the group consisting of toxins, bioactive proteins, chemotherapeutics, antibiotics, nucleolytic enzymes, and radioisotopes.

10. The method of claim 9, wherein the cytotoxic agent comprises a radioisotope.

11. The method of claim 10, wherein the radioisotope comprises $^{131}$I, $^{111}$In, or $^{177}$Lu.

12. The method of claim 8, wherein the therapeutic moiety comprises an anti-cancer agent and the anti-cancer agent is selected from the group consisting of alkylating agents, purine antagonists, pyrimidine antagonists, plant alkaloids, intercalating antibiotics, aromatase inhibitors, anti-metabolites, mitotic inhibitors, growth factor inhibitors, cell cycle inhibitors, enzymes, topoisomerase inhibitors, biological response modifiers, anti-hormones, and anti-androgens.

13. The method of claim 1, wherein the primary tumor is a solid tumor.

14. The method of claim 1, wherein the primary tumor is a refractory tumor.

15. The method of claim 1, wherein the primary tumor is a recurrent tumor.

16. The method of claim 1, wherein the primary tumor is a member of the group consisting of lung cancer, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual or reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, chronic or acute leukemia, lymphocytic lymphomas, cancer of the bladder, cancer of the kidney, renal cell carcinoma, neoplasms of the central nervous system (CNS), neuroectodermal cancer, spinal axis tumors, glioma, meningioma, and pituitary adenoma.

17. The method of claim 1, wherein the primary tumor is a tumor of neuroectodermal origin.

18. The method of claim 17, wherein the tumor of neuroectodermal origin is a member of the group consisting of glioma, meningioma, ependymoma, medulloblastoma, neuroblastoma, ganglioma, pheochromocytoma, melanoma, peripheral primitive neuroectodermal tumor, small cell carcinoma of the lung, and Ewing's sarcoma.

19. The method of claim 18, wherein the tumor of neuroectodermal origin is glioma.

20. The method of claim 1, wherein the step of administering comprises administering at least one dose of chlorotoxin agent, wherein the dose comprises between approximately 0.01 mg/kg and approximately 5 mg/kg.

21. The method of claim 1, further comprising a step of detecting at least one metastasis prior to administering the chlorotoxin agent to the individual.

22. The method of claim 1, wherein neovasculature of the at least one metastasis regresses.

23. The method of claim 1, wherein neovascularization is inhibited.

24. The method of claim 1, wherein migration of at least one cell in the primary tumor is inhibited.

25. The method of claim 1, wherein the chlorotoxin agent is covalently attached to a polymer.

26. The method of claim 25, wherein the polymer is polyethylene glycol (PEG).

27. The method of claim 1, further comprising a step of exposing the subject to a second pharmaceutical agent.

28. The method of claim 27, wherein the second pharmaceutical agent is a chemotherapeutic agent.

29. The method of claim 28, wherein the chemotherapeutic agent is selected from the group consisting of alkylating agents, purine antagonists, pyrimidine antagonists, plant alkaloids, intercalating antibiotics, aromatase inhibitors, anti-metabolites, mitotic inhibitors, growth factor inhibitor, cell cycle inhibitors, enzymes, topoisomerase inhibitors, biological response modifiers, anti-hormones and anti-androgens.

30. The method of claim 1, wherein the amino acid sequence of the chlorotoxin peptide is identical to that set forth in SEQ ID NO:1.

31. The method of claim 1, wherein the administering comprises a plurality of doses administered over a period of time.

32. The method of claim 31, wherein the doses are administered at 1 day intervals, 2 day intervals, 3 day intervals, 4 day intervals, 5 day intervals, 6 day intervals, 7 day intervals, 10 day intervals, 2 week intervals, or at intervals greater than 2 weeks, or wherein the doses are administered on an intermittent schedule.

33. The method of claim 31, wherein the plurality of doses comprises 2 doses, 3 doses, 4 doses, 5 doses, 6 doses, or more than 6 doses.

\* \* \* \* \*

SEQUENCE LISTING

<160> NUMBER OF SEQ ID NOS: 95

<210> SEQ ID NO 1
<211> LENGTH: 36
<212> TYPE: PRT
<213> ORGANISM: Leiurus quinquestriatus
<220> FEATURE:
<221> NAME/KEY: misc_feature
<223> OTHER INFORMATION: Chlorotoxin

<400> SEQUENCE: 1

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 2
<211> LENGTH: 42
<212> TYPE: PRT
<213> ORGANISM: Leiurus quinquestriatus

<400> SEQUENCE: 2

His His His His His His Met Cys Met Pro Cys Phe Thr Thr Asp His
1               5                   10                  15

Gln Met Ala Arg Lys Cys Asp Asp Cys Cys Gly Gly Lys Gly Arg Gly
            20                  25                  30

Lys Cys Tyr Gly Pro Gln Cys Leu Cys Arg
        35                  40

<210> SEQ ID NO 3
<211> LENGTH: 37
<212> TYPE: PRT
<213> ORGANISM: Leiurus quinquestriatus

<400> SEQUENCE: 3

Tyr Met Cys Met Pro Cys Phe Thr Thr Asp His Gln Met Ala Arg Lys
1               5                   10                  15

Cys Asp Asp Cys Cys Gly Gly Lys Gly Arg Gly Lys Cys Tyr Gly Pro
            20                  25                  30

Gln Cys Leu Cys Arg
        35

<210> SEQ ID NO 4
<211> LENGTH: 39
<212> TYPE: PRT
<213> ORGANISM: Leiurus quinquestriatus

<400> SEQUENCE: 4

Tyr Ser Tyr Met Cys Met Pro Cys Phe Thr Thr Asp His Gln Met Ala
1               5                   10                  15

Arg Lys Cys Asp Asp Cys Cys Gly Gly Lys Gly Arg Gly Lys Cys Tyr
            20                  25                  30

Gly Pro Gln Cys Leu Cys Arg
        35

<210> SEQ ID NO 5
<211> LENGTH: 36
<212> TYPE: PRT
<213> ORGANISM: Artificial sequence
<220> FEATURE:

```
<223> OTHER INFORMATION: Synthetic - chlorotoxin variant

<400> SEQUENCE: 5

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Phe Gly Pro Gln
            20                  25                  30

Cys Leu Cys Arg
        35

<210> SEQ ID NO 6
<211> LENGTH: 35
<212> TYPE: PRT
<213> ORGANISM: Artificial sequence
<220> FEATURE:
<223> OTHER INFORMATION: Synthetic - chlorotoxin variant

<400> SEQUENCE: 6

Arg Cys Lys Pro Cys Phe Thr Thr Asp Pro Gln Met Ser Lys Lys Cys
1               5                   10                  15

Ala Asp Cys Cys Gly Gly Lys Gly Lys Gly Lys Cys Tyr Gly Pro Gln
            20                  25                  30

Cys Leu Cys
        35

<210> SEQ ID NO 7
<211> LENGTH: 38
<212> TYPE: PRT
<213> ORGANISM: Artificial sequence
<220> FEATURE:
<223> OTHER INFORMATION: Synthetic - chlorotoxin variant

<400> SEQUENCE: 7

Arg Cys Ser Pro Cys Phe Thr Thr Asp Gln Gln Met Thr Lys Lys Cys
1               5                   10                  15

Tyr Asp

```
<210> SEQ ID NO 10
<211> LENGTH: 9
<212> TYPE: PRT
<213> ORGANISM: Artificial sequence
<220> FEATURE:
<223> OTHER INFORMATION: Synthetic - chlorotoxin alpha peptide

<400> SEQUENCE: 10

Thr Asp His Gln Met Ala Arg Lys Ser
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic - variant of chlorotoxin alpha
      peptide

<400> SEQUENCE: 11

Thr Ala His Ala Met Ala Arg Lys Ser
1               5

<210> SEQ ID NO 12
<211> LENGTH: 36
<212> TYPE: PRT
<213> ORGANISM: Artificial sequence
<220> FEATURE:
<223> OTHER INFORMATION: Synthetic - variant peptide of chlorotoxin

<400> SEQUENCE: 12

Met Cys Met Pro Cys Phe Thr Thr Ala His Ala Met Ala Arg Lys Cys
1               5                   10                  15

Asp Asp Cys Cys Gly Gly Lys Gly Arg Cys Lys Cys Tyr Gly Pro Gln
            20                  25                  30

Cys Leu Cys Arg
        35

<210> SEQ ID NO 13
<211> LENGTH: 9
<212> TYPE: PRT
<213> ORGANISM: Artificial
<220> FEATURE:
<223> OTHER INFORMATION: Synthetic - motif for chlorotoxin derivatives
<220> FEATURE:
<221> NAME/KEY: misc_feature
<222> LOCATION: (3)..(3)
<223> OTHER INFORMATION: Xaa can be Asp or Glu
<220> FEATURE:
<221> NAME/KEY: misc_feature
<222> LOCATION: (4)..(4)
<223> OTHER INFORMATION: Xaa can be Ala, Arg, Asn, Asp, Cys, Gln, Glu,
      Gly, His, Ile, Leu, Lys, Met, Phe, Pro, Ser, Thr, Trp, Tyr, or Val
<220> FEATURE:
<221> NAME/KEY: misc_feature
<222> LOCATION: (5)..(5)
<223> OTHER INFORMATION: Xaa can be Asn or Gln
<220> FEATURE:
<221> NAME/KEY: misc_feature
<222> LOCATION: (7)..(7)
<223> OTHER INFORMATION: Xaa can be Ala, Arg, Asn, Asp, Cys, Gln, Glu,
      Gly, His, Ile, Leu, Lys, Met, Phe, Pro, Ser, Thr, Trp, Tyr, or Val
<220> FEATURE:
<221> NAME/KEY: misc_feature
<222> LOCATION: (8)..(8)
<223> OTHER INFORMATION: Xaa can be Arg, His, or Lys

<400> SEQUENCE: 13
```

```
Thr Thr Xaa Xaa Xaa Met Xaa Xaa Lys
1               5

<210> SEQ ID NO 14
<211> LENGTH: 9
<212> TYPE: PRT
<213> ORGANISM: Leiurus quinquestriatus

<400> SEQUENCE: 14

Thr Thr Asp His Gln Met Ala Arg Lys
1               5

<210> SEQ ID NO 15
<211> LENGTH: 35
<212> TYPE: PRT
<213> ORGANISM: Mesobuthus tamulus

<400> SEQUENCE: 15

Arg Cys Lys Pro Cys Phe Thr Thr Asp Pro Gln Met Ser Lys Lys Cys
1               5                   10                  15

Ala Asp Cys Cys Gly Gly Lys Gly Lys Gly Lys Cys Tyr Gly Pro Gln
            20                  25                  30

Cys Leu Cys
        35

<210> SEQ ID NO 16
<211> LENGTH: 34
<212> TYPE: PRT
<213> ORGANISM: Artificial sequence
<220> FEATURE:
<223> OTHER INFORMATION: Small Toxin consensus sequence
<220> FEATURE:
<221> NAME/KEY: MISC_FEATURE
<222> LOCATION: (2)..(2)
<223> OTHER INFORMATION: Xaa can be Met or Lys
<220> FEATURE:
<221> NAME/KEY: MISC_FEATURE
<222> LOCATION: (9)..(9)
<223> OTHER INFORMATION: Xaa can be His or Pro
<220> FEATURE:
<221> NAME/KEY: MISC_FEATURE
<222> LOCATION: (16)..(16)
<223> OTHER INFORMATION: Xaa can be Asp or Ala

<400> SEQUENCE: 16

Cys Xaa Pro Cys Phe Thr Thr Asp Xaa Gln Met Ala Lys Lys Cys Xaa
1               5                   10                  15

Asp Cys Cys Gly Gly Lys Gly Lys Gly Lys Cys Tyr Gly Pro Gln Cys
            20                  25                  30

Leu Cys

<210> SEQ ID NO 17
<211> LENGTH: 38
<212> TYPE: PRT
<213> ORGANISM: Leiurus quinquestriatus

<400> SEQUENCE: 17

Arg Cys Ser Pro Cys Phe Thr Thr Asp Gln Gln Met Thr Lys Lys Cys
1               5                   10                  15

Tyr Asp Cys Cys Gly Gly Lys Gly Lys Gly Lys Cys Tyr Gly Pro Gln
            20                  25                  30

Cys Ile Cys Ala Pro Tyr
        35
```

```
<210> SEQ ID NO 18
<211> LENGTH: 34
<212> TYPE: PRT
<213> ORGANISM: Artificial sequence
<220> FEATURE:
<223> OTHER INFORMATION: Synthetic - Probable Toxin LQH 8/6 consensus
      sequence
<220> FEATURE:
<221> NAME/KEY: MISC_FEATURE
<222> LOCATION: (2)..(2)
<223> OTHER INFORMATION: Xaa can be Met or Ser
<220> FEATURE:
<221> NAME/KEY: MISC_FEATURE
<222> LOCATION: (9)..(9)
<223> OTHER INFORMATION: Xaa can be His or Gln
<220> FEATURE:
<221> NAME/KEY: MISC_FEATURE
<222> LOCATION: (12)..(12)
<223> OTHER INFORMATION: Xaa can be Ala or Thr
<220> FEATURE:
<221> NAME/KEY: MISC_FEATURE
<222> LOCATION: (16)..(16)
<223> OTHER INFORMATION: Xaa can be Asp or Tyr

<400> SEQUENCE: 18

Cys Xaa Pro Cys Phe Thr Thr Asp Xaa Gln Met Xaa Lys Lys Cys Xaa
1               5                   10                  15

Asp Cys Cys Gly Gly Lys Gly Lys Gly Lys Cys Tyr Gly Pro Gln Cys
            20                  25                  30

Ile Cys

<210> SEQ ID NO 19
<211> LENGTH: 61
<212> TYPE: PRT
<213> ORGANISM: Mesobuthus martensii
<220> FEATURE:
<221> NAME/KEY: MISC_FEATURE
<222> LOCATION: (1)..(61)
<223> OTHER INFORMATION: Xaa can be any amino acid

<400> SEQUENCE: 19

Met Lys Phe Leu Tyr Gly Ile Val Phe Ile Ala Leu Phe Leu Thr Val
1               5                   10                  15

Met Phe Ala Thr Gln Thr Asp Gly Cys Gly Pro Cys Phe Thr Thr Asp
            20                  25                  30

Ala Asn Met Ala Arg Lys Cys Arg Glu Cys Cys Gly Gly Ile Gly Xaa
            35                  40                  45

Xaa Lys Cys Phe Gly Pro Gln Cys Leu Cys Asn Arg Ile
    50                  55                  60

<210> SEQ ID NO 20
<211> LENGTH: 34
<212> TYPE: PRT
<213> ORGANISM: Artificial sequence
<220> FEATURE:
<223> OTHER INFORMATION: Synthetic - Chinese Scorpion consensus sequence
<220> FEATURE:
<221> NAME/KEY: MISC_FEATURE
<222> LOCATION: (2)..(2)
<223> OTHER INFORMATION: Xaa can be Met or Gly
<220> FEATURE:
<221> NAME/KEY: MISC_FEATURE
<222> LOCATION: (9)..(9)
<223> OTHER INFORMATION: Xaa can be His or Ala
<220> FEATURE:
<221> NAME/KEY: MISC_FEATURE
<222> LOCATION: (16)..(16)
<223> OTHER INFORMATION: Xaa can be Asp or Arg
<220> FEATURE:
```

```
<221> NAME/KEY: MISC_FEATURE
<222> LOCATION: (22)..(22)
<223> OTHER INFORMATION: Xaa can be Lys or Ile
<220> FEATURE:
<221> NAME/KEY: MISC_FEATURE
<222> LOCATION: (24)..(25)
<223> OTHER INFORMATION: Xaa can be any amino acid

<400> SEQUENCE: 20

Cys Xaa Pro Cys Phe Thr Thr Asp Xaa Asn Met Ala Arg Lys Cys Xaa
1               5                   10                  15

Asp Cys Cys Gly Gly Xaa Gly Xaa Xaa Lys Cys Phe Gly Pro Gln Cys
            20                  25                  30

Leu Cys

<210> SEQ ID NO 21
<211> LENGTH: 59
<212> TYPE: PRT
<213> ORGANISM: Mesobuthus martensii

<400> SEQUENCE: 21

Met Lys Phe Leu Tyr Gly Ile Val Phe Ile Ala Leu Phe Leu Thr Val
1               5                   10                  15

Met Phe Ala Thr Gln Thr Asp Gly Cys Gly Pro Cys Phe Thr Thr Asp
            20                  25                  30

Ala Asn Met Ala Arg Lys Cys Arg Glu Cys Cys Gly Gly Ile Gly Lys
        35                  40                  45

Cys Phe Gly Pro Gln Cys Leu Cys Asn Arg Ile
    50                  55

<210> SEQ ID NO 22
<211> LENGTH: 32
<212> TYPE: PRT
<213> ORGANISM: Artificial sequence
<220> FEATURE:
<223> OTHER INFORMATION: Chinese Scorpion consensus sequence
<220> FEATURE:
<221> NAME/KEY: MISC_FEATURE
<222> LOCATION: (2)..(2)
<223> OTHER INFORMATION: Xaa can be Met or Gly
<220> FEATURE:
<221> NAME/KEY: MISC_FEATURE
<222> LOCATION: (9)..(9)
<223> OTHER INFORMATION: Xaa can be His or Ala
<220> FEATURE:
<221> NAME/KEY: MISC_FEATURE
<222> LOCATION: (16)..(16)
<223> OTHER INFORMATION: Xaa can be Asp or Arg
<220> FEATURE:
<221> NAME/KEY: MISC_FEATURE
<222> LOCATION: (22)..(22)
<223> OTHER INFORMATION: Xaa can be Lys or Ile
<220> FEATURE:
<221> NAME/KEY: MISC_FEATURE
<222> LOCATION: (25)..(25)
<223> OTHER INFORMATION: Xaa can be Gly or Cys
<220> FEATURE:
<221> NAME/KEY: MISC_FEATURE
<222> LOCATION: (26)..(26)
<223> OTHER INFORMATION: Xaa can be Lys or Phe
<220> FEATURE:
<221> NAME/KEY: MISC_FEATURE
<222> LOCATION: (27)..(27)
<223> OTHER INFORMATION: Xaa can be Cys or Gly
<220> FEATURE:
<221> NAME/KEY: MISC_FEATURE
<222> LOCATION: (28)..(28)
<223> OTHER INFORMATION: Xaa can be Tyr or Pro
<220> FEATURE:
<221> NAME/KEY: MISC_FEATURE
```

-continued

```
<222> LOCATION: (29)..(29)
<223> OTHER INFORMATION: Xaa can be Gly or Gln
<220> FEATURE:
<221> NAME/KEY: MISC_FEATURE
<222> LOCATION: (30)..(30)
<223> OTHER INFORMATION: Xaa can be Pro or Cys
<220> FEATURE:
<221> NAME/KEY: MISC_FEATURE
<222> LOCATION: (31)..(31)
<223> OTHER INFORMATION: Xaa can be Gln or Leu

<400> SEQUENCE: 22

Cys Xaa Pro Cys Phe Thr Thr Asp Xaa Asn Met Ala Arg Lys Cys Xaa
1               5                   10                  15

Asp Cys Cys Gly Gly Xaa Gly Lys Xaa Xaa Xaa Xaa Xaa Xaa Cys
            20                  25                  30

<210> SEQ ID NO 23
<211> LENGTH: 37
<212> TYPE: PRT
<213> ORGANISM: Mesobuthus eupeus
<220> FEATURE:
<221> NAME/KEY: MISC_FEATURE
<222> LOCATION: (1)..(37)
<223> OTHER INFORMATION: Xaa can be any amino acid

<400> SEQUENCE: 23

Met Cys Met Pro Cys Phe Thr Thr Asp Pro Asn Met Ala Asn Lys Cys
1               5                   10                  15

Arg Asp Cys Cys Gly Gly Xaa Gly Lys Xaa Lys Cys Phe Gly Pro Gln
            20                  25                  30

Cys Leu Cys Asn Arg
        35

<210> SEQ ID NO 24
<211> LENGTH: 35
<212> TYPE: PRT
<213> ORGANISM: Artificial sequence
<220> FEATURE:
<223> OTHER INFORMATION: Synthetic - Insect toxin I5 consensus sequence
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (14)..(14)
<223> OTHER INFORMATION: Xaa can be Arg or Asn
<220> FEATURE:
<221> NAME/KEY: MISC_FEATURE
<222> LOCATION: (17)..(17)
<223> OTHER INFORMATION: Xaa can be Asp or Arg
<220> FEATURE:
<221> NAME/KEY: MISC_FEATURE
<222> LOCATION: (23)..(26)
<223> OTHER INFORMATION: Xaa can be any amino acid

<400> SEQUENCE: 24

Met Cys Met Pro Cys Phe Thr Thr Asp Xaa Asn Met Ala Xaa Lys Cys
1               5                   10                  15

Xaa Asp Cys Cys Gly Gly Xaa Gly Lys Xaa Lys Cys Phe Gly Pro Gln
            20                  25                  30

Cys Leu Cys
        35

<210> SEQ ID NO 25
<211> LENGTH: 35
<212> TYPE: PRT
```

<213> ORGANISM: Mesobuthus eupeus

<400> SEQUENCE: 25

Met Cys Met Pro Cys Phe Thr Thr Asp Pro Asn Met Ala Asn Lys Cys
1               5                   10                  15

Arg Asp Cys Cys Gly Gly Gly Lys Lys Cys Phe Gly Pro Gln Cys Leu
            20                  25                  30

Cys Asn Arg
        35

<210> SEQ ID NO 26
<211> LENGTH: 33
<212> TYPE: PRT
<213> ORGANISM: Artificial sequence
<220> FEATURE:
<223> OTHER INFORMATION: Synthetic - Insect toxin I5 consensus sequence
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (14)..(14)
<223> OTHER INFORMATION: Xaa can be Arg or Asn
<220> FEATURE:
<221> NAME/KEY: MISC_FEATURE
<222> LOCATION: (17)..(17)
<223> OTHER INFORMATION: Xaa can be Asp or Arg
<220> FEATURE:
<221> NAME/KEY: MISC_FEATURE
<222> LOCATION: (23)..(24)
<223> OTHER INFORMATION: Xaa can be Lys or Gly
<220> FEATURE:
<221> NAME/KEY: MISC_FEATURE
<222> LOCATION: (26)..(26)
<223> OTHER INFORMATION: Xaa can be Gly or Cys
<220> FEATURE:
<221> NAME/KEY: MISC_FEATURE
<222> LOCATION: (27)..(27)
<223> OTHER INFORMATION: Xaa can be Lys or Phe
<220> FEATURE:
<221> NAME/KEY: MISC_FEATURE
<222> LOCATION: (28)..(28)
<223> OTHER INFORMATION: Xaa can be Cys or Gly
<220> FEATURE:
<221> NAME/KEY: MISC_FEATURE
<222> LOCATION: (29)..(29)
<223> OTHER INFORMATION: Xaa can be Tyr or Pro
<220> FEATURE:
<221> NAME/KEY: MISC_FEATURE
<222> LOCATION: (30)..(30)
<223> OTHER INFORMATION: Xaa can be Gly or Gln
<220> FEATURE:
<221> NAME/KEY: MISC_FEATURE
<222> LOCATION: (31)..(31)
<223> OTHER INFORMATION: Xaa can be Pro or Cys
<220> FEATURE:
<221> NAME/KEY: MISC_FEATURE
<222> LOCATION: (32)..(32)
<223> OTHER INFORMATION: Xaa can be Gln or Leu

<400> SEQUENCE: 26

Met Cys Met Pro Cys Phe Thr Thr Asp Xaa Asn Met Ala Xaa Lys Cys
1               5                   10                  15

Xaa Asp Cys Cys Gly Gly Xaa Xaa Lys Xaa Xaa Xaa Xaa Xaa Xaa Xaa
            20                  25                  30

Cys

<210> SEQ ID NO 27
<211> LENGTH: 38
<212> TYPE: PRT

```
<213> ORGANISM: Mesobuthus eupeus
<220> FEATURE:
<221> NAME/KEY: MISC_FEATURE
<222> LOCATION: (1)..(38)
<223> OTHER INFORMATION: Xaa can be any amino acid

<400> SEQUENCE: 27

Met Cys Met Pro Cys Phe Thr Thr Arg Pro Asp Met Ala Gln Gln Cys
1               5                   10                  15

Arg Ala Cys Cys Lys Gly Xaa Xaa Arg Gly Lys Cys Phe Gly Pro Gln
            20                  25                  30

Cys Leu Cys Gly Tyr Asp
        35

<210> SEQ ID NO 28
<211> LENGTH: 35
<212> TYPE: PRT
<213> ORGANISM: Artificial sequence
<220> FEATURE:
<223> OTHER INFORMATION: Synthetic - Insectotoxin I1 consensus sequence
<220> FEATURE:
<221> NAME/KEY: MISC_FEATURE
<222> LOCATION: (9)..(9)
<223> OTHER INFORMATION: Xaa can be Asp or Arg
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (11)..(11)
<223> OTHER INFORMATION: Xaa can be Gln or Asp
<220> FEATURE:
<221> NAME/KEY: MISC_FEATURE
<222> LOCATION: (14)..(14)
<223> OTHER INFORMATION: Xaa can be Arg or Gln
<220> FEATURE:
<221> NAME/KEY: MISC_FEATURE
<222> LOCATION: (15)..(15)
<223> OTHER INFORMATION: Xaa can be Lys or Gln
<220> FEATURE:
<221> NAME/KEY: MISC_FEATURE
<222> LOCATION: (17)..(17)
<223> OTHER INFORMATION: Xaa can be Asp or Arg
<220> FEATURE:
<221> NAME/KEY: MISC_FEATURE
<222> LOCATION: (18)..(18)
<223> OTHER INFORMATION: Xaa can be Asp or Ala
<220> FEATURE:
<221> NAME/KEY: MISC_FEATURE
<222> LOCATION: (21)..(21)
<223> OTHER INFORMATION: Xaa can be Gly or Lys
<220> FEATURE:
<221> NAME/KEY: MISC_FEATURE
<222> LOCATION: (23)..(24)
<223> OTHER INFORMATION: Xaa can be any amino acid

<400> SEQUENCE: 28

Met Cys Met Pro Cys Phe Thr Thr Xaa Xaa Xaa Met Ala Xaa Xaa Cys
1               5                   10                  15

Xaa Xaa Cys Cys Xaa Gly Xaa Xaa Arg Gly Lys Cys Phe Gly Pro Gln
            20                  25                  30

Cys Leu Cys
        35

<210> SEQ ID NO 29
<211> LENGTH: 36
<212> TYPE: PRT
<213> ORGANISM: Mesobuthus eupeus

<400> SEQUENCE: 29
```

```
Met Cys Met Pro Cys Phe Thr Thr Arg Pro Asp Met Ala Gln Gln Cys
1               5                   10                  15

Arg Ala Cys Cys Lys Gly Arg Gly Lys Cys Phe Gly Pro Gln Cys Leu
            20                  25                  30

Cys Gly Tyr Asp
        35

<210> SEQ ID NO 30
<211> LENGTH: 33
<212> TYPE: PRT
<213> ORGANISM: Artificial sequence
<220> FEATURE:
<223> OTHER INFORMATION: Synthetic - Insectotoxin I1 consensus sequence
<220> FEATURE:
<221> NAME/KEY: MISC_FEATURE
<222> LOCATION: (9)..(9)
<223> OTHER INFORMATION: Xaa can be Asp or Arg
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (11)..(11)
<223> OTHER INFORMATION: Xaa can be Gln or Asp
<220> FEATURE:
<221> NAME/KEY: MISC_FEATURE
<222> LOCATION: (14)..(14)
<223> OTHER INFORMATION: Xaa can be Arg or Gln
<220> FEATURE:
<221> NAME/KEY: MISC_FEATURE
<222> LOCATION: (15)..(15)
<223> OTHER INFORMATION: Xaa can be Lys or Gln
<220> FEATURE:
<221> NAME/KEY: MISC_FEATURE
<222> LOCATION: (17)..(17)
<223> OTHER INFORMATION: Xaa can be Asp or Arg
<220> FEATURE:
<221> NAME/KEY: MISC_FEATURE
<222> LOCATION: (18)..(18)
<223> OTHER INFORMATION: Xaa can be Asp or Arg
<220> FEATURE:
<221> NAME/KEY: MISC_FEATURE
<222> LOCATION: (21)..(21)
<223> OTHER INFORMATION: Xaa can be Gly or Lys
<220> FEATURE:
<221> NAME/KEY: MISC_FEATURE
<222> LOCATION: (26)..(26)
<223> OTHER INFORMATION: Xaa can be Gly or Cys
<220> FEATURE:
<221> NAME/KEY: MISC_FEATURE
<222> LOCATION: (27)..(27)
<223> OTHER INFORMATION: Xaa can be Lys or Phe
<220> FEATURE:
<221> NAME/KEY: MISC_FEATURE
<222> LOCATION: (28)..(28)
<223> OTHER INFORMATION: Xaa can be Cys or Gly
<220> FEATURE:
<221> NAME/KEY: MISC_FEATURE
<222> LOCATION: (29)..(29)
<223> OTHER INFORMATION: Xaa can be Tyr or Pro
<220> FEATURE:
<221> NAME/KEY: MISC_FEATURE
<222> LOCATION: (30)..(30)
<223> OTHER INFORMATION: Xaa can be Gly or Gln
<220> FEATURE:
<221> NAME/KEY: MISC_FEATURE
<222> LOCATION: (31)..(31)
<223> OTHER INFORMATION: Xaa can be Pro or Cys
<220> FEATURE:
<221> NAME/KEY: MISC_FEATURE
<222> LOCATION: (32)..(32)
<223> OTHER INFORMATION: Xaa can be Gln or Leu

<400> SEQUENCE: 30
```

```
Met Cys Met Pro Cys Phe Thr Thr Xaa Xaa Xaa Met Ala Xaa Xaa Cys
1               5                   10                  15

Xaa Xaa Cys Cys Xaa Gly Lys Gly Lys Xaa Xaa Xaa Xaa Xaa Xaa
            20                  25                  30

Cys

<210> SEQ ID NO 31
<211> LENGTH: 37
<212> TYPE: PRT
<213> ORGANISM: Mesobuthus eupeus
<220> FEATURE:
<221> NAME/KEY: MISC_FEATURE
<222> LOCATION: (1)..(37)
<223> OTHER INFORMATION: Xaa can be any amino acid

<400> SEQUENCE: 31

Met Cys Met Pro Cys Phe Thr Thr Asp Pro Asn Met Ala Lys Lys Cys
1               5                   10                  15

Arg Asp Cys Cys Gly Gly Asn Gly Xaa Xaa Lys Cys Phe Gly Pro Gln
            20                  25                  30

Cys Leu Cys Asn Arg
        35

<210> SEQ ID NO 32
<211> LENGTH: 35
<212> TYPE: PRT
<213> ORGANISM: Artificial sequence
<220> FEATURE:
<223> OTHER INFORMATION: Synthetic - Insectotoxin 15A consensus sequence
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (17)..(17)
<223> OTHER INFORMATION: Xaa can be Asp or Arg
<220> FEATURE:
<221> NAME/KEY: MISC_FEATURE
<222> LOCATION: (23)..(23)
<223> OTHER INFORMATION: Xaa can be Lys or Asn
<220> FEATURE:
<221> NAME/KEY: MISC_FEATURE
<222> LOCATION: (25)..(26)
<223> OTHER INFORMATION: Xaa can be any amino acid

<400> SEQUENCE: 32

Met Cys Met Pro Cys Phe Thr Thr Asp Xaa Asn Met Ala Lys Lys Cys
1               5                   10                  15

Xaa Asp Cys Cys Gly Gly Xaa Gly Xaa Xaa Lys Cys Phe Gly Pro Gln
            20                  25                  30

Cys Leu Cys
        35

<210> SEQ ID NO 33
<211> LENGTH: 35
<212> TYPE: PRT
<213> ORGANISM: Mesobuthus eupeus

<400> SEQUENCE: 33

Met Cys Met Pro Cys Phe Thr Thr Asp Pro Asn Met Ala Lys Lys Cys
1               5                   10                  15

Arg Asp Cys Cys Gly Gly Asn Gly Lys Cys Phe Gly Pro Gln Cys Leu
            20                  25                  30
```

Cys Asn Arg
        35

<210> SEQ ID NO 34
<211> LENGTH: 33
<212> TYPE: PRT
<213> ORGANISM: Artificial sequence
<220> FEATURE:
<223> OTHER INFORMATION: Synthetic - Insectotoxin 15A consensus sequence
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (17)..(17)
<223> OTHER INFORMATION: Xaa can be Asp or Arg
<220> FEATURE:
<221> NAME/KEY: MISC_FEATURE
<222> LOCATION: (23)..(23)
<223> OTHER INFORMATION: Xaa can be Lys or Asn
<220> FEATURE:
<221> NAME/KEY: MISC_FEATURE
<222> LOCATION: (26)..(26)
<223> OTHER INFORMATION: Xaa can be Gly or Cys
<220> FEATURE:
<221> NAME/KEY: MISC_FEATURE
<222> LOCATION: (27)..(27)
<223> OTHER INFORMATION: Xaa can be Lys or Phe
<220> FEATURE:
<221> NAME/KEY: MISC_FEATURE
<222> LOCATION: (28)..(28)
<223> OTHER INFORMATION: Xaa can be Cys or Gly
<220> FEATURE:
<221> NAME/KEY: MISC_FEATURE
<222> LOCATION: (29)..(29)
<223> OTHER INFORMATION: Xaa can be Tyr or Pro
<220> FEATURE:
<221> NAME/KEY: MISC_FEATURE
<222> LOCATION: (30)..(30)
<223> OTHER INFORMATION: Xaa can be Gly or Gln
<220> FEATURE:
<221> NAME/KEY: MISC_FEATURE
<222> LOCATION: (31)..(31)
<223> OTHER INFORMATION: Xaa can be Pro or Cys
<220> FEATURE:
<221> NAME/KEY: MISC_FEATURE
<222> LOCATION: (32)..(32)
<223> OTHER INFORMATION: Xaa can be Gln or Leu

<400> SEQUENCE: 34

Met Cys Met Pro Cys Phe Thr Thr Asp Xaa Asn Met Ala Lys Lys Cys
1               5                   10                  15

Xaa Asp Cys Cys Gly Gly Xaa Gly Lys Xaa Xaa Xaa Xaa Xaa Xaa Xaa
            20                  25                  30

Cys

<210> SEQ ID NO 35
<211> LENGTH: 37
<212> TYPE: PRT
<213> ORGANISM: Androctonus mauretanicus
<220> FEATURE:
<221> NAME/KEY: MISC_FEATURE
<222> LOCATION: (1)..(37)
<223> OTHER INFORMATION: Xaa can be any amino acid

<400> SEQUENCE: 35

Cys Gly Pro Cys Phe Thr Thr Asp Pro Tyr Thr Glu Ser Lys Cys Ala
1               5                   10                  15

Thr Cys Cys Gly Gly Xaa Xaa Arg Gly Lys Cys Val Gly Pro Gln Cys
            20                  25                  30

Leu Cys Asn Arg Ile
        35

<210> SEQ ID NO 36
<211> LENGTH: 34
<212> TYPE: PRT
<213> ORGANISM: Artificial sequence
<220> FEATURE:
<223> OTHER INFORMATION: Neurotoxin P2 consensus sequence
<220> FEATURE:
<221> NAME/KEY: MISC_FEATURE
<222> LOCATION: (2)..(2)
<223> OTHER INFORMATION: Xaa can be Met or Gly
<220> FEATURE:
<221> NAME/KEY: MISC_FEATURE
<222> LOCATION: (9)..(9)
<223> OTHER INFORMATION: Xaa can be His or Pro
<220> FEATURE:
<221> NAME/KEY: MISC_FEATURE
<222> LOCATION: (10)..(10)
<223> OTHER INFORMATION: Xaa can be Gln or Tyr
<220> FEATURE:
<221> NAME/KEY: MISC_FEATURE
<222> LOCATION: (11)..(11)
<223> OTHER INFORMATION: Xaa can be Met or Thr
<220> FEATURE:
<221> NAME/KEY: MISC_FEATURE
<222> LOCATION: (12)..(12)
<223> OTHER INFORMATION: Xaa can be Ala or Glu
<220> FEATURE:
<221> NAME/KEY: MISC_FEATURE
<222> LOCATION: (13)..(13)
<223> OTHER INFORMATION: Xaa can be Arg or Ser
<220> FEATURE:
<221> NAME/KEY: MISC_FEATURE
<222> LOCATION: (16)..(16)
<223> OTHER INFORMATION: Xaa can be Asp or Ala
<220> FEATURE:
<221> NAME/KEY: MISC_FEATURE
<222> LOCATION: (17)..(17)
<223> OTH

```
<210> SEQ ID NO 38
<211> LENGTH: 32
<212> TYPE: PRT
<213> ORGANISM: Artificial sequence
<220> FEATURE:
<223> OTHER INFORMATION: Synthetic - Neurotoxin P2 consensus sequence
<220> FEATURE:
<221> NAME/KEY: MISC_FEATURE
<222> LOCATION: (2)..(2)
<223> OTHER INFORMATION: Xaa can be Met or Gly
<220> FEATURE:
<221> NAME/KEY: MISC_FEATURE
<222> LOCATION: (9)..(9)
<223> OTHER INFORMATION: Xaa can be His or Pro
<220> FEATURE:
<221> NAME/KEY: MISC_FEATURE
<222> LOCATION: (10)..(10)
<223> OTHER INFORMATION: Xaa can be Gln or Tyr
<220> FEATURE:
<221> NAME/KEY: MISC_FEATURE
<222> LOCATION: (11)..(11)
<223> OTHER INFORMATION: Xaa ca be Met or Thr
<220> FEATURE:
<221> NAME/KEY: MISC_FEATURE
<222> LOCATION: (12)..(12)
<223> OTHER INFORMATION: Xaa can be Ala or Glu
<220> FEATURE:
<221> NAME/KEY: MISC_FEATURE
<222> LOCATION: (13)..(13)
<223> OTHER INFORMATION: Xaa can be Arg or Ser
<220> FEATURE:
<221> NAME/KEY: MISC_FEATURE
<222> LOCATION: (16)..(16)
<223> OTHER INFORMATION: Xaa can be Asp or Ala
<220> FEATURE:
<221> NAME/KEY: MISC_FEATURE
<222> LOCATION: (17)..(17)
<223> OTHER INFORMATION: Xaa can be Asp or Thr
<220> FEATURE:
<221> NAME/KEY: MISC_FEATURE
<222> LOCATION: (25)..(25)
<223> OTHER INFORMATION: Xaa can be Gly or Cys
<220> FEATURE:
<221> NAME/KEY: MISC_FEATURE
<222> LOCATION: (26)..(26)
<223> OTHER INFORMATION: Xaa can be Lys or Val
<220> FEATURE:
<221> NAME/KEY: MISC_FEATURE
<222> LOCATION: (27)..(27)
<223> OTHER INFORMATION: Xaa can be Cys or Gly
<220> FEATURE:
<221> NAME/KEY: MISC_FEATURE
<222> LOCATION: (28)..(28)
<223> OTHER INFORMATION: Xaa can be Tyr or Pro
<220> FEATURE:
<221> NAME/KEY: MISC_FEATURE
<222> LOCATION: (29)..(29)
<223> OTHER INFORMATION: Xaa can be Gly or Gln
<220> FEATURE:
<221> NAME/KEY: MISC_FEATURE
<222> LOCATION: (30)..(30)
<223> OTHER INFORMATION: Xaa can be Pro or Cys
<220> FEATURE:
<221> NAME/KEY: MISC_FEATURE
<222> LOCATION: (31)..(31)
<223> OTHER INFORMATION: Xaa can be Gln or Leu

<400> SEQUENCE: 38

Cys Xaa Pro Cys Phe Thr Thr Asp Xaa Xaa Xaa Xaa Xaa Lys Cys Xaa
 1               5                  10                  15

Xaa Cys Cys Gly Gly Lys Gly Lys Xaa Xaa Xaa Xaa Xaa Xaa Xaa Cys
                20                  25                  30

<210> SEQ ID NO 39
<211> LENGTH: 37
<212> TYPE: PRT
```

```
<213> ORGANISM: Artificial sequence
<220> FEATURE:
<223> OTHER INFORMATION: Synthetic - Toxin consensus sequence
<220> FEATURE:
<221> NAME/KEY: MISC_FEATURE
<222> LOCATION: (1)..(37)
<223> OTHER INFORMATION: Xaa can be any amino acid

<400> SEQUENCE: 39

Met Cys Met Pro Cys Phe Thr Thr Asp Pro Asn Met Ala Lys Lys Cys
1               5                   10                  15

Arg Asp Cys Cys Gly Gly Lys Gly Xaa Xaa Lys Cys Phe Gly Pro Gln
            20                  25                  30

Cys Leu Cys Asn Arg
        35

<210> SEQ ID NO 40
<211> LENGTH: 35
<212> TYPE: PRT
<213> ORGANISM: Artificial sequence
<220> FEATURE:
<223> OTHER INFORMATION: Synthetic - Toxin consensus sequence
<220> FEATURE:
<221> NAME/KEY: MISC_FEATURE
<222> LOCATION: (3)..(3)
<223> OTHER INFORMATION: Xaa can be Met, Lys or Ser
<220> FEATURE:
<221> NAME/KEY: MISC_FEATURE
<222> LOCATION: (10)..(10)
<223> OTHER INFORMATION: Xaa can be His, Pro, or Gln
<220> FEATURE:
<221> NAME/KEY: MISC_FEATURE
<222> LOCATION: (17)..(17)
<223> OTHER INFORMATION: Xaa can be Asp, Ala, or Tyr

<400> SEQUENCE: 40

Arg Cys Xaa Pro Cys Phe Thr Thr Asp Xaa Gln Met Ser Lys Lys Cys
1               5                   10                  15

Xaa Asp Cys Cys Gly Gly Lys Gly Lys Gly Lys Cys Tyr Gly Pro Gln
            20                  25                  30

Cys Leu Cys
        35

<210> SEQ ID NO 41
<211> LENGTH: 35
<212> TYPE: PRT
<213> ORGANISM: Artificial sequence
<220> FEATURE:
<223> OTHER INFORMATION: Synthetic -Toxin consensus sequence

<400> SEQUENCE: 41

Met Cys Met Pro Cys Phe Thr Thr Asp Pro Asn Met Ala Arg Lys Cys
1               5                   10                  15

Arg Asp Cys Cys Gly Gly Arg Gly Lys Cys Phe Gly Pro Gln Cys Leu
            20                  25                  30

Cys Asn Arg
        35

<210> SEQ ID NO 42
<211> LENGTH: 10
<212> TYPE: PRT
<213> ORGANISM: Artificial sequence
<220> FEATURE:
<223> OTHER INFORMATION: Synthetic - Pep8-Ctlx

<400> SEQUENCE: 42
```

Cys Gly Gly Lys Gly Arg Gly Lys Cys Tyr
1               5                   10

<210> SEQ ID NO 43
<211> LENGTH: 10
<212> TYPE: PRT
<213> ORGANISM: Artificial sequence
<220> FEATURE:
<223> OTHER INFORMATION: Synthetic - Pep8-SCX1_BUTSI

<400> SEQUENCE: 43

Cys Gly Gly Lys Gly Lys Gly Lys Cys Tyr
1               5                   10

<210> SEQ ID NO 44
<211> LENGTH: 10
<212> TYPE: PRT
<213> ORGANISM: Artificial sequence
<220> FEATURE:
<223> OTHER INFORMATION: Synthetic - Pep8-AF079059_2

<400> SEQUENCE: 44

Cys Gly Gly Ile Gly Lys Cys Phe Gly Pro
1               5                   10

<210> SEQ ID NO 45
<211> LENGTH: 12
<212> TYPE: PRT
<213> ORGANISM: Artificial sequence
<220> FEATURE:
<223> OTHER INFORMATION: Synthetic - Chlorotoxin Peptide 8 consensus
      sequence
<220> FEATURE:
<221> NAME/KEY: MISC_FEATURE
<222> LOCATION: (4)..(4)
<223> OTHER INFORMATION: Xaa can be Lys or Ile

<400> SEQUENCE: 45

Cys Gly Gly Xaa Gly Arg Gly Lys Cys Phe Gly Pro
1               5                   10

<210> SEQ ID NO 46
<211> LENGTH: 6
<212> TYPE: PRT
<213> ORGANISM: Artificial sequence
<220> FEATURE:
<223> OTHER INFORMATION: Synthetic - Chlorotoxin Peptide 8 consensus
      sequence
<220> FEATURE:
<221> NAME/KEY: MISC_FEATURE
<222> LOCATION: (4)..(4)
<223> OTHER INFORMATION: Xaa can be Lys or Ile

<400> SEQUENCE: 46

Cys Gly Gly Xaa Gly Lys
1               5

<210> SEQ ID NO 47
<211> LENGTH: 10
<212> TYPE: PRT
<213> ORGANISM: Artificial sequence
<220> FEATURE:
<223> OTHER INFORMATION: Synthetic - Pep8-NJ0361 sequence

<400> SEQUENCE: 47

Cys Gly Gly Gly Lys Lys Cys Phe Gly Pro
1               5                   10

```
<210> SEQ ID NO 48
<211> LENGTH: 12
<212> TYPE: PRT
<213> ORGANISM: Artificial sequence
<220> FEATURE:
<223> OTHER INFORMATION: Synthetic - Chlorotoxin Peptide 8 consensus
      sequence

<400> SEQUENCE: 48

Cys Gly Gly Lys Gly Lys Gly Lys Cys Phe Gly Pro
1               5                   10

<210> SEQ ID NO 49
<211> LENGTH: 6
<212> TYPE: PRT
<213> ORGANISM: Artificial sequence
<220> FEATURE:
<223> OTHER INFORMATION: Synthetic - Chlorotoxin Peptide 8 consensus
      sequence
<220> FEATURE:
<221> NAME/KEY: MISC_FEATURE
<222> LOCATION: (4)..(5)
<223> OTHER INFORMATION: Xaa can be Lys or Gly

<400> SEQUENCE: 49

Cys Gly Gly Xaa Xaa Lys
1               5

<210> SEQ ID NO 50
<211> LENGTH: 10
<212> TYPE: PRT
<213> ORGANISM: Artificial sequence
<220> FEATURE:
<223> OTHER INFORMATION: Synthetic - Pep8-SCX1_BUTEU sequence

<400> SEQUENCE: 50

Cys Lys Gly Arg Gly Lys Cys Phe Gly Pro
1               5                   10

<210> SEQ ID NO 51
<211> LENGTH: 12
<212> TYPE: PRT
<213> ORGANISM: Artificial sequence
<220> FEATURE:
<223> OTHER INFORMATION: Synthetic - chlorotoxin peptide 8 consensus
      sequence
<220> FEATURE:
<221> NAME/KEY: MISC_FEATURE
<222> LOCATION: (3)..(3)
<223> OTHER INFORMATION: Xaa can be Gly or Cys

<400> SEQUENCE: 51

Cys Gly Xaa Lys Gly Arg Gly Lys Cys Phe Gly Pro
1               5                   10

<210> SEQ ID NO 52
<211> LENGTH: 6
<212> TYPE: PRT
<213> ORGANISM: Artificial sequence
<220> FEATURE:
<223> OTHER INFORMATION: Synthetic - chlorotoxin peptide 8 consensus
      sequence
<220> FEATURE:
<221> NAME/KEY: MISC_FEATURE
<222> LOCATION: (2)..(2)
<223> OTHER INFORMATION: Xaa can be Gly or Lys

<400> SEQUENCE: 52

Cys Xaa Gly Lys Gly Lys
1               5
```

<210> SEQ ID NO 53
<211> LENGTH: 10
<212> TYPE: PRT
<213> ORGANISM: Artificial sequence
<220> FEATURE:
<223> OTHER INFORMATION: Synthetic - Pep8-SCX5_BUTEU sequence

<400> SEQUENCE: 53

Cys Gly Gly Asn Gly Lys Cys Phe Gly Pro
1               5                   10

<210> SEQ ID NO 54
<211> LENGTH: 12
<212> TYPE: PRT
<213> ORGANISM: Artificial sequence
<220> FEATURE:
<223> OTHER INFORMATION: Synthetic - chlorotoxin peptide 8 consensus
      sequence
<220> FEATURE:
<221> NAME/KEY: MISC_FEATURE
<222> LOCATION: (4)..(4)
<223> OTHER INFORMATION: Xaa can be Lys or Asn

<400> SEQUENCE: 54

Cys Gly Gly Xaa Gly Arg Gly Lys Cys Phe Gly Pro
1               5                   10

<210> SEQ ID NO 55
<211> LENGTH: 6
<212> TYPE: PRT
<213> ORGANISM: Artificial sequence
<220> FEATURE:
<223> OTHER INFORMATION: Synthetic - chlorotoxin peptide 8 consensus
      sequence
<220> FEATURE:
<221> NAME/KEY: MISC_FEATURE
<222> LOCATION: (4)..(4)
<223> OTHER INFORMATION: Xaa can be Lys or Asn

<400> SEQUENCE: 55

Cys Gly Gly Xaa Gly Lys
1               5

<210> SEQ ID NO 56
<211> LENGTH: 10
<212> TYPE: PRT
<213> ORGANISM: Artificial sequence
<220> FEATURE:
<223> OTHER INFORMATION: Synthetic - Pep8-SCXP_ANDMA sequence

<400> SEQUENCE: 56

Cys Gly Gly Arg Gly Lys Cys Val Gly Pro
1               5                   10

<210> SEQ ID NO 57
<211> LENGTH: 12
<212> TYPE: PRT
<213> ORGANISM: Artificial sequence
<220> FEATURE:
<223> OTHER INFORMATION: Synthetic - chlorotoxin peptide 8 consensus
      sequence
<220> FEATURE:
<221> NAME/KEY: MISC_FEATURE
<222> LOCATION: (10)..(10)
<223> OTHER INFORMATION: Xaa can be Tyr or Val

<400> SEQUENCE: 57

Cys Gly Gly Lys Gly Arg Gly Lys Cys Xaa Gly Pro

```
1               5              10
```

<210> SEQ ID NO 58
<211> LENGTH: 6
<212> TYPE: PRT
<213> ORGANISM: Artificial sequence
<220> FEATURE:
<223> OTHER INFORMATION: Synthetic - chlorotoxin peptide 8 consensus
      sequence

<400> SEQUENCE: 58

```
Cys Gly Gly Lys Gly Lys
1               5
```

<210> SEQ ID NO 59
<211> LENGTH: 12
<212> TYPE: PRT
<213> ORGANISM: Artificial sequence
<220> FEATURE:
<223> OTHER INFORMATION: Synthetic - chlorotoxin peptide 8 consensus
      sequence
<220> FEATURE:
<221> NAME/KEY: MISC_FEATURE
<222> LOCATION: (4)..(5)
<223> OTHER INFORMATION: Xaa can be Lys or Gly

<400> SEQUENCE: 59

```
Cys Gly Gly Xaa Xaa Arg Gly Lys Cys Phe Gly Pro
1               5                   10
```

<210> SEQ ID NO 60
<211> LENGTH: 10
<212> TYPE: PRT
<213> ORGANISM: Artificial sequence
<220> FEATURE:
<223> OTHER INFORMATION: Synthetic - chlorotoxin peptide 8 consensus
      sequence

<400> SEQUENCE: 60

```
Cys Gly Gly Lys Gly Lys Cys Phe Gly Pro
1               5                   10
```

<210> SEQ ID NO 61
<211> LENGTH: 10
<212> TYPE: PRT
<213> ORGANISM: Artificial sequence
<220> FEATURE:
<223> OTHER INFORMATION: Synthetic - chlorotoxin peptide 21 sequence

<400> SEQUENCE: 61

```
Thr Thr Asp His Gln Met Ala Arg Lys Cys
1               5                   10
```

<210> SEQ ID NO 62
<211> LENGTH: 10
<212> TYPE: PRT
<213> ORGANISM: Artificial sequence
<220> FEATURE:
<223> OTHER INFORMATION: Synthetic - Pep21-SCX1-BUTSI sequence

<400> SEQUENCE: 62

```
Thr Thr Asp Pro Gln Met Ser Lys Lys Cys
1               5                   10
```

<210> SEQ ID NO 63
<211> LENGTH: 10
<212> TYPE: PRT
<213> ORGANISM: Artificial sequence

```
<220> FEATURE:
<223> OTHER INFORMATION: Synthetic - chlorotoxin peptide 21 consensus
      sequence
<220> FEATURE:
<221> NAME/KEY: MISC_FEATURE
<222> LOCATION: (4)..(4)
<223> OTHER INFORMATION: Xaa can be His or Pro

<400> SEQUENCE: 63

Thr Thr Asp Xaa Gln Met Ala Lys Lys Cys
1               5                   10

<210> SEQ ID NO 64
<211> LENGTH: 10
<212> TYPE: PRT
<213> ORGANISM: Artificial sequence
<220> FEATURE:
<223> OTHER INFORMATION: Synthetic - Pep21-SCX8_LEIQH sequence

<400> SEQUENCE: 64

Thr Thr Asp Gln Gln Met Thr Lys Lys Cys
1               5                   10

<210> SEQ ID NO 65
<211> LENGTH: 10
<212> TYPE: PRT
<213> ORGANISM: Artificial sequence
<220> FEATURE:
<223> OTHER INFORMATION: Synthetic - chlorotoxin peptide 21 consensus
      sequence
<220> FEATURE:
<221> NAME/KEY: MISC_FEATURE
<222> LOCATION: (4)..(4)
<223> OTHER INFORMATION: Xaa can be His or Gln
<220> FEATURE:
<221> NAME/KEY: MISC_FEATURE
<222> LOCATION: (7)..(7)
<223> OTHER INFORMATION: Xaa can be Ala or Thr

<400> SEQUENCE: 65

Thr Thr Asp Xaa Gln Met Xaa Lys Lys Cys
1               5                   10

<210> SEQ ID NO 66
<211> LENGTH: 10
<212> TYPE: PRT
<213> ORGANISM: Artificial sequence
<220> FEATURE:
<223> OTHER INFORMATION: Synthetic - Pep21-AF079059_2 sequence

<400> SEQUENCE: 66

Thr Thr Asp Ala Asn Met Ala Arg Lys Cys
1               5                   10

<210> SEQ ID NO 67
<211> LENGTH: 10
<212> TYPE: PRT
<213> ORGANISM: Artificial sequence
<220> FEATURE:
<223> OTHER INFORMATION: Synthetic - chlorotoxin peptide 21 consensus
      sequence
<220> FEATURE:
<221> NAME/KEY: MISC_FEATURE
<222> LOCATION: (4)..(4)
<223> OTHER INFORMATION: Xaa can be His or Ala

<400> SEQUENCE: 67

Thr Thr Asp Xaa Asn Met Ala Arg Lys Cys
1               5                   10
```

<210> SEQ ID NO 68
<211> LENGTH: 10
<212> TYPE: PRT
<213> ORGANISM: Artificial sequence
<220> FEATURE:
<223> OTHER INFORMATION: Synthetic - Pep21-JN0361 sequence

<400> SEQUENCE: 68

Thr Thr Asp Pro Asn Met Ala Asn Lys Cys
1               5                   10

<210> SEQ ID NO 69
<211> LENGTH: 10
<212> TYPE: PRT
<213> ORGANISM: Artificial sequence
<220> FEATURE:
<223> OTHER INFORMATION: Synthetic - chlorotoxin peptide 21 consensus
      sequence
<220> FEATURE:
<221> NAME/KEY: MISC_FEATURE
<222> LOCATION: (4)..(4)
<223> OTHER INFORMATION: Xaa can be either His or Pro
<220> FEATURE:
<221> NAME/KEY: MISC_FEATURE
<222> LOCATION: (8)..(8)
<223> OTHER INFORMATION: Xaa can be Arg or Asn

<400> SEQUENCE: 69

Thr Thr Asp Xaa Asn Met Ala Xaa Lys Cys
1               5                   10

<210> SEQ ID NO 70
<211> LENGTH: 10
<212> TYPE: PRT
<213> ORGANISM: Artificial sequence
<220> FEATURE:
<223> OTHER INFORMATION: Synthetic - Pep21-SCX1_BUTEU sequence

<400> SEQUENCE: 70

Thr Thr Arg Pro Asp Met Ala Gln Gln Cys
1               5                   10

<210> SEQ ID NO 71
<211> LENGTH: 10
<212> TYPE: PRT
<213> ORGANISM: Artificial sequence
<220> FEATURE:
<223> OTHER INFORMATION: Synthetic - chlorotoxin peptide 21 consensus
      sequence
<220> FEATURE:
<221> NAME/KEY: MISC_FEATURE
<222> LOCATION: (3)..(3)
<223> OTHER INFORMATION: Xaa can be Asp or Arg
<220> FEATURE:
<221> NAME/KEY: MISC_FEATURE
<222> LOCATION: (4)..(4)
<223> OTHER INFORMATION: Xaa can be His or Pro
<220> FEATURE:
<221> NAME/KEY: MISC_FEATURE
<222> LOCATION: (5)..(5)
<223> OTHER INFORMATION: Xaa can be Gln or Asp
<220> FEATURE:
<221> NAME/KEY: MISC_FEATURE
<222> LOCATION: (8)..(8)
<223> OTHER INFORMATION: Xaa can be Arg or Gln
<220> FEATURE:
<221> NAME/KEY: MISC_FEATURE
<222> LOCATION: (9)..(9)
<223> OTHER INFORMATION: Xaa can be Lys or Gln

<400> SEQUENCE: 71

```
Thr Thr Xaa Xaa Xaa Met Ala Xaa Xaa Cys
1               5                   10
```

<210> SEQ ID NO 72
<211> LENGTH: 10
<212> TYPE: PRT
<213> ORGANISM: Artificial sequence
<220> FEATURE:
<223> OTHER INFORMATION: Synthetic - Pep21-SCX5_BUTEU sequence

<400> SEQUENCE: 72

```
Thr Thr Asp Pro Asn Met Ala Lys Lys Cys
1               5                   10
```

<210> SEQ ID NO 73
<211> LENGTH: 10
<212> TYPE: PRT
<213> ORGANISM: Artificial sequence
<220> FEATURE:
<223> OTHER INFORMATION: Synthetic - chlorotoxin peptide 21 consensus
      sequence
<220> FEATURE:
<221> NAME/KEY: MISC_FEATURE
<222> LOCATION: (4)..(4)
<223> OTHER INFORMATION: Xaa can be His or Pro

<400> SEQUENCE: 73

```
Thr Thr Asp Xaa Asn Met Ala Lys Lys Cys
1               5                   10
```

<210> SEQ ID NO 74
<211> LENGTH: 10
<212> TYPE: PRT
<213> ORGANISM: Artificial sequence
<220> FEATURE:
<223> OTHER INFORMATION: Synthetic - Pep21-SCXP_ANDMA sequence

<400> SEQUENCE: 74

```
Thr Thr Asp Pro Tyr Thr Glu Ser Lys Cys
1               5                   10
```

<210> SEQ ID NO 75
<211> LENGTH: 10
<212> TYPE: PRT
<213> ORGANISM: Artificial sequence
<220> FEATURE:
<223> OTHER INFORMATION: Synthetic - chlorotoxin peptide 21 consensus
      sequence
<220> FEATURE:
<221> NAME/KEY: MISC_FEATURE
<222> LOCATION: (4)..(4)
<223> OTHER INFORMATION: Xaa can be His or Pro
<220> FEATURE:
<221> NAME/KEY: MISC_FEATURE
<222> LOCATION: (5)..(5)
<223> OTHER INFORMATION: Xaa can be Gln or Tyr
<220> FEATURE:
<221> NAME/KEY: MISC_FEATURE
<222> LOCATION: (6)..(6)
<223> OTHER INFORMATION: Xaa can be Met or Thr
<220> FEATURE:
<221> NAME/KEY: MISC_FEATURE
<222> LOCATION: (7)..(7)
<223> OTHER INFORMATION: Xaa can be Ala or Glu
<220> FEATURE:
<221> NAME/KEY: MISC_FEATURE
<222> LOCATION: (8)..(8)
<223> OTHER INFORMATION: Xaa can be Arg or Ser

<400> SEQUENCE: 75

Thr Thr Asp Xaa Xaa Xaa Xaa Xaa Lys Cys

<210> SEQ ID NO 76
<211> LENGTH: 10
<212> TYPE: PRT
<213> ORGANISM: Artificial sequence
<220> FEATURE:
<223> OTHER INFORMATION: Synthetic - chlorotoxin peptide 21 consensus
      sequence

<400> SEQUENCE: 76

Thr Thr Asp Pro Asn Met Ala Lys Lys Cys
1               5                   10

<210> SEQ ID NO 77
<211> LENGTH: 7
<212> TYPE: PRT
<213> ORGANISM: Artificial sequence
<220> FEATURE:
<223> OTHER INFORMATION: Synthetic - chlorotoxin derivative STP-1

<400> SEQUENCE: 77

Thr Asp Pro Gln Met Ser Arg
1               5

<210> SEQ ID NO 78
<211> LENGTH: 10
<212> TYPE: PRT
<213> ORGANISM: Artificial sequence
<220> FEATURE:
<223> OTHER INFORMATION: Synthetic - peptide 8 sequences

<400> SEQUENCE: 78

Gly Gly Lys Gly Arg Gly Lys Ser Tyr Gly
1               5                   10

<210> SEQ ID NO 79
<211> LENGTH: 9
<212> TYPE: PRT
<213> ORGANISM: Artificial sequence
<220> FEATURE:
<223> OTHER INFORMATION: Synthetic - peptide 8a sequence

<400> SEQUENCE: 79

Gly Lys Gly Arg Gly Lys Ser Tyr Gly
1               5

<210> SEQ ID NO 80
<211> LENGTH: 8
<212> TYPE: PRT
<213> ORGANISM: Artificial sequence
<220> FEATURE:
<223> OTHER INFORMATION: Synthetic - peptide 8b sequence

<400> SEQUENCE: 80

Lys Gly Arg Gly Lys Ser Tyr Gly
1               5

<210> SEQ ID NO 81
<211> LENGTH: 7
<212> TYPE: PRT
<213> ORGANISM: Artificial sequence
<220> FEATURE:
<223> OTHER INFORMATION: Synthetic - peptide 8c sequence

<400> SEQUENCE: 81

Gly Arg Gly Lys Ser Tyr Gly

```
1               5

<210> SEQ ID NO 82
<211> LENGTH: 10
<212> TYPE: PRT
<213> ORGANISM: Artificial sequence
<220> FEATURE:
<223> OTHER INFORMATION: Synthetic - peptide 21 sequence

<400> SEQUENCE: 82

Thr Thr Asp His Gln Met Ala Arg Lys Ser
1               5                   10

<210> SEQ ID NO 83
<211> LENGTH: 8
<212> TYPE: PRT
<213> ORGANISM: Artificial sequence
<220> FEATURE:
<223> OTHER INFORMATION: Synthetic - peptide 21b sequence

<400> SEQUENCE: 83

Asp His Gln Met Ala Arg Lys Ser
1               5

<210> SEQ ID NO 84
<211> LENGTH: 7
<212> TYPE: PRT
<213> ORGANISM: Artificial sequence
<220> FEATURE:
<223> OTHER INFORMATION: Synthetic - peptide 21c sequence

<400> SEQUENCE: 84

His Gln Met Ala Arg Lys Ser
1               5

<210> SEQ ID NO 85
<211> LENGTH: 6
<212> TYPE: PRT
<213> ORGANISM: Artificial sequence
<220> FEATURE:
<223> OTHER INFORMATION: Synthetic - peptide 21d sequence

<400> SEQUENCE: 85

Gln Met Ala Arg Lys Ser
1               5

<210> SEQ ID NO 86
<211> LENGTH: 9
<212> TYPE: PRT
<213> ORGANISM: Artificial sequence
<220> FEATURE:
<223> OTHER INFORMATION: Synthetic - peptide 21a-A1 sequence

<400> SEQUENCE: 86

Ala Asp His Gln Met Ala Arg Lys Ser
1               5

<210> SEQ ID NO 87
<211> LENGTH: 9
<212> TYPE: PRT
<213> ORGANISM: Artificial sequence
<220> FEATURE:
<223> OTHER INFORMATION: Synthetic - peptide 21a-A2 sequence

<400> SEQUENCE: 87

Thr Ala His Gln Met Ala Arg Lys Ser
1               5
```

```
<210> SEQ ID NO 88
<211> LENGTH: 9
<212> TYPE: PRT
<213> ORGANISM: Artificial sequence
<220> FEATURE:
<223> OTHER INFORMATION: Synthetic - peptide 21a-A3 sequence

<400> SEQUENCE: 88

Thr Asp Ala Gln Met Ala Arg Lys Ser
1               5

<210> SEQ ID NO 89
<211> LENGTH: 9
<212> TYPE: PRT
<213> ORGANISM: Artificial sequence
<220> FEATURE:
<223> OTHER INFORMATION: Synthetic - peptide 21a-A4 sequence

<400> SEQUENCE: 89

Thr Asp His Ala Met Ala Arg Lys Ser
1               5

<210> SEQ ID NO 90
<211> LENGTH: 9
<212> TYPE: PRT
<213> ORGANISM: Artificial sequence
<220> FEATURE:
<223> OTHER INFORMATION: Synthetic - peptide 21a-A5 sequence

<400> SEQUENCE: 90

Thr Asp His Gln Ala Ala Arg Lys Ser
1               5

<210> SEQ ID NO 91
<211> LENGTH: 9
<212> TYPE: PRT
<213> ORGANISM: Artificial sequence
<220> FEATURE:
<223> OTHER INFORMATION: Synthetic - peptide 21a-A7 sequence

<400> SEQUENCE: 91

Thr Asp His Gln Met Ala Ala Lys Ser
1               5

<210> SEQ ID NO 92
<211> LENGTH: 9
<212> TYPE: PRT
<213> ORGANISM: Artificial sequence
<220> FEATURE:
<223> OTHER INFORMATION: Synthetic - peptide 21a-A8 sequence

<400> SEQUENCE: 92

Thr Asp His Gln Met Ala Arg Ala Ser
1               5

<210> SEQ ID NO 93
<211> LENGTH: 9
<212> TYPE: PRT
<213> ORGANISM: Artificial sequence
<220> FEATURE:
<223> OTHER INFORMATION: Synthetic - peptide 21a-A9 sequence

<400> SEQUENCE: 93

Thr Asp His Gln Met Ala Arg Lys Ala
1               5
```

-continued

```
<210> SEQ ID NO 94
<211> LENGTH: 9
<212> TYPE: PRT
<213> ORGANISM: Mesobuthus tamulus sindicus
<220> FEATURE:
<221> NAME/KEY: misc_feature
<222> LOCATION: (1)..(9)
<223> OTHER INFORMATION: GenBank Accession No. P15229, small toxin

<400> SEQUENCE: 94

Thr Thr Asp Gln Gln Met Ser Lys Lys
1               5

<210> SEQ ID NO 95
<211> LENGTH: 9
<212> TYPE: PRT
<213> ORGANISM: Leiurus quinquestriatus hebraeu
<220> FEATURE:
<221> NAME/KEY: misc_feature
<222> LOCATION: (1)..(9)
<223> OTHER INFORMATION: GenBank Accession No. P55966, probable toxin

<400> SEQUENCE: 95

Thr Thr Asp Pro Gln Met Ser Lys Lys
1               5
```